US008951776B2

(12) United States Patent
Stephanopoulos et al.

(10) Patent No.: US 8,951,776 B2
(45) Date of Patent: Feb. 10, 2015

(54) ENGINEERED MICROBES AND METHODS FOR MICROBIAL OIL PRODUCTION

(71) Applicant: Massachusetts Institute of Technology, Cambridge, MA (US)

(72) Inventors: Gregory Stephanopoulos, Winchester, MA (US); Mitchell Tai, Seattle, WA (US); Sagar Chakraborty, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/656,086

(22) Filed: Oct. 19, 2012

(65) Prior Publication Data
US 2013/0143282 A1  Jun. 6, 2013

Related U.S. Application Data

(60) Provisional application No. 61/548,901, filed on Oct. 19, 2011, provisional application No. 61/663,263, filed on Jun. 22, 2012.

(51) Int. Cl.
*C12P 7/64* (2006.01)
*C12N 1/16* (2006.01)
*C12N 9/10* (2006.01)
*C12N 9/02* (2006.01)
*C12N 15/81* (2006.01)
*C12N 9/88* (2006.01)
*C12N 9/00* (2006.01)

(52) U.S. Cl.
CPC .................. *C12N 15/815* (2013.01); *C12P 7/64* (2013.01); *C12N 1/16* (2013.01); *C12N 9/1029* (2013.01); *C12P 7/6463* (2013.01); *C12N 9/0083* (2013.01); *C12N 9/88* (2013.01); *C12N 9/93* (2013.01)
USPC ........................................ 435/254.2; 435/134

(58) Field of Classification Search
CPC .................................................. C12N 15/8282
USPC .............................................. 435/158, 252.3
See application file for complete search history.

(56) References Cited

U.S. PATENT DOCUMENTS

| | | | |
|---|---|---|---|
| 2006/0051847 A1* | 3/2006 | Gunnarsson et al. | 435/134 |
| 2006/0160193 A1* | 7/2006 | Yadav et al. | 435/134 |
| 2009/0104674 A1* | 4/2009 | Yadav et al. | 435/134 |
| 2011/0177564 A1 | 7/2011 | Stephanopoulos | |
| 2011/0223641 A1 | 9/2011 | Stephanopoulos et al. | |
| 2013/0344548 A1 | 12/2013 | Stephanopoulos et al. | |

OTHER PUBLICATIONS

Beopoulos et al., Yarrowia lipolytica as a model for bio-oil production. Progress in lipid research. 48: 375-387, 2009.*
Tai et al., Engineering the push and pull of lipid biosynthesis in oleaginous yeast Yarrowia lipolytica for biofuel production. Metabolic Engineering 15: 1-9, 2013.*
GENBANK Submission; NCBI, Accession No. NC_006069; Dujon et al.; Apr. 14, 2010.
GENBANK Submission; NCBI, Accession No. XM_001385144.1; Jeffries et al.; Jul. 6, 2010.
GENBANK Submission; NCBI, Accession No. XM_001386945.1; Jeffries et al.; Oct. 7, 2010.
GENBANK Submission; NCBI, Accession No. XM_501496.1; Dujon et al.; Oct. 29, 2008.
GENBANK Submission; NCBI, Accession No. XM_501721.1; Dujon et al.; Oct. 29, 2008.
GENBANK Submission; NCBI, Accession No. XM_503231.1; Dujon et al.; Oct. 29, 2008.
GENBANK Submission; NCBI, Accession No. XM_504700.1; Dujon et al.; Oct. 29, 2008.
GENBANK Submission; NCBI, Accession No. XM_504787; Dujon et al.; Oct. 29, 2008.
GENBANK Submission; NCBI, Accession No. XP_001385181.1; Jeffries et al.; Jul. 6, 2010.
GENBANK Submission; NCBI, Accession No. XP_001386982; Jeffries et al.; Oct. 7, 2010.
Ares et al., A handful of intron-containing genes produces the lion's share of yeast mRNA. RNA. Sep. 1999;5(9):1138-9.
Bailey, Toward a science of metabolic engineering. Science. Jun. 21, 1991;252(5013):1668-75.
Beopoulos et al., Control of lipid accumulation in the yeast Yarrowia lipolytica. Appl Environ Microbiol. Dec. 2008;74(24):7779-89. doi: 10.1128/AEM.01412-08. Epub Oct. 24, 2008.
Beopoulos et al., Yarrowia lipolytica as a model for bio-oil production. Prog Lipid Res. Nov. 2009;48(6):375-87. doi: 10.1016/j.plipres.2009.08.005. Epub Aug. 29, 2009.
Blank et al., Metabolic-flux and network analysis in fourteen hemiascomycetous yeasts. FEMS Yeast Res. Apr. 2005;5(6-7):545-58.
Bon et al., Molecular evolution of eukaryotic genomes: hemiascomycetous yeast spliceosomal introns. Nucleic Acids Res. Feb. 15, 2003;31(4):1121-35.
Boulton et al., Correlation of Lipid Accumulation in Yeasts with Possession of ATP: Citrate Lyase. Microbiology. Nov. 1981;127(1):169-176.
Callis et al., Introns increase gene expression in cultured maize cells. Genes Dev. Dec. 1987;1(10):1183-200.
Cao et al., Increasing unsaturated fatty acid contents in Escherichia coli by coexpression of three different genes. Appl Microbiol Biotechnol. Jun. 2010;87(1):271-80. doi: 10.1007/s00253-009-2377-x. Epub Feb. 5, 2010.

(Continued)

Primary Examiner — Tekchand Saidha
Assistant Examiner — Rama P Ramanujam
(74) Attorney, Agent, or Firm — Wolf, Greenfield & Sacks, P.C.

(57) ABSTRACT

Some aspects of this invention provide engineered microbes for oil production. Methods for microbe engineering and for use of engineered microbes are also provided herein. In some embodiments, microbes are provided that are engineered to modulate a combination of rate-controlling steps of lipid synthesis, for example, a combination of a step generating metabolites, acetyl-CoA, ATP or NADPH for lipid synthesis (a push step), and a step sequestering a product or an intermediate of a lipid synthesis pathway that mediates feedback inhibition of lipid synthesis (a pull step). Such push-and-pull engineered microbes exhibit greatly enhanced conversion yields and TAG synthesis and storage properties.

18 Claims, 13 Drawing Sheets

(56) References Cited

OTHER PUBLICATIONS

Coelho, *Yarrowia lipolytica*: an industrial workhorse. Current research, technology and education topics in applied microbiology and microbial biotechnology. Formatex. 2010;930-944.

Davis et al., Overproduction of acetyl-CoA carboxylase activity increases the rate of fatty acid biosynthesis in *Escherichia coli*. J Biol Chem. Sep. 15, 2000;275(37):28593-8.

Fickers et al., Hydrophobic substrate utilisation by the yeast *Yarrowia lipolytica*, and its potential applications. FEMS Yeast Res. Apr. 2005;5(6-7):527-43.

Folch et al., A simple method for the isolation and purification of total lipides from animal tissues. J Biol Chem. May 1957;226(1):497-509.

Furger et al., Promoter proximal splice sites enhance transcription. Genes Dev. Nov. 1, 2002;16(21):2792-9.

Gasmi et al., Design of an efficient medium for heterologous protein production in *Yarrowia lipolytica*: case of human interferon alpha 2b. Microb Cell Fact. May 20, 2011;10:38. doi: 10.1186/1475-2859-10-38.

Hulver et al., Elevated stearoyl-CoA desaturase-1 expression in skeletal muscle contributes to abnormal fatty acid partitioning in obese humans. Cell Metab. Oct. 2005;2(4):251-61.

Kamiryo et al., Involvement of long-chain acyl coenzyme A for lipid synthesis in repression of acetyl-coenzyme a carboxylase in *Candida lipolytica*. Proc Natl Acad Sci U S A. Sep. 1979;76(9):4390-4.

Kamisaka et al., DGA1 (diacylglycerol acyltransferase gene) overexpression and leucine biosynthesis significantly increase lipid accumulation in the Deltasnf2 disruptant of *Saccharomyces cerevisiae*. Biochem J. Nov. 15, 2007;408(1):61-8.

Kurat et al., Obese yeast: triglyceride lipolysis is functionally conserved from mammals to yeast. J Biol Chem. Jan. 6, 2006;281(1):491-500. Epub Nov. 2, 2005.

Li et al., Perspectives of microbial oils for biodiesel production. Appl Microbiol Biotechnol. Oct. 2008;80(5):749-56. doi: 10.1007/s00253-008-1625-9. Epub Aug. 9, 2008.

Liu et al., Fatty acid production in genetically modified cyanobacteria. Proc Natl Acad Sci U S A. Apr. 26, 2011;108(17):6899-904. doi: 10.1073/pnas.1103014108. Epub Apr. 11, 2011.

Morin et al., Transcriptomic analyses during the transition from biomass production to lipid accumulation in the oleaginous yeast *Yarrowia lipolytica*. PLoS One. 2011;6(11):e27966. doi: 10.1371/journal.pone.0027966. Epub Nov. 22, 2011.

Müller et al., Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from *Yarrowia lipolytica*. Yeast. Oct. 1998;14(14):1267-83.

Nicaud et al., Protein expression and secretion in the yeast *Yarrowia lipolytica*. FEMS Yeast Res. Aug. 2002;2(3):371-9.

Ntambi et al., Regulation of stearoyl-CoA desaturases and role in metabolism. Prog Lipid Res. Mar. 2004;43(2):91-104.

Oelkers et al., The DGA1 gene determines a second triglyceride synthetic pathway in yeast. J Biol Chem. Mar. 15, 2002;277(11):8877-81. Epub Dec. 18, 2001.

Papanikolaou et al., Single cell oil production by *Yarrowia lipolytica* growing on an industrial derivative of animal fat in batch cultures. Appl Microbiol Biotechnol. Mar. 2002;58(3):308-12. Epub Dec. 11, 2001.

Papanikolaou et al., *Yarrowia lipolytica* as a potential producer of citric acid from raw glycerol. J Appl Microbiol. 2002;92(4):737-44.

Roesler et al., Targeting of the *Arabidopsis* homomeric acetyl-coenzyme A carboxylase to plastids of rapeseeds. Plant Physiol. Jan. 1997;113(1):75-81.

Shen et al., Driving forces enable high-titer anaerobic 1-butanol synthesis in *Escherichia coli*. Appl Environ Microbiol. May 2011;77(9):2905-15. doi: 10.1128/AEM.03034-10. Epub Mar. 11, 2011.

Tai et al., Expression enhancing introns for increased protein expression in yeast. AIChE. Oct. 20, 2011.

Tai et al., Towards cellulosic biodiesel: engineering xylose and lipid metabolism in yeast. AIChE. Oct. 19, 2011.

Tehlivets et al., Fatty acid synthesis and elongation in yeast. Biochim Biophys Acta. Mar. 2007;1771(3):255-70. Epub Jul. 21, 2006.

Tsai et al., Engineering the push and pull of lipid biosynthesis in oleaginous yeast *Yarrowia lipolytica* for biofuel production. Metab Eng. Jan. 2013;15:1-9. doi: 10.1016/j.ymben.2012.08.007. Epub Sep. 28, 2012.

Vorapreeda et al., Alternative routes of acetyl-CoA synthesis identified by comparative genomic analysis: involvement in the lipid production of oleaginous yeast and fungi. Microbiology. Jan. 2012;158(Pt 1):217-28. doi: 10.1099/mic.0.051946-0. Epub Oct. 20, 2011.

Zhang et al., Three diacylglycerol acyltransferases contribute to oil biosynthesis and normal growth in *Yarrowia lipolytica*. Yeast. Jan. 2012;29(1):25-38. doi: 10.1002/yea.1914. Epub Dec. 20, 2011.

Zhao et al., Comprehensive algorithm for quantitative real-time polymerase chain reaction. J Comput Biol. Oct. 2005;12(8):1047-64.

Aggelis et al., Enhancement of single cell oil production by *Yarrowia lipolytica* growing in the presence of *Teucrium polium* L. aqueous extract. Biotechnology Letters. 1999;21(9):747-749.

Andrianov et al., Tobacco as a production platform for biofuel: overexpression of *Arabidopsis* DGAT and LEC2 genes increases accumulation and shifts the composition of lipids in green biomass. Plant Biotechnol J. Apr. 2010;8(3):277-87. doi: 10.1111/j.1467-7652.2009.00458.x. Epub Dec. 23, 2009.

Athenstaedt et al., Lipid particle composition of the yeast *Yarrowia lipolytica* depends on the carbon source. Proteomics. Mar. 2006;6(5):1450-9.

Balan et al., Lignocellulosic biomass pretreatment using AFEX. Methods Mol Biol. 2009;581:61-77. doi: 10.1007/978-1-60761-214-8_5.

Barth et al., Physiology and genetics of the dimorphic fungus *Yarrowia lipolytica*. FEMS Microbiol Rev. Apr. 1997;19(4):219-37.

Beckerich et al., *Yarrowia lipolytica*: a model organism for protein secretion studies. Int Microbiol. Jun. 1998;1(2):123-30.

Beopoulos et al., An overview of lipid metabolism in yeasts and its impact on biotechnological processes. Appl Microbiol Biotechnol. May 2011;90(4):1193-206.

Brownsey et al., Regulation of acetyl-CoA carboxylase. Biochem Soc Trans. Apr. 2006;34(Pt 2):223-7.

Chen et al., One-step transformation of the dimorphic yeast *Yarrowia lipolytica*. Appl Microbiol Biotechnol. Aug. 1997;48(2):232-5.

Chuang et al., Co-expression of heterologous desaturase genes in *Yarrowia lipolytica*. N Biotechnol. Sep. 30, 2010;27(4):277-82. doi: 10.1016/j.nbt.2010.02.006. Epub Feb. 25, 2010.

Courchesne et al., Enhancement of lipid production using biochemical, genetic and transcription factor engineering approaches. J Biotechnol. Apr. 20, 2009;141(1-2):31-41.

Cui et al., Direct conversion of inulin into single cell protein by the engineered *Yarrowia lipolytica* carrying inulinase gene. Process Biochem. Jul. 2011;46 (7):1442-1448.

Dobrzyn et al., The role of stearoyl-CoA desaturase in the control of metabolism. Prostaglandins Leukot Essent Fatty Acids. Jul. 2005;73(1):35-41.

Dulermo et al., Involvement of the G3P shuttle and β-oxidation pathway in the control of TAG synthesis and lipid accumulation in *Yarrowia lipolytica*. Metab Eng. Sep. 2011;13(5):482-91. doi: 10.1016/j.ymben.2011.05.002. Epub May 23, 2011.

Feist et al., Model-driven evaluation of the production potential for growth-coupled products of *Escherichia coli*. Metab Eng. May 2010;12(3):173-86. doi: 10.1016/j.ymben.2009.10.003. Epub Oct. 17, 2009.

Griffiths et al., Selection of direct transesterification as the preferred method for assay of fatty acid content of microalgae. Lipids. Nov. 2010;45(11):1053-60. Epub Sep. 5, 2010.

Huo et al., Conversion of proteins into biofuels by engineering nitrogen flux. Nat Biotechnol. Apr. 2011;29(4):346-51. doi: 10.1038/nbt.1789. Epub Mar. 6, 2011.

Ivashchenko et al., Exon-intron structure of genes of fungi genomes. Mol Biol (Mosk). Jan.-Feb. 2009;43(1):28-35. Russian.

(56) References Cited

OTHER PUBLICATIONS

Karatay et al., Improving the lipid accumulation properties of the yeast cells for biodiesel production using molasses. Bioresour Technol. Jun. 11, 2010.;101:7988-7990. [Epub ahead of print].

Keasling, Manufacturing molecules through metabolic engineering. Science. Dec. 3, 2010;330(6009):1355-8. doi: 10.1126/science.1193990.

Kerscher et al., Yarrowia lipolytica, a yeast genetic system to study mitochondrial complex I. Biochim Biophys Acta. Sep. 10, 2002;1555(1-3):83-91.

Klaus et al., Increased fatty acid production in potato by engineering of acetyl-CoA carboxylase. Planta. Jul. 2004;219(3):389-96. Epub Mar. 10, 2004.

Kohlwein et al., Lipid-induced cell dysfunction and cell death: lessons from yeast. Curr Hypertens Rep. Dec. 2007;9(6):455-61.

Le Hir et al., How introns influence and enhance eukaryotic gene expression. Trends Biochem Sci. Apr. 2003;28(4):215-20.

Madzak et al., Heterologous protein expression and secretion in the non-conventional yeast Yarrowia lipolytica: a review. J Biotechnol. Apr. 8, 2004;109(1-2):63-81.

Madzak et al., Strong hybrid promoters and integrative expression/secretion vectors for quasi-constitutive expression of heterologous proteins in the yeast Yarrowia lipolytica. J Mol Microbiol Biotechnol. Apr. 2000;2(2):207-16.

Ohlrogge et al., Regulation of Fatty Acid Synthesis. Annu Rev Plant Physiol Plant Mol Biol. Jun. 1997;48:109-136.

Papanikolaou et al., Accumulation of a cocoa-butter-like lipid by Yarrowia lipolytica cultivated on agro-industrial residues. Curr Microbiol. Feb. 2003;46(2):124-30.

Papanikolaou et al., Influence of glucose and saturated free-fatty acid mixtures on citric acid and lipid production by Yarrowia lipolytica. Curr Microbiol. Feb. 2006;52(2):134-42. Epub Jan. 2, 2006.

Papanikolaou et al., Lipid production by Yarrowia lipolytica growing on industrial glycerol in a single-stage continuous culture. Bioresour Technol. Mar. 2002;82(1):43-9.

Papanikolaou et al., Modeling lipid accumulation and degradation in Yarrowia lipolytica cultivated on industrial fats. Curr Microbiol. Jun. 2003;46(6):398-402.

Ratledge, Biochemistry, stoichiometry, substrates and economics. In: Moreton RS, editor. Single Cell Oil. London: Longman Scientific & Technical; 1988. pp. 33-70.

Ruenwai et al., Overexpression of acetyl-CoA carboxylase gene of Mucor rouxii enhanced fatty acid content in Hansenula polymorpha. Mol Biotechnol. Jul. 2009;42(3):327-32. doi: 10.1007/s12033-009-9155-y. Epub Mar. 5, 2009.

Scioli et al., The use of Yarrowia lipolytica to reduce pollution in olive mill wastewaters. Water Research. 1997;31(10):2520-2524.

Stephanopoulos, Challenges in engineering microbes for biofuels production. Science. Feb. 9, 2007;315(5813):801-4.

Tsigie etal., Lipid production from Yarrowia lipolytica Polg grown in sugarcane bagasse hydrolysate. Bioresour Technol. Oct. 2011;102(19):9216-22. doi:10.1016/j.biortech.2011.06.047. Epub Jun. 22, 2011.

Tyo et al., Expanding the metabolic engineering toolbox: more options to engineer cells. Trends Biotechnol. Mar. 2007;25(3):132-7. Epub Jan. 24, 2007.

Yang et al., Dilute acid and autohydrolysis pretreatment. Methods Mol Biol. 2009;581:103-14.

Zhao et al., Expression of inulinase gene in the oleaginous yeast Yarrowia lipolytica and single ell oil production from inulin-containing materials. Metab Eng. Nov. 2010;12(6):510-7. Epub Sep. 29, 2010.

\* cited by examiner

ENGINEERED MICROBES AND METHODS FOR MICROBIAL OIL PRODUCTION

RELATED APPLICATIONS

This application claims priority under 35 U.S.C. §119 to U.S. provisional patent application U.S. Ser. No. 61/548,901, filed Oct. 19, 2011; and U.S. provisional patent application U.S. Ser. No. 61/663,263, filed Jun. 22, 2012, both entitled "Engineered Microbes and Methods for Microbial Oil Production," the entire contents of each of which are incorporated herein by reference.

GOVERNMENT SUPPORT

This invention was made with government support under Grant No. DE-AR0000059 awarded by the US Department of Energy. The government has certain rights in this invention.

BACKGROUND

Sustainably produced biofuels are an alternative to fossil fuels and may help to alleviate the depletion of easily accessible fossil fuel stocks while avoiding fossil fuel-associated pollution and greenhouse gas emission, thus satisfying a rising demand for affordable energy in a sustainable way. The development of methods and oil-producing organisms suitable for the efficient conversion of carbon sources to lipids is prerequisite for widespread implementation of microbial biofuel production.

SUMMARY OF CERTAIN ASPECTS OF THE INVENTION

Microbial oil production by heterotrophic organisms is a most promising path for the cost-effective production of biofuels from renewable resources provided high conversion yields can be achieved. The key to cost-effective microbial oil production from renewable feedstocks is a high carbohydrate to oil conversion yield. Metabolic engineering has emerged as the enabling technology applied to this end and numerous examples exist of successful pathway engineering that markedly improved the performance of microbial biocatalysts in the synthesis of chemical, pharmaceutical and fuel products.

Prior efforts at engineering microbes for oil production have focused on amplifying presumed rate-controlling steps in the fatty acid synthesis pathway. One significant drawback of such amplifications is that increasing carbon flux into fatty acid synthesis pathways increases the level of saturated fatty acids in the cell, which activate a potent negative feedback loop of fatty acid biosynthesis.

Some aspects of this disclosure provide a strategy for microbe engineering that combines the amplification of upstream, metabolite-forming pathways, also referred to herein as "push" metabolic pathways, with a similar increase in the flux of downstream, product-sequestering pathways, also referred to herein as "pull" pathways. Some aspects of this invention provide that a balanced combination of push-and-pull modifications in a microbe results in large carbon flux amplifications into lipid synthesis pathways without significant departures of the concentrations of intermediate metabolites from their homeostatic physiological levels, thus avoiding feedback inhibition of lipid synthesis.

Some aspects of this disclosure relate to the recognition that the effects of single-branch modifications, e.g., push-only modifications or pull-only modifications, on conversion efficiency are typically limited because of compensatory regulation of synthesis yield in the cell, and that a concerted modulation of push and pull steps of lipid biosynthesis in microbial cells results in a surprising synergistic effect on lipid production.

For example, some aspects of this disclosure provide genetically modified oleaginous microbes comprising a combination of modifications in their lipid biosynthetic pathways, also referred to herein as push-pull modifications. In some embodiments, a microbe provided herein comprises a modification effecting an increased production of metabolites or intermediates required for lipid synthesis and a modification resulting in sequestration of a product of lipid synthesis, for example, of triacylglycerol into a storage form lipid within the cell, thus alleviating feedback inhibition of lipid synthesis by some of its products, e.g., by fatty acids or diacylglycerols. In some embodiments, the combination of modifications of the metabolic push and metabolic pull pathways results in a synergistically increased lipid production. In some embodiments, the push modification results in an increased level of lipid-synthesis building blocks, or metabolites for lipid synthesis, in the cell. In some embodiments, the pull modification alleviates feedback inhibition on lipid synthesis.

Some aspects of this invention provide microbes that comprise genetic modifications simultaneously affecting a push- and a pull pathway of lipid biosynthesis. For example, push and pull modifications were introduced into a model microbe for oil production, the oleaginous yeast *Yarrowia lipolytica*. The overexpression of diacylglycerol acyltransferase (DGA1), the final step of the triglyceride (TAG) synthesis pathway, was investigated as an exemplary pull modification. DGA1 overexpression resulted in a 4-fold increase in lipid production over control microbes, to a lipid content of 33.8% of dry cell weight (DCW). The overexpression of acetyl-CoA carboxylase (ACC1), the first committed step of fatty acid synthesis, was investigated as an exemplary push modification. ACC1 overexpression increased lipid content 2-fold over control, to a lipid content of 17.9%. Simultaneous coexpression of ACC1 and DGA1 from a tandem gene expression construct was investigated as an exemplary push-pull modification. Simultaneous ACC1 and DGA1 overexpression further increased lipid content to 41.4%, demonstrating synergistic effects of ACC1+DGA1 coexpression.

The lipid production characteristics of the ACC1+DGA1 transformant were explored in a 2-L bioreactor fermentation, achieving 61.7% lipid content after 120 hr. The overall yield and productivity were 0.195 g/g and 0.143 g/L/hr, respectively, while the maximum yield and productivity were 0.270 g/g and 0.253 g/L/hr during the lipid accumulation phase of the fermentation. This work demonstrates the excellent capacity for lipid production by the oleaginous yeast *Y. lipolytica* and the effects of metabolic engineering of two important steps of the lipid synthesis pathway, which acts to divert flux towards the lipid synthesis and creates driving force for TAG synthesis.

Some aspects of this invention provide a novel overexpression platform for use in oil-producing microbes, for example, in oleaginous yeast. Some aspects of this invention provide expression constructs comprising a promoter driving transcription of a transcript that comprises a coding sequence and an intron, for example, a translation elongation factor-1α (TEF) promoter positioned upstream of a nucleic acid sequence comprising an intron and a coding sequence. Some aspects of this disclosure provide that such intron-containing expression constructs are capable of increasing expression at least 17-fold over the intronless TEF promoter.

Some aspects of this disclosure provide an isolated oleaginous cell comprising a genetic modification that increases expression of a DGA1 gene product. In some embodiments, the isolated oleaginous cell further comprises a genetic modification that increases expression of an ACC1 gene product. In some embodiments, the isolated oleaginous cell further comprises a genetic modification that increases expression of an SCD gene product. In some embodiments, the isolated oleaginous cell further comprises a genetic modification that increases expression of an ACL gene product. In some embodiments, the genetic modification comprises a nucleic acid construct that increases the expression of the gene product, the nucleic acid construct comprising (a) an expression cassette comprising a nucleic acid sequence encoding the gene product under the control of a suitable homologous or heterologous promoter, and/or (b) a nucleic acid sequence that modulates the level of expression of the gene product when inserted into the genome of the cell. In some embodiments, the promoter is an inducible or a constitutive promoter. In some embodiments, the promoter is a TEF promoter. In some embodiments, the expression construct further comprises an intron. In some embodiments, the intron is downstream of the transcription initiation site. In some embodiments, the intron is within the nucleic acid sequence encoding the gene product. In some embodiments, the nucleic acid construct inhibits or disrupts the natural regulation of a native gene encoding the gene product resulting in overexpression of the native gene. In some embodiments, inhibition or disruption of the natural regulation of the native gene is mediated by deletion, disruption, mutation and/or substitution of a regulatory region, or a part of a regulatory region regulating expression of the gene. In some embodiments, the gene product is a transcript. In some embodiments, the gene product is a protein. In some embodiments, the nucleic acid construct is inserted into the genome of the cell. In some embodiments, the increased expression of the gene product confers a beneficial phenotype for the conversion of a carbon source to a lipid, e.g., a fatty acid, fatty acid derivative and/or triacylglycerol (TAG) to the cell. In some embodiments, the beneficial phenotype comprises a modified fatty acid profile, a modified TAG profile, an increased fatty acid and/or triacylglycerol synthesis rate, an increase conversion yield, an increased triacylglycerol accumulation in the cell, and/or an increased triacylglycerol accumulation in a lipid body of the cell. In some embodiments, the synthesis rate of a fatty acid or a TAG of the cell is at least 2-fold increased as compared to unmodified cells of the same cell type. In some embodiments, the synthesis rate of a fatty acid or a TAG of the cell is at least 5-fold increased as compared to unmodified cells of the same cell type. In some embodiments, the synthesis rate of a fatty acid or a TAG of the cell is at least 10-fold increased as compared to unmodified cells of the same cell type. In some embodiments, the cell converts a carbon source to a fatty acid or a TAG at a conversion rate within the range of about 0.025 g/g to about 0.32 g/g (e.g., g lipid produced/g carbon source consumed). In some embodiments, the cell converts a carbon source to a fatty acid or a TAG at a conversion rate of at least about 0.11 g/g. In some embodiments, the cell converts a carbon source to a fatty acid or a TAG at a conversion rate of at least about 0.195 g/g. In some embodiments, the cell converts a carbon source to a fatty acid or a TAG at a conversion rate of at least about 0.24 g/g. In some embodiments, the cell converts a carbon source to a fatty acid or a TAG at a conversion rate of at least about 0.27 g/g. In some embodiments, the cell comprises a lipid body or vacuole. In some embodiments, the cell is a bacterial cell, an algal cell, a fungal cell, or a yeast cell. In some embodiments, the cell is an oleaginous yeast cell. In some embodiments, the cell is a *Y. lipolytica* cell.

Some aspects of this disclosure provide a culture comprising an oleaginous cell, e.g., an oleaginous cell as described herein. In some embodiments, the culture further comprises a carbon source. In some embodiments, the carbon source comprises a fermentable sugar. In some embodiments, the fermentable sugar is a C6 sugar. In some embodiments, the carbon source comprises glucose. In some embodiments, the carbon source comprises an organic acid. In some embodiments, the organic acid is acetic acid. In some embodiments, the acetic acid is at a concentration of at least 5% vol/vol, at least 10% vol/vol, at least 15% vol/vol, at least 20% vol/vol, at least 25% vol/vol, or at least 30% vol/vol. In some embodiments, the carbon source comprises acetate. In some embodiments, the acetate is at a concentration of at least 1% vol/vol. In some embodiments, the acetate is at a concentration of at least 2% vol/vol. In some embodiments, the acetate is at a concentration of at least 3% vol/vol. In some embodiments, the acetate is at a concentration of at least 4% vol/vol. In some embodiments, the acetate is at a concentration of at least 5% vol/vol. In some embodiments, the culture comprises glycerol. In some embodiments, the glycerol is at a concentration of about 2% vol/vol. In some embodiments, the culture comprises a dissolved oxygen level of at least 5%, at least 10%, at least 15%, or at least 20%. In some embodiments, the culture exhibits a pH within the range of pH7.0 to pH7.5. In some embodiments, the culture comprises ammonium sulfate. In some embodiments, the culture comprises ammonium sulfate and acetic acid at a ratio of 1:2. In some embodiments, the culture exhibits a lipid titer between 5 g/l and 60 g/l. In some embodiments, the culture exhibits a lipid production between 0.04 g/l/h and 0.60 g/l/h. In some embodiments, the culture exhibits a maximum lipid productivity of between 0.1 g/l/h and 1 g/l/h.

Some aspects of this disclosure provide a method comprising contacting a carbon source with an isolated oleaginous cell, the cell comprising a genetic modification that increases expression of a DGA1 gene product; and incubating the carbon source contacted with the cell under conditions suitable for at least partial conversion of the carbon source into a fatty acid or a triacylglycerol by the cell. In some embodiments, the oleaginous cell further comprises a genetic modification that increases expression of an ACC1 gene product. In some embodiments, the oleaginous cell further comprises a genetic modification that increases expression of an SCD gene product. In some embodiments, the oleaginous cell further comprises a genetic modification that increases expression of an ACL gene product. In some embodiments, the isolated oleaginous cell is an engineered isolated oleaginous cell as described herein. In some embodiments, the carbon source comprises a fermentable sugar. In some embodiments, the carbon source comprises glucose. In some embodiments, the carbon source comprises acetate. In some embodiments, the acetate is at a concentration of at least 1% vol/vol, of at least 2% vol/vol, of at least 3% vol/vol, of at least 4% vol/vol, or of at least 5% vol/vol. In some embodiments, the carbon source comprises acetic acid. In some embodiments, the acetic acid is at a concentration of at least 5% vol/vol, at least 10% vol/vol, at least 15% vol/vol, at least 20% vol/vol, at least 25% vol/vol, or at least 30% vol/vol. In some embodiments, the method comprises contacting the cell with dissolved oxygen at a level of at least 5%, at least 10%, at least 15%, or at least 20%. In some embodiments, the contacting and/or the incubating is performed at a pH within the range of pH7.0 to pH7.5. 70. The method of any one of claims 53-69, wherein the method comprises contacting the cell with ammonium sulfate. In some embodiments, the method comprises contacting the cell with ammonium sulfate and acetic acid at a ratio of 1:2. In some embodiments, the method further comprises contacting the cells with glycerol. In some embodiments, the method comprises contacting the cells with glycerol at a concentration of about 2% vol/vol. In some embodiments, the carbon source contacted with the isolated oleaginous cell is incubated in a reactor. In some embodiments, the carbon source is contacted with the isolated oleaginous cell and incubated for conversion of the carbon source to a fatty acid or a triacylglycerol in a fed batch process. In some embodiments, the carbon source is contacted with the isolated oleaginous cell and incubated for conversion of the carbon source to a fatty acid or a triacylglycerol in a continuous process. In some embodiments, the method further comprises contacting an additional amount of the carbon source or an amount of an additional carbon source with the carbon source contacted with the isolated oleaginous cell one or more times during the incubating step. In some embodiments, the fatty acid or the triacylglycerol is extracted from the carbon source contacted with the isolated oleaginous cell by solvent extraction. In some embodiments, the solvent extraction comprises a chloroform methanol extraction. In some embodiments, the solvent extraction comprises a hexane extraction. In some embodiments, the fatty acid or the triacylglycerol is separated from the carbon source contacted with the isolated oleaginous cell and subsequently refined by transesterification.

Some aspects of this disclosure provide a method comprising modifying the fatty acid profile, the triacylglycerol profile, the fatty acid synthesis rate, the triacylglycerol synthesis rate, the extent of fatty acid derivative accumulation, the rate of fatty acid derivative secretion, the rate of carbohydrate to fatty acid or fatty acid derivative conversion, and/or the efficient yield of carbohydrate to fatty acid or fatty acid derivative conversion in an oleaginous cell by increasing in the cell the expression of a DGA1 gene product. In some embodiments, the method further comprises increasing in the cell the expression of an ACC1 gene product, of an SCD gene product, and/or of an ACL gene product. In some embodiments, the extent of fatty acid derivative accumulation is the extent of fatty acid derivative accumulation in a lipid body. In some embodiments, the fatty acid derivative is a triacylglycerol. In some embodiments, modifying the fatty acid profile, the triacylglycerol profile, the fatty acid synthesis rate, the triacylglycerol synthesis rate, the extent of fatty acid derivative accumulation, the rate of fatty acid derivative secretion, the rate of carbohydrate to fatty acid or fatty acid derivative conversion, and/or the efficient yield of carbohydrate to fatty acid or fatty acid derivative conversion in the oleaginous cell comprises increasing the fatty acid synthesis rate, the triacylglycerol synthesis rate, the extent of fatty acid derivative accumulation, the rate of fatty acid derivative secretion, the rate of carbohydrate to fatty acid or fatty acid derivative conversion, and/or the efficient yield of carbohydrate to fatty acid or fatty acid derivative conversion in the oleaginous cell. In some embodiments, modifying the efficiency of carbohydrate to fatty acid or fatty acid derivative conversion of the cell comprises increasing the efficiency of conversion by at least 2-fold. In some embodiments, modifying the efficiency of carbohydrate to fatty acid or fatty acid derivative conversion of the cell comprises increasing the efficiency of conversion by at least 3-fold. In some embodiments, modifying the efficiency of carbohydrate to fatty acid or fatty acid derivative conversion of the cell comprises increasing the efficiency of conversion by at least 4-fold. In some embodiments, modifying the efficiency of carbohydrate to fatty acid or fatty acid derivative conversion of the cell comprises increasing the efficiency of conversion by at least 5-fold. In some embodiments, the cell is a yeast cell. In some embodiments, the yeast cell is a *Yarrowia* sp. cell. In some embodiments, the oleaginous yeast is *Y. lipolytica*.

Some aspects of this disclosure provide an isolated nucleic acid molecule comprising: a) a nucleotide sequence that encodes SEQ ID NO: 2 (*Y. lipolytica* DGA1), or b) a nucleotide sequence that is at least 85% identical to the nucleotide sequence of a). In some embodiments, the nucleotide sequence that encodes SEQ ID NO:2 comprises SEQ ID NO: 1. Some aspects of this disclosure provide an expression cassette comprising an isolated nucleic acid molecule as described herein and a heterologous promoter. In some embodiments, the promoter is a constitutive promoter or an inducible promoter. In some embodiments, the heterologous promoter is a Translation Elongation Factor (TEF) promoter. In some embodiments, the heterologous promoter comprises an intron. In some embodiments, the heterologous promoter further comprises a start codon. In some embodiments, the intron is downstream of the translation start site of the nucleotide sequence that encodes SEQ ID NO: 2. Some aspects of this disclosure provide a vector comprising an expression cassette as described herein. Some aspects of this disclosure provide a cell comprising an expression cassette as described herein or at least a part of a vector described herein.

The subject matter of this application may involve, in some cases, interrelated products, alternative solutions to a particular problem, and/or a plurality of different uses of a single system or article.

Other advantages, features, and uses of the invention will be apparent from the detailed description of certain non-limiting embodiments, the drawings, and the claims.

DETAILED DESCRIPTION OF CERTAIN EMBODIMENTS OF THE INVENTION

Figure 1:
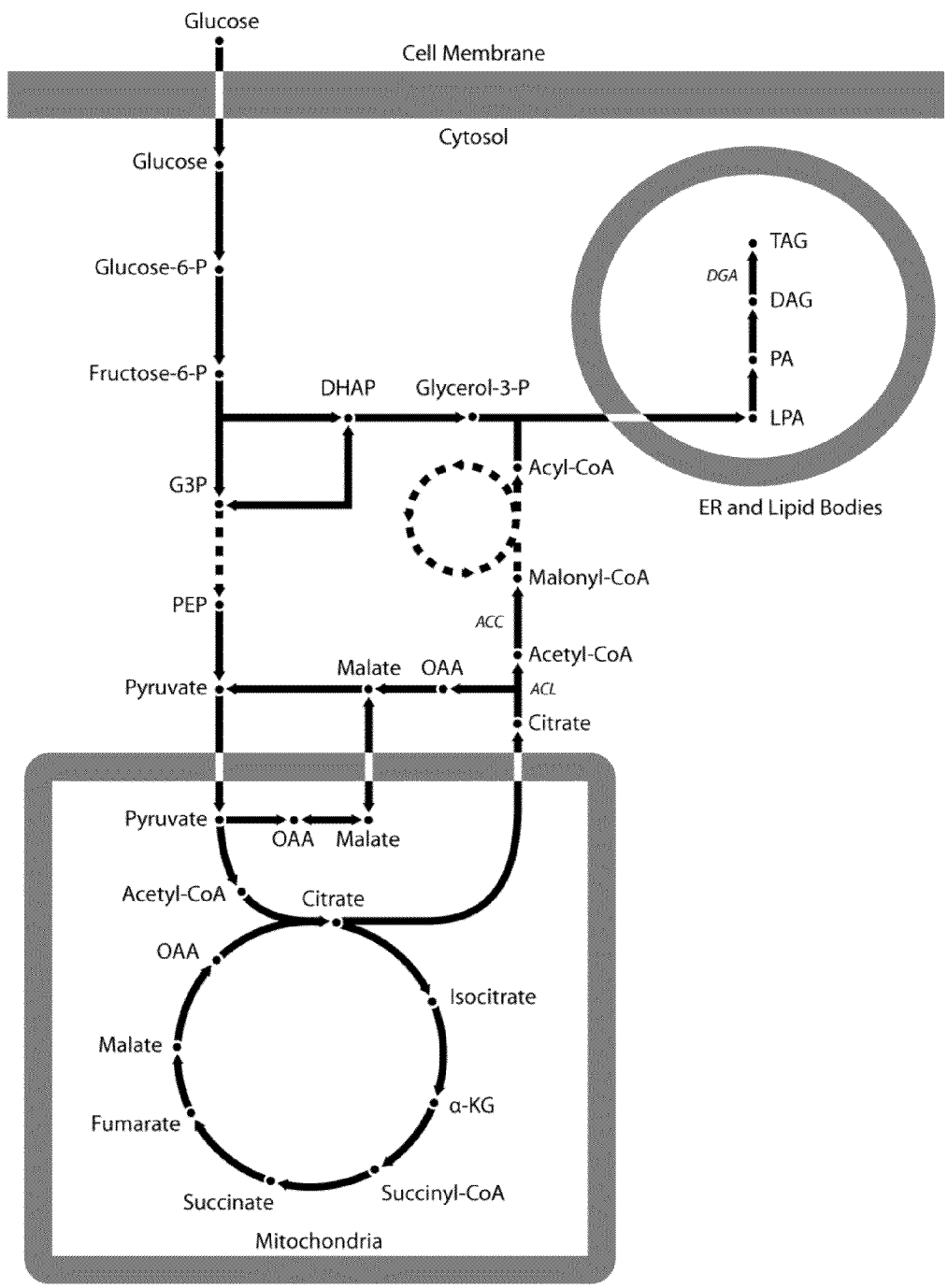
FIG. 1. Overview of the principal metabolic pathways for lipid synthesis in *Y. lipolytica*.
Figure 2:
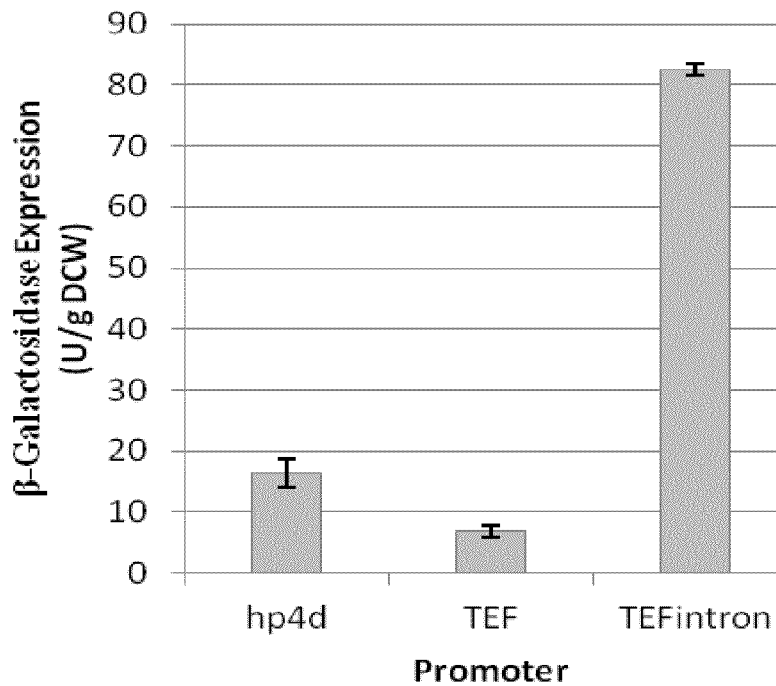
FIG. 2. Enzyme activity of β-galactosidase under different promoters after 50 hours of culture.

Liquid biofuels are a promising alternative to fossil fuels that can help ease concerns about climate change and smoothen supply uncertainties (1). Biodiesel, jet oil and other oil-derived fuels in particular are necessary for aviation and heavy vehicle transport. They are presently produced exclusively from vegetable oils, which is a costly and unsustainable path (2). An attractive possibility is the non-photosynthetic conversion of renewable carbohydrate feedstocks to oil (3). For biodiesel, a transition from vegetable oil to microbial oil production for the oil feedstock presents numerous additional advantages: adaptability to diverse feedstocks, flexibility in land requirements, efficient process cycle turnover, and ease of scale-up (4). The biological platforms for microbial production are also more genetically tractable for further optimization.

The key to a cost-effective microbial technology for the conversion of carbohydrates to oils is a high carbohydrate to oil conversion yield. Metabolic engineering has emerged as the enabling technology applied to this end and numerous examples exist of successful pathway engineering that markedly improved the performance of microbial biocatalysts in the synthesis of chemical, pharmaceutical and fuel products (5). Prior efforts at engineering microbes with high lipid synthesis have focused on amplifying presumed rate-controlling steps in the fatty acid synthesis pathway (6). These efforts, however, have produced mixed results, presumably because modulating fatty acid flux gave rise to the levels of saturated fatty acids, which are potent allosteric inhibitors of fatty acid biosynthetic enzymes providing a negative feedback loop for the fatty acid biosynthesis (7). Here we describe an approach that combines the amplification of upstream, metabolite-forming pathways with a similar increase in the flux of downstream, metabolite-consuming pathways. When balanced, this push-and-pull strategy can achieve large flux amplifications without significant departures of the concentrations of intermediate metabolites from their homeostatic physiological levels.

The oleaginous yeast *Yarrowia lipolytica* is an attractive candidate for microbial oil production, which has also demonstrated usefulness in a wide range of other industrial applications: citric acid production, protein production (e.g., proteases and lipases), and bioremediation (8-10). With a fully sequenced genome and a growing body of genetic engineering tools, engineering of *Y. lipolytica* can be achieved with relative ease (11). *Y. lipolytica* also has been found to be robust in culture, able to grow on a variety of substrates, and has been used for lipid production on agro-industrial residues, industrial glycerol, and industrial fats (12-14). It has excellent lipid accumulation capacity, commonly accumulating up to 36% of its dry cell weight (DCW) in lipids (15).

The metabolic pathways for de novo lipid synthesis in *Y. lipolytica* are beginning to be fully mapped out, and a current model of lipid synthesis is illustrated in FIG. 1: Glucose entering glycolysis enters the mitochondria as pyruvate for use in the TCA cycle; however, excess acetyl-coA is transported from the mitochondria to the cytosol via the citrate shuttle. Cytosolic acetyl-CoA is then converted into malonyl-CoA by acetyl-CoA carboxylase (ACC) as the first step of fatty acid synthesis. After fatty acid synthesis, triacylglycerol (TAG) synthesis follows the Kennedy pathway, which occurs in the endoplasmic reticulum (ER) and lipid bodies. Acyl-CoA is the precursor used for acylation to the glycerol-3-phosphate backbone to form lysophosphatidic acid (LPA), which is further acylated to form phosphatidic acid (PA). PA is then dephosphorylated to form diacylglycerol (DAG) and then a final acylation occurs by diacylglycerol acyltransferase (DGA) to produce TAG.

Transport of acetyl-CoA from the mitochondria to the cytosol is carried out by the ATP-citrate lyase (ACL)-mediated cleavage of citrate via the citrate shuttle yielding Acetyl-CoA and Oxaloacetate (OAA). Acetyl-CoA carboxylase (ACC) then catalyzes the first committed step towards lipid biosynthesis, converting cytosolic acetyl-CoA into malonyl-CoA, which is the primary precursor for fatty acid elongation. Completed fatty acyl-CoA chains are then transported to the endoplasmic reticulum (ER) or lipid body membranes for the final assembly of triacylglycerol (TAG) via the Kennedy pathway. Over 80% of the storage lipids produced in *Y. lipolytica* are in the form of TAG (16). Cytosolic OAA is converted to malate by malic dehydrogenase and transported back into the mitochondria to complete the citrate shuttle cycle. Reducing equivalents in the form of NADPH is provided either by the pentose phosphate pathway or by malic enzyme in the transhydrogenase cycle. In *Y. lipolytica*, high PPP flux and ineffectual malic enzyme overexpression suggest that the former is the primary source for NADPH (4, 17).

Intracellular lipid accumulation can occur via two methods: de novo lipid synthesis or ex novo incorporation of exogenous fatty acids and lipids. Lipid accumulation most commonly occurs when nutrient supply is exhausted in the presence of excess carbon. In culture, this state typically coincides with the onset of the stationary phase. In practice, the most commonly used limiting-nutrient is nitrogen, as it is easily controllable in media compositions (15). Despite these inducible conditions, lipid synthesis pathways are highly regulated in order for the organism to balance cell growth with energy storage. For example, ACC alone is regulated at multiple levels and by multiple factors (7).

This tight regulation was circumvented in certain cases. By eliminating peroxisomal oxidation pathways and engineering glycerol metabolism, *Y. lipolytica* was able to achieve 40%-70% lipids through ex novo lipid accumulation (18, 19). Coexpression of Δ6- and Δ12-desaturase genes allowed for significant production of γ-linolenic acid (GLA) (20). However, engineering lipid biosynthesis pathways in *Y. lipolytica* is still relatively unexplored and strategies are still being developed for effective engineering of the lipid production pathways to maximize output.

Some aspects of this disclosure provide engineered microbes for the production of biofuel or biofuel precursor. The term "biofuel" refers to a fuel that is derived from a biological source, such as a living cell, microbe, fungus, or plant. The term includes, for example, fuel directly obtained from a biological source, for example, by conventional extraction, distillation, or refining methods, and fuel produced by processing a biofuel precursor obtained from a biological source, for example by chemical modification, such as transesterification procedures. Examples of biofuels that are directly obtainable are alcohols such as ethanol, propanol, and butanol, fat, and oil. Examples of biofuels that are obtained by processing of a biofuel precursor (e.g., a lipid), are biodiesel (e.g., produced by transesterification of a lipid), and green diesel/modified oil fuels (e.g., produced by hydrogenation of an oil). Biodiesel, also referred to as fatty acid methyl (or ethyl) ester, is one of the economically most important biofuels today and can be produced on an industrial scale by transesterification of lipids, in which sodium hydroxide and methanol (or ethanol) reacts with a lipid, for example, a triacylglycerol, to produce biodiesel and glycerol.

Feedstocks for industrial-scale production of biodiesel include animal fats, vegetable oils, palm oil, hemp, soy, rapeseed, flax, sunflower, and oleaginous algae. In other approaches, biomass is converted by a microbe into a biofuel precursor, for example, a lipid, that is subsequently extracted and further processed to yield a biofuel. The term "biomass" refers to material produced by growth and/or propagation of a living cell or organism, for example, a microbe. Biomass may contain cells, microbes and/or intracellular contents, for example cellular fatty acids and TAGS, as well as extracellular material. Extracellular material includes, but is not limited to, compounds secreted by a cell, for example, secreted fatty acids or TAGs. Important types of biomass for biofuel production are algal biomass and plant-derived biomass, for example, corn stover and wood fiber. In some embodiments, biomass for biofuel or biofuel precursor production may comprise plant derived sugars, for example, sugarcane or corn derived sugars.

Some aspects of this disclosure relate to the engineering and development of a microbial source of lipids, useful, for example, for economically viable, industrial-scale biodiesel production. The term "lipid" refers to fatty acids and their derivatives. Accordingly, examples of lipids include fatty acids (FA, both saturated and unsaturated); glycerides or glycerolipids, also referred to as acylglycerols (such as monoglycerides (monoacylglycerols), diglycerides (diacylglycerols), triglycerides (triacylglycerols, TAGs, or neutral fats); phosphoglycerides (glycerophospholipids); nonglycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid bodies, lipid droplets, or vacuoles.

Some aspects of this invention relate to engineered microbes for biofuel or biofuel precursor production. In some embodiments, the microbes provided herein are engineered to optimize their lipid metabolism for lipid production. The term "lipid metabolism" refers to the molecular processes that involve the creation or degradation of lipids. Fatty acid synthesis, fatty acid oxidation, fatty acid desaturation, TAG synthesis, TAG storage and TAG degradation are examples of processes that are part of the lipid metabolism of a cell. Accordingly, the term "fatty acid metabolism" refers to all cellular or organismic processes that involve the synthesis, creation, transformation or degradation of fatty acids. Fatty acid synthesis, fatty acid oxidation, TAG synthesis, and TAG degradation are examples of processes are part of the fatty acid metabolism of a cell.

The term "triacylglycerol" (TAG, sometimes also referred to as triglyceride) refers to a molecule comprising a single molecule of glycerol covalently bound to three fatty acid molecules, aliphatic monocarboxylic acids, via ester bonds, one on each of the glycerol molecule's three hydroxyl (OH) groups. Triacylglycerols are highly concentrated stores of metabolic energy because of their reduced, anhydrous nature, and are a suitable feedstock for biodiesel production.

Many cells and organisms store metabolic energy in the form of fatty acids and fatty acid derivatives, such as TAGs. Fatty acids and their derivatives, such as TAGs, provide an ideal form to store metabolic energy. The energy contained in the C—C bonds can be efficiently released by β-oxidation, a reaction formally equivalent to the reverse of fatty acid biosynthesis, but mediated and regulated by different enzymes constituting a different molecular pathway. Microbes can derive fatty acids from external supply, endogenous turnover, and de novo synthesis. Some aspects of this invention relate to the identification of a microbe for biofuel or biofuel precursor production based on the microbe's ability to synthesize and store fatty acids or fatty acid derivatives, such as TAGs, efficiently from an externally supplied carbon source.

Natural fatty acid molecules commonly have an unbranched, aliphatic chain, or tail, of 4 to 28 carbon atoms. Fatty acids are referred to as "saturated", if all carbon atoms of the aliphatic chain are connected via a C—C single bond, or as "unsaturated", if two or more carbon atoms are connected via a C—C double bond. Unsaturated fatty acids play important roles in the regulation of membrane fluidity, cellular activity, metabolism and nuclear events governing gene transcription.

The spectrum of fatty acids in yeast consists mostly of C16 and C18 fatty acids, for example palmitic acid (C16), palmitoleic acid (C16), stearic acid (C18) and oleic acid (C18). Palmitic acid is an unbranched, saturated fatty acid, with an aliphatic chain of 16 carbon atoms (carbon atoms/unsaturated bonds: 16.0). Stearic acid is an unbranched, saturated fatty acid with an aliphatic chain of 18 carbon atoms (18.0). Palmitoleic acid is a monounsaturated fatty acid with an aliphatic chain of 16 carbon atoms (16.1). Oleic acid is a monounsaturated fatty acid with an aliphatic chain of 18 carbon atoms (18.1). Minor fatty acid species in yeast include C14 and C26 fatty acids, which play essential functions in protein modification or as components of sphingolipids and GPI anchors, respectively.

De novo synthesis of fatty acids utilizes substantial amounts of metabolites, acetyl-CoA, ATP and NADPH, and thus competes with other cellular processes that are dependent on these compounds. NADPH is required for two reduction steps in the fatty acid elongation cycle, linking fatty acid synthesis to the metabolic state of the cell and results in fatty acid synthesis being restricted to conditions of high energy load of the cells, indicated by increased ATP/AMP ratio, elevated reduction equivalents and elevated acetyl-CoA pool. Almost all subcellular organelles are involved in fatty acid metabolism, indicating that maintenance of fatty acid homeostasis requires regulation at multiple levels. Lipid synthesis steps that generate metabolites, acetyl-CoA, ATP, or NADPH for lipid biosynthesis are sometimes referred to herein as "push steps" of lipid synthesis. The amplification of a process that increases the production of a metabolites, acetyl-CoA, ATP, or NADPH for lipid synthesis in a cell, for example, by overexpressing a gene product mediating such a metabolite-producing process, is sometimes referred to herein as a "push modification."

Most organisms, including yeast, are able to synthesize fatty acids de novo from a variety of carbon sources. In an initial step, acetyl-CoA is carboxylated by the addition of $CO_2$ to malonyl-CoA, by the enzyme acetyl-CoA carboxylase (ACC; encoded by ACC1 and HFA1 in yeast). Biotin is an essential cofactor in this reaction, and is covalently attached to the ACC apoprotein, by the enzyme biotin:apoprotein ligase (encoded by BPL1/ACC2 in yeast). ACC is a trifunctional enzyme, harboring a biotin carboxyl carrier protein (BCCP) domain, a biotin-carboxylase (BC) domain, and a carboxyl-transferase (CT) domain. In most bacteria, these domains are expressed as individual polypeptides and assembled into a heteromeric complex. In contrast, eukaryotic ACC, including mitochondrial ACC variants (Hfa1 in yeast) harbor these functions on a single polypeptide. Malonyl-CoA produced by ACC serves as a two carbon donor in a cyclic series of reactions catalyzed by fatty acid synthase, FAS, and elongases.

The immediate product of de novo fatty acid synthesis are saturated fatty acids. Saturated fatty acids are known to be the precursors of unsaturated fatty acids in eukaryotes, including yeast. Unsaturated fatty acids are generally produced by desaturation of C—C single bonds in saturated fatty acids by specialized enzymes, called desaturases. The control mechanisms that govern the conversion of saturated fatty acids to unsaturated fatty acids are not well understood. In eukaryotes, unsaturated fatty acids play important roles in the regulation of membrane fluidity, cellular activity, metabolism and nuclear events that govern gene transcription. Typically, about 80% of yeast fatty acids are monounsaturated, meaning that they contain one unsaturated bond in their aliphatic chain.

Fatty acids are potent inhibitors of fatty acid synthesis and the feedback inhibition of fatty acid synthesis by fatty acids is a major obstacle in engineering microbes for oil production. Some aspects of this disclosure are based on the recognition that while push modifications of lipid synthesis are typically unable to override fatty acid-mediated feedback inhibition of lipid synthesis, a combination of a push modification (e.g., ACC1 overexpression) with a pull modification (e.g., DGA1 overexpression), can efficiently bypass the feedback inhibition, thus fully realizing the increased carbon flux to the lipid synthesis pathway, for example, in TGAs stored in a lipid body or vacuole of the cell.

Some aspects of this disclosure provide strategies for engineering microbes for oil production. In some embodiments, such strategies employ genetic engineering of oleaginous microbes, for example, *Y. lipolytica*, to simultaneously amplify a push- and a pull-step of lipid synthesis. As disclosed herein, significant increases of lipid production in oleaginous yeast host cells were achieved using these strategies.

Some aspects of this disclosure are based on the recognition that push-an-pull modifications, for example, simultaneous amplification of metabolic steps that produce metabolites for lipid synthesis pathways and of metabolic steps that sequester synthesis products mediating feedback inhibition of lipid synthesis, result in a significant increase of carbon flux into lipid synthesis pathways as compared to the engineering of push-only or pull-only modifications. Some aspects of this invention relate to the surprising discovery that the overexpression of a DGA1 gene product in an oleaginous microbe, for example, *Yarrowia lipolytica*, results in a marked increase in carbon flux into lipid synthesis pathways, and that simultaneous overexpression of an ACC1 gene product synergizes with DGA1 overexpression, resulting in a push-and-pull modified microbe with greatly enhanced carbon flux properties that is suitable for industrial-scale oil production from a variety of carbon substrates.

The discovery that a balanced modulation of metabolite-generating steps (e.g., production of malonyl-CoA) as well as product-sequestering metabolic steps (e.g., acylation of diacylglycerols to triacylglycerols) in a microbe results in a significant increase of net carbon flux into lipid synthesis has major implication for processes aiming to convert renewable carbon sources into biofuel or biofuel precursors with the help of engineered cells. Based on some aspects of this invention it is now possible to modify the lipid synthesis metabolism of a microbe, for example an oleaginous yeast such as *Y. lipolytica*, in a way that confers highly desirable phenotypes for industrial-scale carbohydrate to biofuel or biofuel precursor conversion, such as remarkable increases in fatty acid synthesis, TAG synthesis, and fatty acid and TAG storage in lipid bodies or vacuoles.

According to some aspects of this invention, modifying the lipid metabolism in a microbe in accordance with methods provided herein, for example by simultaneously overexpressing a gene product mediating a metabolite-generating (push) step and a gene product mediating a product-sequestering (pull) step of lipid synthesis, allows for the generation of a microbe optimized for use in biofuel or biofuel precursor production processes. Some aspects of this invention provide strategies and methods for engineering the fatty acid metabolism in a microbe by simultaneously amplifying a push step and a pull step of lipid biosynthesis, resulting in increased synthesis rate and accumulation of fatty acids and fatty acid derivatives in the microbe.

Some aspects of this invention provide methods that include genetic modifications resulting in the modulation of the expression and/or activity of gene products regulating the lipid metabolism of microbes for biofuel or biofuel precursor production. Such genetic modifications according to some aspects of this invention are targeted to increase carbohydrate to fatty acid and/or TAG conversion in order to optimize the modified microbe for large-scale production of lipids from a carbon source, for example, a carbohydrate source. Some modifications provided according to some aspects of this invention, for example, overexpression, knockout, knock-down, activation and/or inhibition of specific gene products, may be effected alone or in combination, and/or in combination with other modifications known to those of skill in the art. The term "modification" refers to both genetic manipulation, for example, overexpression, knockout, knock-down, activation and/or inhibition of specific gene products, and non-genetic manipulation, for example, manipulation of the growth media, substrate, substrate pretreatment, pH, temperature, conversion process, etc.

A modification of gene expression, also referred to herein as a modulation of gene expression, can be a disruption or inhibition of the natural regulation of expression, an overexpression, an inhibition of expression, or a complete abolishment of expression of a given gene. The insertion of a heterologous promoter upstream of a native gene sequence, for example the native DGA1 or ACC1 gene sequence, or the deletion of regulatory sequences within a promoter, for example regulatory sequences that mediate the feedback inhibition of the DGA1 or ACC1 gene by saturated fatty acids, are examples of a disruption or inhibition of the natural regulation of expression. Strategies for the modulation of gene expression may include genetic alterations, for example by recombinant technologies, such as gene targeting or viral transductions, or non-genetic alterations, for example environmental alterations known to result in the up- or down-regulation of gene expression, or transient delivery of modulators, for example drugs or small RNA molecules to the target cells. Methods for genetic and non-genetic alterations of microbes are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

The term "overexpression", as used herein, refers to an increased level of expression of a given gene product in a given cell, cell type or cell state, as compared to a reference cell, for example, a wild type cell of the same cell type or a cell of the same cell type but lacking a specific modification, for example, a genetic modification. Forced, continuous expression of the DGA1 and/or ACC1 gene in *Y. lipolytica* cells exhibiting concentrations of saturated fatty acids that would inhibit DGA1 or ACC1 gene expression in wild-type cells is an example of gene overexpression.

Some aspects of this invention provide a method for the manipulation of the activity of a diacylglycerol acyltransferase 1 (DGA1) gene product in a microbe for biofuel or biofuel precursor production. The DGA1 gene encodes an acyltransferase that catalyzes the terminal step of triacylglycerol (TAG) formation, acylating diacylglycerol using acyl-CoA as an acyl donor. The result of this acyltransferase reaction are triacylglycerols, which do not exhibit the same inhibitory feedback effect on fatty acid synthesis as fatty acids themselves. TAGs are typically stored in lipid bodies or vacuoles in lipid producing cells. In some embodiments, the manipulation is an overexpression. In some embodiments, the manipulation is effected by contacting a microbe for biofuel or biofuel precursor production with an expression construct comprising a nucleic acid coding for a DGA1 gene product, for example, a DGAT2 protein, operably linked to a heterologous promoter, for example, a constitutive or an inducible promoter. In some embodiments, the nucleic acid coding for a DGA1 gene product comprises the coding sequence of SEQ ID NO: 1. In some embodiments, the DGA1 is *Y. lipolytica* DGA1, for example, *Y. lipolytica* DGA1 comprising the amino acid sequence of SEQ ID NO: 2. In some embodiments, the microbe is *Y. lipolytica*. In some embodiments, manipulation of the activity of a DGA1 gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. DGA1 gene and gene product sequences are well known to those of skill in the art. Exemplary, representative gene and gene product sequences can be found under entry XM_504700 in the NCBI database (www.ncbi.nlm.nih.gov).

Non-limiting examples of suitable sequences of DGA1 nucleic acid and protein sequences are provided below. Additional suitable DGA1 sequences, including sequences from other species, will be apparent to those of skill in the art, and the invention is not limited in this respect.

```
>gi|50554582|ref|XM_504700.1| Yarrowia lipolytica YALI0E32769p (YALI0E32769g)
mRNA, complete cds
                                                             (SEQ ID NO: 1)
ATGACTATCGACTCACAATACTACAAGTCGCGAGACAAAAACGACACGGCACCCAAAATCGCGGGAATCCGATAT
GCCCCGCTATCGACACCATTACTCAACCGATGTGAGACCTTCTCTCTGGTCTGGCACATTTTCAGCATTCCCACT
TTCCTCACAATTTTCATGCTATGCTGCGCAATTCCACTGCTCTGGCCATTTGTGATTGCGTATGTAGTGTACGCT
GTTAAAGACGACTCCCCGTCCAACGGAGGAGTGGTCAAGCGATACTCGCCTATTTCAAGAAACTTCTTCATCTGG
AAGCTCTTTGGCCGCTACTTCCCCATAACTCTGCACAAGACGGTGGATCTGGAGCCCACGCACACATACTACCCT
CTGGACGTCCAGGAGTATCACCTGATTGCTGAGAGATACTGGCCGCAGAACAAGTACCTCCGAGCAATCATCTCC
ACCATCGAGTACTTTCTGCCCGCCTTCATGAAACGGTCTCTTTCTATCAACGAGCAGGAGCAGCCTGCCGAGCGA
GATCCTCTCCTGTCTCCCGTTTCTCCCAGCTCTCCGGGTTCTCAACCTGACAAGTGGATTAACCACGACAGCAGA
TATAGCCGTGGAGAATCATCTGGCTCCAACGGCCACGCCTCGGGCTCCGAACTTAACGGCAACGGCAACAATGGC
ACCACTAACCGACGACCTTTGTCGTCCGCCTCTGCTGGCTCCACTGCATCTGATTCCACGCTTCTTAACGGGTCC
CTCAACTCCTACGCCAACCAGATCATTGGCGAAAACGACCCACAGCTGTCGCCCACAAAACTCAAGCCCACTGGC
AGAAAATACATCTTCGGCTACCACCCCCACGGCATTATCGGCATGGGAGCCTTTGGTGGAATTGCCACCGAGGGA
GCTGGATGGTCCAAGCTCTTTCCGGGCATCCCTGTTTCTCTTATGACTCTCACCAACAACTTCCGAGTGCCTCTC
TACAGAGAGTACCTCATGAGTCTGGGAGTCGCTTCTGTCTCCAAGAAGTCCTGCAAGGCCCTCCTCAAGCGAAAC
CAGTCTATCTGCATTGTCGTTGGTGGAGCACAGGAAAGTCTTCTGGCCAGACCCGGTGTCATGGACCTGGTGCTA
CTCAAGCGAAAGGGTTTTGTTCGACTTGGTATGGAGGTCGGAAATGTCGCCCTTGTTCCCATCATGGCCTTTGGT
GAGAACGACCTCTATGACCAGGTTAGCAACGACAAGTCGTCCAAGCTGTACCGATTCCAGCAGTTTGTCAAGAAC
TTCCTTGGATTCACCCTTCCTTTGATGCATGCCCGAGGCGTCTTCAACTACGATGTCGGTCTTGTCCCCTACAGG
CGACCCGTCAACATTGTGGTTGGTTCCCCCATTGACTTGCCTTATCTCCCACACCCCACCGACGAAGAAGTGTCC
GAATACCACGACCGATACATCGCCGAGCTGCAGCGAATCTACAACGAGCACAAGGATGAATATTTCATCGATTGG
ACCGAGGAGGGCAAAGGAGCCCCAGAGTTCCGAATGATTGAGTAA >gi|50554583|ref|XP_504700.1|YALI0E32769p [Yarrowia lipolytica]
                                                             (SEQ ID NO: 2)
MTIDSQYYKSRDKNDTAPKIAGIRYAPLSTPLLNRCETFSLVWHIFSIPTFLTIFMLCCAIPLLWPFVIAYVVYA
VKDDSPSNGGVVKRYSPISRNFFIWKLFGRYFPITLHKTVDLEPTHTYYPLDVQEYHLIAERYWPQNKYLRAIIS
TIEYFLPAFMKRSLSINEQEQPAERDPLLSPVSPSSPGSQPDKWINHDSRYSRGESSGSNGHASGSELNGNGNNG
```

-continued

```
TTNRRPLSSASAGSTASDSTLLNGSLNSYANQIIGENDPQLSPTKLKPTGRKYIFGYHPHGIIGMGAFGGIATEG
AGWSKLFPGIPVSLMTLTNNFRVPLYREYLMSLGVASVSKKSCKALLKRNQSICIVVGGAQESLLARPGVMDLVL
LKRKGFVRLGMEVGNVALVPIMAFGENDLYDQVSNDKSSKLYRFQQFVKNFLGFTLPLMHARGVFNYDVGLVPYR
RPVNIVVGSPIDLPYLPHPTDEEVSEYHDRYIAELQRIYNEHKDEYFIDWTEEGKGAPEFRMIE
```

Some aspects of this invention provide a method for the manipulation of an acetyl-CoA carboxylase (ACC) gene product in a microbe for biofuel or biofuel precursor production, for example, in *Y. lipolytica*. ACC gene products mediate the conversion of acetyl-CoA, the main C2-precursor in fatty acid synthesis, to malonyl-CoA, which is considered the first committed step in fatty acid synthesis and has been suggested to also be the rate-limiting step in fatty acid synthesis (see Cao Y, Yang J, Xian M, Xu X, Liu W. Increasing unsaturated fatty acid contents in *Escherichia coli* by coexpression of three different genes. Appl Microbiol Biotechnol. 2010). In some embodiments, ACC activity manipulation is ACC overexpression. In some embodiments, the manipulation is effected by contacting a microbe for biofuel or biofuel precursor production with an expression construct comprising a nucleic acid coding for an ACC gene product, for example, an ACC1 protein, operably linked to a heterologous promoter, for example, a constitutive or an inducible promoter. In some embodiments, the nucleic acid coding for an ACC gene product comprises the coding sequence of SEQ ID NO: 3. In some embodiments, the ACC gene product is an ACC1 protein comprising the amino acid sequence of SEQ ID NO: 4. In some embodiments, ACC overexpression in a microbe increases fatty acid synthesis rate and/or confers a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. ACC gene and gene product sequences are well known to those of skill in the art. Exemplary, representative gene and gene product sequences can be found under the entry for GeneIDs: 855750 and 2909424, or under the entry NC_006069 in the NCBI database (www.ncbi.nlm.nih.gov).

Non-limiting examples of suitable sequences of ACC nucleic acid and protein sequences are provided below. Additional suitable ACC sequences, including sequences from other species, will be apparent to those of skill in the art, and the invention is not limited in this respect.

ACC encoding nucleic acid sequence:

(SEQ ID NO: 3)

```
atgcgactgcaattgaggacactaacacgtcggttttcaggtgagtaaacgacggtggccgtggccacgacagc
cgaggcgtcacgatgggccagacgagcacattctcgccgccacaacctcgccagcacaagaaactaacccagtat
ggcttcaggatcttcaacgccagatgtggctccctggtggacccaacattcacaaaggtctcgcctctcattt
ctttggactcaattctgtccacacagccaagccctcaaaagtcaaggagtttgtggcttctcacggaggtcatac
agttatcaacaaggtgagtatttgactgtttagactgtataacaggcggccgcagtgcaacaacgaccaaaaggg
tcgaaaagggtcgaaaacggacacaaaagctggaaaacaagagtgtaatacattcttacacgtccaattgttag
acaaacacggctgttcggtcccaaaaccaccagtatcacctattttccacttgtgtctcggatctgatcataatc
tgatctcaagatgaaatttacgccaccgacatgatattgtgattttcggattctccagaccgagcagattccagc
aataccaccacttgcccaccttcaggcgcctctcggcgcgattcgccactttcccaacgagtgttactaaccca
ggtcctcatcgctaacaacggtattgccgcagtaaaggagatccgttcagtacgaaaatgggcctacgagacctt
tggcgacgagcgagcaatctcgttcaccgtcatggccacccccgaagatctcgctgccaacgccgactacattag
aatggccgatcagtacgtcgaggtgcccggaggaaccaacaacaactacgccaacgtcgagctgattgtcga
cgtggctgagcgattcggcgtcgatgccgtgtgggccggatgggccatgccagtgaaaatccctgctcccga
gtcgctagcggcctctccccgcaagattgtcttcatcggcctccccggagctgccatgagatctctgggagacaa
aatttcttctaccattgtggccagcacgcaaaggtcccgtgtatcccgtggtctggaacggagtggacgaggt
tgtggttgacaagagcaccaacctcgtgtccgtgtccgaggaggtgtacaccaaggctgcaccaccggtcccaa
gcagggtctggagaaggctaagcagattggattccccgtgatgatcaaggcttccgagggaggaggaggaaaggg
tattcgaaaggtgagcgagaggaggacttcgaggctgcttaccaccaggtcgagggagagatccccggctcgcc
catcttcattatgcagcttgcaggcaatgcccggcatttggaggtgcagcttctggctgatcagtacggcaacaa
tatttcactgtttggtcgagattgttcggttcagcgacggcatcaaaagattattgaggaggctcctgtgactgt
ggctggccagcagaccttcactgccatggagaaggctgccgtgcgactcggtaagcttgtcggatatgtctctgc
aggtaccgttgaatatctgtattcccatgaggacgacaagttctacttcttggagctgaatcctcgtcttcaggt
cgaacatcctaccaccgagatggtcaccggtgtcaacctgcccgctgcccagcttcagatcgccatgggtatccc
cctcgatcgaatcaaggacattcgtctctttttacggtgttaaccctcacaccaccactccaattgatttcgactt
ctcgggcgaggatgctgataagacacagcgacgtcccgtcccccgaggtcacaccactgcttgccgaatcacatc
cgaggaccctggagaggggtttcaagccctccggaggtactatgcacgagctcaacttccgatcctcgtccaacgt
gtggggttacttctccgttggtaaccagggaggtatccattcgttctcggattcgcagtttggtcacatcttcgc
cttcggtgagaaccgaagtgcgtctcgaaagcacatggttgttgctttgaaggaactatctattcgaggtgactt
ccgaaccaccgtcgagtacctcatcaagctgctggagacaccggacttcgaggacaacaccatcaccaccggctg
gctggatgagcttatctccaacaagctgactgccgagcgaccccgactcgttcctcgctgttgtttgtggtgctgc
taccaaggcccatcgagcttccgaggactctattgccacctcatggcttcgctagagaagggccaggtccctgc
tcgagacattctcaagaccctttccccgttgacttcatctacgagggccagcggtacaagttcaccgccacccg
gtcgtctggagactcttacacgctgttcatcaacggttctcgatgcgacattggagttagacctcttctgacgg
tggtattctgtgtcttgtaggtgggagatcccacaatgtctactggaaggaggaggttggagccacgcgactgtc
tgttgactccaagacctgccttctcgaggtggagaacgaccccactcagcttcgatctccctctcccggtaagct
ggttaagttcctggtcgagaacggcgaccacgtgcgagccaaccagccctatgccgagattgaggtcatgaagat
gtacatgactctcactgctcaggaggacggtattgtccagctgagcccggttccaccatcgaggctgg
cgacatcctcggtatcttgccctttgatgatccttccaaggtcaagcatgccaagcccttttgagggccagcttcc
cgagcttggaccccccactctcagcggtaacaagcctcatcagcgatacgagcactgccagaacgtgctccataa
cattctgcttggtttcgataaccaggtggtgatgaagtccactcttcaggagatggttggtctgctccgaaacctc
tgagcttccttatctccagtgggctcatcaggtgtcttctctgcacaccgaatgagcgccaagctggatgctac
tcttgctggtctcattgacaaggccaagcagcgaggtggcgagtttcctgccaagcagcttctgcgagccttga
gaaggaggcgagctctggcgaggtcgatgcgctcttccagcaaactcttgctcctctgtttgaccttgctcgaga
gtaccaggacggtcttgctatccacgagcttcaggttgctgcaggccttctgcaggcctactacgactctgaggc
ccggtctgcggacccaacgtacgtgacgaggatgtcattctcaagcttcgagaggagaaccgagattctcttcg
aaaggttgtgatgccccagctgtctcattctcgagtcggagccaagaacaaccttgtgctggcccttctcgatga
```

-continued

```
atacaaggtggccgaccaggctggcaccgactctcctgcctccaacgtgacgttgcaaagtacttgcgacctgt
gctgcgaaagattgtggagctggaatctcgagcttctgccaaggtatctctgaaagcccgagagattctcatcca
gtgcgctctgccctctctaaaggagcgaactgaccagcttgagcacattctgcgatcttctgtcgtcgagtctcg
atacggagaggttggtctggagcaccgaactcccgagccgatattctcaaggaggttgtcgactccaagtacat
tgtctttgatgtgcttgcccagttctttgcccacgatgatccctggatcgtccttgctgccctggagctgtacat
ccgacgagcttgcaaggcctactccatcctggacatcaactaccaccaggactcggacctgcctcccgtcatctc
gtggcgatttagactgcctaccatgtcgtctgctttgtacaactcagtagtgtcttctggctccaaaaccccac
ttccccctcggtgtctcgagctgattccgtctccgacttttcgtacaccgttgagcgagactctgctcccgctcg
aaccggagcgattgttgccgtgcctcatctggatgatctggaggatgctctgactcgtgttctggagaacctgcc
caaacagggcgctggtcttgccatctctgttggtgctagcaacaagagtgccgctgcttctgctcgtgacgctgc
tgctgctgccgcttcatccgttgacactggcctgtccaacatttgcaacgttatgattggtcgggttgatgagtc
tgatgacgacgacactctgattgcccgaatctcccaggtcattgaggactttaaggaggactttgaggcctgttc
tctgcgacgaatcaccttctccttcggcaactcccgaggtacttatcccaagtatttcacgttccgaggccccgc
atacgaggaggacccccactatccgacacgtttgagcctgctctggccttccagctggacgttgaagctggccgtctgtccaa
cttcgacatcaagcctgtccacaccgacaaccgaaacatccacgtgtacgaggcctactggcaagaacgctgcttc
cgacaagcggttcttcacccgaggtatcgtacgacctggtcgtcttcgagagaacatccccacctcggagtatct
catttccgaggctgaccggctcatgagcgatattttggacgtctagaggtgattggaaccaccaactcggatct
caaccacattttcatcaacttctcagccgtctttgctctgaaggccgaggagggtttgaagctgccttttggcggttt
cctggagcgatttggccgacgtctgtggcgacttcgagtcaccggtgccagatccgaatgatggtatccgaccc
cgaaactggctctgctttccctctgcgagcaatgatcaacaacgtctctggttacgttgtgcagtctgagctgta
cgctgaggccaagaacgacaagggccagtggattttcaagtctctgggcaagcccggctccatgcacatgcggtc
tatcaacactccctacccccaccaaggagtggctgcagcccaagcggtacaaggcccatctgatgggtaccaccta
ctgctatgacttccccgagctgttccgacagtccattgagtcggactggaagaagtatgacggcaaggctcccga
cgatctcatgacttgcaacgagctgattctcgatgaggactctggcgagctgcaggaggtgaaccgagagcccgg
cgccaacaacgtcggtatggttgcgtggaagtttgaggccaagaccccgagtaccctcgaggccgatctttcat
cgtggtggccaacgatatcaccttccagattggttcgtttggccctgctgaccgccagttcttcttcaaggtgac
ggagctggctcgaaagctcggtattcctcgaatctatctgtctgccaactctggtgctcgaatcggcattgctga
cgagctcgttggcaagtacaaggttgcgtggaacgacgagactgaccctccaagggcttcaagtacctttactt
cacccctgagtctcttgccaccctcaagcccgacactgttgtcaccactgagattgaggaggagggtcccaacgg
cgtggagaagcgtcatgtgatcgactacattgtcggagagaaggacggtctcggagtcgagtgtctgcggggctc
tggtcttcattgcaggcgccacttctcgagcctacaaggatatcttcactctcactcttgtcacctgtcgatccgt
tggtatcggtgcttaccttgttcgtcttggtcaacgagccatccagattgagggccagcccatcattctcactgg
tgcccccgccatcaacaagctgcttggtcgagaggtctactcttccaacttgcagcttggtggtactcagatcat
gtacaacaacggtgtgtctcatctgactgcccgagatgatctcaacggtgtccacaagatcatgcagtggctgtc
atacatccctgcttctcgaggtcttccagtgcctgttctccctcacaagaccgatgtgtgggatcgagacgtgac
gttccagcctgtccgaggcgagcagtacgatgttagatggcttatttctggccgaactctcgaggatggtgcttt
cgagtctggtctctttgacaaggactcttttccaggagactctgtctggctgggcaagggtgttgttgttggtcg
agctcgtcttggcggcattcccttcggtgtcattggtgtcgagactgcgaccgtcgacaatactaccctgccga
tcccgccaacccggactctattgagatgagcacctctgaagccggccccaggtttggtacccaactcggcctcaa
gacctctcaggccatcaacgacttcaaccatggtgaggcgcttcctctcatgattcttgctaactggcgaggctt
ttctggtggtcagcgagacactgtacaatgaggttctcaagtacggatctttcattgttgatgctctggttgacta
caagcagcccatcatggtgtacatccctccaccggtgagctgcgaggtggttcttgggttgtggttgaccccac
catcaactcggacatgatggagatgtacgctgacgtcgagctcgaggctgtggagcccgagggaatggt
cggtatcaagtaccgacgagacaagctactgacaccatggctcgtctggatcccgagtactcctctctcaagaa
gcagcttgaggagtctcccgattctgaggagctcaaggtcaagctcagcgtgcgagagaagtctctcatgcccat
ctaccagcagatctccgtgcagtttgccgacttgcatgaccgagctggccgaatggaggccaagggtgtcattcg
tgaggctcttgtgtggaaggatgctcgtcgattcttcttctgcgaatccgacgacgattagtcgaggagtacct
cattaccaagatcaatagcattctgccctcttgcactcggcttgagtgtctggctcgaatcaagtcgtggaagcc
tgccactcttgatcagggctctgaccggggtgttgccgagtggtttgacgagaactctgatgccgtctctgctcg
actcagcgagctcaagaaggacgcttctgcccagtcgtttgcttctcaactgagaaaggaccgacagggtactct
ccagggcatgaagcaggctctcgcttctctttctgaggctgagcgggctgagctgctcaaggggttgtga
```

>gi|50548503|ref|XP_501721.1| YALI0C11407p [Yarrowia lipolytica]
(SEQ ID NO: 4)

MRLQLRTLTRRFFSMASGSSTPDVAPLVDPNIHKGLASHFFGLNSVHTAKPSKVKEFVASHGGHTVINKVLIANN
GIAAVKEIRSVRKWAYETFGDERAISFTVMATPEDLAANADYIREMADQYVEVPGGTNNNNYANVELIVDVAERFG
VDAVWAGWGHASENPLLPESLAASPRKIVFIGPPGAAMRSLGDKISSTIVAQHAKVPCIPWSGTGVDEVVVDKST
NLVSVSEEVYTKGCTTGPKQGLEKAKQIGFPVMIKASEGGGGKGIRKVEREEDFEAAYHQVEGEIPGSPIFIMQL
AGNARHLEVQLLADQYGNNISLFGRDCSVQRRHQKIIEEAPVTVAGQQTFTAMEKAAVRLGKLVGYVSAGTVEYL
YSHEDDKFYFLELNPRLQVEHPTTEMVTGVNLPAAQLQIAMGIPLDRIKDIRLFYGVNPHTTTPIDFDFSGEDAD
KTQRRPVPRGHTTACRITSEDPGEGFKPSGGTMHELNFRSSSNVWGYFSVGNQGGIHSFSDSQFGHIFAFGENRS
ASRKHMVVALKELSIRGDFRTTVEYLIKLLETPDFEDNTITTGWLDELISNKLTAERPDSFLAVVCGAATKAHRA
SEDSIATYMASLEKGQVPARDILKTLFPVDFIYEGQRYKFTATRSSEDSYTLFINGSRCDIGVRPLSDGGILCLV
GGRSHNVYWKEEVGATRLSVDSKTCLLEVENDPTQLRSPSPGKLVKFLVENGDHVRANQPYAEIEVMKMYMTLTA
QEDGIVQLMKQPGSTIEAGDILGILALDDPSKVKHAKPFEGQLPELGPPTLSGNKPHQRYEHCQNVLHNILLGFD
NQVVMKSTLQEMVGLLRNPELPYLQWAHQVSSLHTRMSAKLDATLAGLIDKAKQRGGEFPAKQLLRALEKEASSG
EVDALFQQTLAPLFDLAREYQDGLAIHELQVAAGLLQAYYDSEARFCGPNVRDEDVILKLREEENRDSLRKVVMAQ
LSHSRVGAKNNLVLALLDEYKVADQAGTDSPASNVHVAKYLRPVLRKIVELESRASAKVSLKAREILIQCALPSL
KERTDQLEHILRSSVVESRYGEVGLEHRTPRADILKEVVDSKYIVFDVLAQFFAHDDPWIVLAALELYIRRACKA
YSILDINYHQDSDLPPVISWRFRLPTMSSALYNSVVSSGSKTPTSPSVSRADSVSDFSYTVERDSAPARTGAIVA
VPHLDDLEDALTRVLENLPKRGAGLAISVGASNKSAAASARDAAAAAASSVDTGLSNICNVMIGRVDESDDDDTL
IARISQVIEDFKEDFEACSLRRITFSFGNSRGTYPKYFTFRGPAYEEDPTIRHIEPALAFQLELARLSNFDIKPV
HTDNRNIHVYEATGKNAASDKRFFTRGIVRPGRLRENIPTSEYLISEADRLMSDILDALEVIGTTNSDLNHIFIN
FSAVFALKPEEVEAAFGGFLERFGRRLWRLRVTGAEIRMMVSDPETGSAFPLRAMINNVSGYVVQSELYAEAKND
KGQWIFKSLGKPGSMHMRSINTPYPTKEWLQPKRYKAHLMGTTYCYDFPELFRQSIESDWKKYDGKAPDDLMTCN
ELILDEDSGELQEVNREPGANNVGMVAWKFEAKTPEYPRGRSFIVVANDITFQIGSFGPAEDQFFFKVTELARKL
GIPRIYLSANSGARIGIADELVGKYKVAWNDETDPSKGFKYLYFTPESLATLKPDTVVTTEIEEEGPNGVEKRHV
IDYIVGEKDGLGVECLRGSGLIAGATSRAYKDIFTLTLVTCRSVGIGAYLVRLGQRAIQIEGQPIILTGAPAINK
LLGREVYSSNLQLGGTQIMYNNGVSHLTARDDLNGVHKIMQWLSYIPASRGLPVPVLPHKTDVWDRDVTFQPVRG
EQYDVRWLISGRTLEDGAFESGLFDKDSFQETLSGWAKGVVVGRARLGGIPFGVIGVETATVDNTTPADPANPDS
IEMSTSEAGQVWYPNSAFKTSQAINDFNHGEALPLMILANWRGFSGGQRDMYNEVLKYGSFIVDALVDYKQPIMV

-continued

```
YIPPTGELRGGSWVVVDPTINSDMMEMYADVESRGGVLEPEGMVGIKYRRDKLLDTMARLDPEYSSLKKQLEESP
DSEELKVKLSVREKSLMPIYQQISVQFADLHDRAGRMEAKGVIREALVWKDARRFFFWRIRRRLVEEYLITKINS
ILPSCTRLECLARIKSWKPATLDQGSDRGVAEWFDENSDAVSARLSELKKDASAQSFASQLRKDRQGTLQGMKQA
LASLSEAERAELLKGL.
```

Some aspects of this invention provide a method for the manipulation of the activity of a stearoyl-CoA-desaturase (SCD) in a microbe for biofuel or biofuel precursor production. SCD is a Δ9 desaturase that inserts a double bond between C9 and C10 of stearic acid coupled to CoA, a key Non-limiting examples of suitable sequences of SCD nucleic acid and protein sequences are provided below. Additional suitable SCD sequences, including sequences from other species, will be apparent to those of skill in the art, and the invention is not limited in this respect.

```
>gi|50548052|ref|XM_501496.11 Yarrowia lipolytica YALI0C05951p (YALI0C05951g)
mRNA, complete cds
                                                                    (SEQ ID NO: 5)
ATGGTGAAAAACGTGGACCAAGTGGATCTCTCGCAGGTCGACACCATTGCCTCCGGCCGAGATGTCAACTACAAG
GTCAAGTACACCTCCGGCGTTAAGATGAGCCAGGGCGCCTACGACGACAAGGGCCGCCACATTTCCGAGCAGCCC
TTCACCTGGGCCAACTGGCACCAGCACATCAACTGGCTCAACTTCATTCTGGTGATTGCGCTGCCTCTGTCGTCC
TTTGCTGCCGCTCCCTTCGTCTCCTTCAACTGGAAGACCGCCGCGTTTGCTGTCGGCTATTACATGTGCACCGGT
CTCGGTATCACCGCCGGCTACCACCGAATGTGGGCCCATCGAGCCTACAAGGCCGCTCTGCCCGTTCGAATCATC
CTTGCTCTGTTTGGAGGAGGAGCTGTCGAGGGCTCCATCCGATGGTGGGCCTCGTCTCACCGAGTCCACCACCGA
TGGACCGACTCCAACAAGGACCCTTACGACGCCCGAAAGGGATTCTGGTTCTCCCACTTTGGCTGGATGCTCTT
GTGCCCAACCCCAAGAACAAGGGCCGAACTGACATTTCTGACCTCAACAACGACTGGGTTGTCCGACTCCAGCAC
AAGTACTACGTTTACGTTCTCGTCTTCATGGCCATTGTTCTGCCCACCCTCGTCTGTGGCTTTGGCTGGGGCGAC
TGGAAGGGAGGTCTTGTCTACGCCGGTATCATGCGATACACCTTTGTGCAGCAGGTGACTTTCTGTGTCAACTCC
CTTGCCCACTGGATTGGAGAGCAGCCCTTCGACGACCGACGAACTCCCCGAGACCACGCTCTTACCGCCCTGGTC
ACCTTTGGAGAGGGCTACCACAACTTCCACCACGAGTTCCCCTCGGACTACCGAAACGCCCTCATCTGGTACCAG
TACGACCCCACCAAGTGGCTCATCTGGACCCTCAAGCAGGTTGGTCTCGCCTGGGACCTCCAGACCTTCTCCCAG
AACGCCATCGAGCAGGGTCTCGTGCAGCAGCGACAGAAGAAGCTGGACAAGTGGCGAAACAACCTCAACTGGGGT
ATCCCCATTGAGCAGCTGCCCTGTCATTGAGTTTGAGGAGTTCCAAGAGCAGGCCAAGACCCGAGATCTGGTTCTC
ATTTCTGGCATTGTCCACGACGTGTCTGCCTTTGTCGAGCACCACCCTGGTGGAAAGGCCCTCATTATGAGCGCC
GTCGGCAAGGACGGTACCGCTGTCTTCAACGGAGGTGTCTACCGACACTCCAACGCTGGCCACAACCTGCTTGCC
ACCATGCGAGTTTCGGTCATTCGAGGCGGCATGGAGGTTGAGGTGTGGAAGACTGCCCAGAACGAAAGAAGGAC
CAGAACATTGTCTCCGATGAGAGTGGAAACCGAATCCACCGAGCTGGTCTCCAGGCCACCCGGGTCGAGAACCCC
GGTATGTCTGGCATGGCTGCTTAG >gi|50548053|ref|XP_501496.1| YALI0C05951p [Yarrowia lipolytica]
                                                                    (SEQ ID NO: 6)
MVKNVDQVDLSQVDTIASGRDVNYKVKYTSGVKMSQGAYDDKGRHISEQPFTWANWHQHINWLNFILVIALPLSS
FAAAPFVSFNWKTAAFAVGYYMCTGLGITAGYHRMWAHRAYKAALPVRIILALFGGGAVEGSIRWWASSHRVHHR
WTDSNKDPYDARKGFWFSHFGWMLLVPNPKNKGRTDISDLNNDWVVRLQHKYYVYVLVFMAIVLPTLVCGFGWGD
WKGGLVYAGIMRYTFVQQVTFCVNSLAHWIGEQPFDDRRTPRDHALTALVTFGEGYHNFHHEFPSDYRNALIWYQ
YDPTKWLIWTLKQVGLAWDLQTFSQNAIEQGLVQQRQKKLDKWRNNLNWGIPIEQLPVIEFEEFQEQAKTRDLVL
ISGIVHDVSAFVEHHPGGKALIMSAVGKDGTAVFNGGVYRHSNAGHNLLATMRVSVIRGGMEVEVWKTAQNEKKD
QNIVSDESGNRIHRAGLQATRVENPGMSGMAA
``` step in the generation of desaturated fatty acids and their derivatives, as described in more detail elsewhere herein. In some embodiments, the manipulation is an overexpression. In some embodiments, the manipulation is effected by contacting a microbe for biofuel or biofuel precursor production with an expression construct comprising a nucleic acid coding for a SCD gene product, for example, a SCD protein, operably linked to a heterologous promoter, for example, a constitutive or an inducible promoter. In some embodiments, the nucleic acid coding for an SCD gene product comprises the coding sequence of SEQ ID NO: 5. In some embodiments, the SCD is Y. lipolytica SCD, for example, Y. lipolytica SCD comprising the amino acid sequence of SEQ ID NO: 6. In some embodiments, the microbe is Y. lipolytica. In some embodiments, manipulation of the activity of a SCD in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. Stearoyl-CoA Desaturase gene and gene product sequences are well known to those of skill in the art. Exemplary, representative gene and gene product sequences can be found under the entry for GeneID: 852825 in the NCBI database (www.ncbi.nlm.nih.gov).

Some aspects of this invention provide a method for the manipulation of the activity of an ATP-citrate lyase (ACL) in a microbe for biofuel or biofuel precursor production. ACL provides cytosolic acetyl-CoA by cleaving citrate which is shuttled out of the mitochondria as a product of the TCA cycle. Cleaving citrate into oxaloacetate and acetyl-CoA, ACL gene products provide an acetyl-CoA substrate for ACC, which then mediates the conversion of acetyl-CoA, the main C2-precursor in fatty acid synthesis, to malonyl-CoA, which is considered the first committed step in fatty acid synthesis, as described in more detail elsewhere herein. In some embodiments, an ACL gene product is a protein composed of two subunits encoded by separate genes. In some embodiments, an ACL gene product is composed of two subunits encoded by the same gene. In some embodiments, the manipulation is an overexpression. In some embodiments, the manipulation is effected by contacting a microbe for biofuel or biofuel precursor production with an expression construct comprising a nucleic acid coding for an ACL gene product, for example, an ACL protein, operably linked to a heterologous promoter, for example, a constitutive or an inducible promoter. In some embodiments, the nucleic acid coding for an ACL gene product comprises the coding sequences of SEQ ID NO: 7 and SEQ ID NO: 9. In some embodiments, the ACL is Y. lipolytica ACL, for example, Y. lipolytica ACL comprising the amino acid sequences of SEQ ID NO: 8 and SEQ ID NO: 10. In some embodiments, the microbe is *Y. lipolytica*. In some embodiments, manipulation of the activity of a ACL in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. ATP-citrate lyase gene and gene product sequences are well known to those of skill in the art. Exemplary, representative gene and gene product sequences can be found under the entry for GeneID: 2912101 and 2910381 in the NCBI database (www.ncbi.nlm.nih.gov).

Non-limiting examples of suitable sequences of ACL nucleic acid and protein sequences are provided below. Additional suitable ACL sequences, including sequences from other species, will be apparent to those of skill in the art, and the invention is not limited in this respect.

```
ATP Citrate Lyase (Yarrowia lipolytica) subunit 1, ACL1 DNA
YALI0E34793g
XM_504787
                                                        (SEQ ID NO: 7)
atgtctgccaacgagaacatctcccgattcgacgccctgtgggcaaggagcaccccgcctacgagctcttccat
aaccacacacgatctttcgtctatggtctccagcctcgagcctgccagggtatgctggacttcgacttcatctgt
aagcgagagaaccccctccgtggccggtgtcatctatcccttcggcggccagttcgtcaccaagatgtactgggggc
accaaggagacttcttctccctgtctaccagcaggtcgagaaggccgctgccaagcaccccgaggtcgatgtcgtg
gtcaactttgcctcctctcgatccgtctactcctctaccatggagctgctcgagtaccccagttccgaaccatc
gccattattgccgagggtgtccccgagcgacgagcccgagagatcctccacaaggcccagaagaagggtgacc
atcattggtcccgctaccgtcggaggtatcaagcccggttgcttcaaggttggaaacaccggaggtatgatggac
aacattgtcgcctccaagctctaccgaccggctccgttgcctacgtctccaagtccggaggaatgtccaacgag
ctgaacaacattatctctcacaccaccgacggtgtctacgagggtattgctattggtggtgaccgataccctggt
actaccttcattgaccatatctgcgatacgaggccgacccaagtgtaagatcatcgtcctccttggtgaggtt
ggtggtgttgaggagtaccgagtcatcgaggctgttaagaacggccagatcaagaagcccatcgtcgcttgggcc
attggtacttgtgcctccatgttcaagactgaggttcagttcggccacgccggctccatggccaactccgacctg
gagactgccaaggctaagaacgccgccatgaagtctgctggcttctacgtccccgatccttcgaggacatgccc
gaggtccttgccgagctctacgagaagatggtcgccaagggcgagctgtctcgaatctctgagcctgaggtcccc
aagatccccattgactactcttgggccaggagcttggtcttatccgaaagcccgctgctttcatctccactatt
tccgatgaccgaggccaggagcttctgtacgctggcatgcccatttccgaggttttcaaggaggacattggtatc
ggcggtgtcatgtctctgctgtggttccgacgacgactccccgactacgcctccaagtttcttgagatggttctc
atgcttactgctgaccacggtcccgccgtatccggtgccatgaacaccattatcaccacccgagctggtaaggat
ctcatttcttccctggttgctggtctcctgaccattggtaccgattcggaggtgctcttgacggtgctgccacc
gagttcaccactgcctacgacaagggtctgtcccccgacagttcgttgataccatgcgaaagcagaacaagctg
attcctggtattggccatcgagtcaagtctcgaaacaaccccgatttccgagtcgagcttgtcaaggactttgtt
aagaagaacttccctccacccagctgctcgactacgcccttgctgtcgaggaggtcaccacctccaagaaggac
aacctgattctgaacgttgacggtgctattgctgtttcttttgtcgatctcatgcgatcttgcggtgcctttact
gtggaggagactgaggactacctcaagaacggtgttctcaacggtctgttcgttctcggtcgatccattggtctc
attgccaccatctcgatcagaagcgactcaagaccggtctgtaccgacatccttgggacgatatcacctacctg
gttggccaggaggctatccagaagaagcgagtcgagatcagcgccggcgacgttccaaggccaagactcgatca
tag ATP Citrate Lyase (Yarrowia lipolytica) subunit 1, ACL1 Protein
YALI0E34793p
XP_504787
                                                        (SEQ ID NO: 8)
MSANENISRFDAPVGKEHPAYELFHNHTRSEVYGLQPRACQGMLDFDFICKRENPSVAGVIYPEGGQFVTKMYWG
TKETLLPVYQQVEKAAAKHPEVDVVVNFASSRSVYSSTMELLEYPQFRTIAIIAEGVPERRAREILHKAQKKGVT
IIGPATVGGIKPGCFKVGNTGGMMDNIVASKLYRPGSVAYVSKSGGMSNELNNIISHTTDGVYEGIAIGGDRYPG
TTFIDHILRYEADPKCKIIVLLGEVGGVEEYRVIEAVKNGQIKKPIVAWAIGTCASMFKTEVQFGHAGSMANSDL
ETAKAKNAAMKSAGFYVPDTFEDMPEVLAELYEKMVAKGELSRISEPEVPKIPIDYSWAQELGLIRKPAAFISTI
SDDRGQELLYAGMPISEVFKEDIGIGGVMSLLWERRRLPDYASKFLEMVLMLTADHGPAVSGAMNTIITTRAGKD
LISSLVAGLLTIGTREGGALDGAATEFTTAYDKGLSPRQFVDTMRKQNKLIPGIGHRVKSRNNPDFRVELVKDEV
KKNFPSTQLLDYALAVEEVTTSKKDNLILNVDGAIAVSFVDLMRSCGAFTVEETEDYLKNGVLNGLFVLGRSIGL
IAHHLDQKRLKTGLYRHPWDDITYLVGQEAIQKKRVEISAGDVSKAKTRS ATP Citrate lyase (Yarrowia lipolytica) subunit 2, ACL2 DNA
YALI0D24431g
XM_503231
                                                        (SEQ ID NO: 9)
atgtcagcgaaatccattcacgaggccgacggcaaggccctgctcgcacactttctgtccaaggcgcccgtgtgg
gccgagcagcagcccatcaacacgtttgaaatgggcacacccaagctggcgtctctgacgttcgaggacggcgtg
gcccccgacagatcttcgccgccgctgaaaagacctaccccctggctgctggagtccggcgccaagtttgtggcc
aagcccgaccagctcatcaagcgacgaggcaaggccggcctgctggtactcaacaagtcgtgggaggagtgcaag
ccctggatcgccgagcgggccgccaagcccatcaacgtggagggcattgacggagtgctgcgaacgttcctggtc
gagcccctttgtgccccacgaccagaagcacgagtactacatcaacatccactccgtgcgagagggcgactggatc
ctcttctaccacgagggaggagtcgacgtcggcgacgtggacgccaaggccgccaagatcctcatccccgttgac
attgagaacgagtaccccctccaacgccacgctcaccaaggagctgctggcacacgtgcccgaggaccagcaccag
accctgctcgacttcatcaaccggctctacgccgtctacgtcgatctgcagtttacgtatctggagatcaaccccc
ctggtcgtgatcccaccgcccagggcgtcgaggtccactacctggatcttgccggcaagctcgaccagaccgca
gagtttgagtgcggccccaagtgggctgctgcgcggtccccgccgctctgggccaggtcgtcaccattgacgcc
ggctccaccaaggtgtccatcgacgccggccccgcatggtcttcccgctccttcggtcgagagctgtccaag
gaggaggcgtacattgcggagctcgattccaagacccggagcttctctgaagctgactgactgttctcaatgccaagggc
cgaatctggaccttgtggctggtggaggagcctccgtcgtctacgccgacgccattgcgtctgccggctttgct
gacgagctcgccaactacgcgagtactctggcgctccaacgagacccagacctacgagtacgccaaaaccgta
ctggatctcatgacccggggcgacgctcacccgagggcaaggtactgttcattggcggaggaatcgccaacttc
acccaggttggatccaccttcaagggcatcatccgggccttccgggactaccagtcttctctgcacaaccacaag
gtgaagatttacgtgcgacgaggcggtcccaactggcaggagggtctgcggttgatcaagtcggctggcgacgag
```

-continued

```
ctgaatctgcccatggagatttacggcccgacatgcacgtgtcgggtattgttcctttggctctgcttggaaag
cggcccaagaatgtcaagccttttggcaccggaccttctactgaggcttccactcctctcggagtttaa
```

ATP Citrate lyase (*Yarrowia lipolytica*) subunit 2, ACL2 Protein
YALI0D24431p
XP_503231

(SEQ ID NO: 10)

```
MSAKSIHEADGKALLAHFLSKAPVWAEQQPINTFEMGTPKLASLTFEDGVAPEQIFAAAEKTYPWLLESGAKFVA
KPDQLIKRRGKAGLLVLNKSWEECKPWIAERAAKPINVEGIDGVLRTFLVEPFVPHDQKHEYYINIHSVREGDWI
LFYHEGGVDVGDVDAKAAKILIPVDIENEYPSNATLTKELLAHVPEDQHQTLLDFINRLYAVYVDLQFTYLEINP
LVVIPTAQGVEVHYLDLAGKLDQTAEFECGPKWAAARSPAALGQVVTIDAGSTKVSIDAGPAMVFPAPFGRELSK
EEAYIAELDSKTGASLKLTVLNAKGRINTLVAGGGASVVYADAIASAGFADELANYGEYSGAPNETQTYEYAKTV
LDLMTRGDAHPEGKVLFIGGGIANFTQVGSTFKGIIRAFRDYQSSLHNHKVKIYVRRGGPNWQEGLRLIKSAGDE
LNLPMEIYGPDMHVSGIVPLALLGKRPKNVKPFGTGPSTEASTPLGV
```

Some aspects of this invention provide oleaginous microbes for oil production comprising any of the modifications described herein, for example, a DGA1 modification as described herein, an ACC1 modification as described herein, and/or an SCD modification as described herein. In some embodiments, a modified oleaginous microbe is provided that comprises a push modification as described herein and a pull modification as described herein. In some embodiments, the push modification comprises overexpression of an ACC1 gene product. In some embodiments, the pull modification comprises overexpression of a DGA1 and/or an SCD gene product.

Some aspects of this invention provide nucleic acids coding for a gene product conferring a required and/or desired phenotype for biofuel or biofuel precursor production to a microbe, for example, *Y. lipolytica*. In some embodiments, the nucleic acid is a nucleic acid derived from *Y. lipolytica*. In some embodiments, the nucleic acid encodes a DGA1 gene product, for example, a DGA1 protein. In some embodiments, the nucleic acid encodes an ACC1 gene product, for example, an ACC1 protein. In some embodiments, the nucleic acid encodes a desaturase, for example a Δ9 desaturase. In some embodiments, the nucleic acid encodes *Y. lipolytica* Δ9 desaturase (SCD). In some embodiments, a nucleic acid is provided that encodes a combination of gene products, for example in multiple cistrons, comprising a gene product the overexpression of which represents a push modification of lipid biosynthesis (e.g., an ACC1 gene product), and a gene product the overexpression of which represents a pull modification of lipid biosynthesis (e.g., a DGA1 and/or SCD gene product).

The term "nucleic acid" refers to a molecule comprising multiple linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) and yeast artificial chromosomes (YACs) can also be used in accordance with some aspects of this invention.

Some aspects of this invention relate to the use of nucleic acid derivatives. The use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects of this invention may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives according to some aspects of this invention may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine.

In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Some aspects of this invention relate to nucleic acids encoding a gene product conferring a required or desirable phenotype to a microbe for biofuel or biofuel precursor production which are linked to a promoter or other transcription activating element. In some embodiments, the nucleic acid encoding the gene product and linked to a promoter is comprised in an expression vector or expression construct. As used herein, the terms "expression vector" or "expression construct" refer to a nucleic acid construct, generated recombinantly or synthetically, with a series of specified nucleic acid elements that permit transcription of a particular nucleic acid in a host microbe, for example, an oleaginous yeast. In some embodiments, the expression vector may be part of a plasmid, virus, or nucleic acid fragment. In some embodiments, the expression vector includes the coding nucleic acid to be transcribed operably linked to a promoter. A promoter is a nucleic acid element that facilitates transcription of a nucleic acid to be transcribed. A promoter is typically located on the same strand and upstream (or 5') of the nucleic acid sequence the transcription of which it controls. In some embodiments, the expression vector includes the coding nucleic acid to be transcribed operably linked to a heterologous promoter. A heterologous promoter is a promoter not naturally operably linked to a given nucleic acid sequence. For example, the DGA1 gene in Y. lipolytica is naturally operably linked to the Y. lipolytica DGA1 gene promoter. Any promoter other than the wildtype Y. lipolytica DGA1 gene promoter operably linked to the DGA1 gene, or parts thereof, for example in an expression construct, would, therefore, be a heterologous promoter in this context. For example, a TEF1 promoter linked to a nucleic acid encoding a DGA1 gene product is a heterologous promoter in the DGA1 context.

In some embodiments, the expression vector includes a coding nucleic acid, for example, a nucleic acid encoding a DGA1, ACC1, and/or SCD gene product, operably linked to a constitutive promoter. The term "constitutive promoter" refers to a promoter that allows for continual transcription of its associated gene. In some embodiments, the expression vector includes a coding nucleic acid, for example, a nucleic acid encoding a DGA1, ACC1, and/or SCD gene product, operably linked to an inducible promoter. The term "inducible promoter", interchangeably used herein with the term "conditional promoter", refers to a promoter that allows for transcription of its associated gene only in the presence or absence of biotic or abiotic factors. Drug-inducible promoters, for example tetracycline/doxycycline inducible promoters, tamoxifen-inducible promoters, as well as promoters that depend on a recombination event in order to be active, for example the cre-mediated recombination of loxP sites, are examples of inducible promoters that are well known in the art.

Some aspects of this disclosure relate to the surprising discovery that overexpression of a given gene product from a heterologous promoter in oleaginous microbes can be significantly enhanced by including an intron in the respective expression construct. Some aspects of this disclosure provide an intron-enhanced constitutive promoter for gene overexpression in oleaginous microbes and expression constructs and vectors comprising this intron-enhanced promoter. In some embodiments, an intron-enhanced TEF promoter is provided, that comprises a TEF promoter sequence, a transcription start site, an intronic sequence downstream of the transcription start site, and a coding nucleic acid sequence, for example, a nucleic acid sequence encoding a DGA1, ACC1 and/or SCD gene product. In some embodiments, the intron is positioned downstream of the translation start site, yet within the open reading frame of the gene sequence, e.g., after the start codon, but before the termination site of the nucleic acid sequence encoding the gene product. In some embodiments, the intron is positioned immediately downstream of the translation start site, e.g., an ATG start codon, yet upstream of the remainder of the coding sequence. For illustration purposes, a non-limiting, exemplary structure of an intron-enhanced expression construct is provided as follows:

5'—TEF promoter—transcription start site—intron—DGA1 coding sequence—3'. Another non-limiting, exemplary structure of an intron-enhanced expression construct is provided as follows:

5'—TEF promoter—transcription start site—start codon—intron—DGA1 coding sequence—stop codon—3'. Expression constructs for ACC1 and SCD gene products would have the DGA1 coding sequence substituted for an ACC or SCD coding sequence, respectively.

Suitable TEF promoter sequences as well as suitable intron sequences will be apparent to those of skill in the art. Some intron-less TEF promoter sequences are disclosed, for example, in U.S. Pat. No. 6,265,185. Some exemplary, representative sequences are provided below. However, it will be understood that the invention is not limited in this respect.

Exemplary TEF promoter sequence:

(SEQ ID NO: 11)
agagaccgggttggcggcgcatttgtgtcccaaaaaacagccccaat tgccccaattgaccccaaattgacccagtagcgggcccaacccggc gagagccccttctccccacatatcaaacctccccggttcccacac ttgccgttaagggcgtagggtactgcagtctggaatctacgcttgtt cagactttgtactagtttctttgtctggccatccgggtaacccatgc cggacgcaaaatagactactgaaaattttttgctttgtggttggga ctttagccaagggtataaaagaccaccgtccccgaattacctttcct cttcttttctctctctccttgtcaactcacacccgaaatcgttaagc atttccttctgagtataagaatcattcaaa Exemplary intron sequence:

(SEQ ID NO: 12)
gtgagtttcagaggcagcagcaattgccacgggctttgagcacacgg ccgggtgtggtcccattcccatcgacacaagacgccacgtcatccga ccagcacttttgcagtactaaccgcag Exemplary TEF promoter-intron sequence comprising a start codon (ATG) between the promoter and the intron sequences:

(SEQ ID NO: 13)
agagaccgggttggcggcgcatttgtgtcccaaaaaacagccccaat tgccccaattgaccccaaattgacccagtagcgggcccaacccggc

```
-continued
gagagcccccttctccccacatatcaaacctccccggttcccacac ttgccgttaagggcgtagggtactgcagtctggaatctacgcttgtt cagactttgtactagtttctttgtctggccatccgggtaacccatgc cggacgcaaaatagactactgaaaatttttttgctttgtggttggga ctttagccaagggtataaaagaccaccgtccccgaattacctttcct cttcttttctctctctccttgtcaactcacacccgaaatcgttaagc atttccttctgagtataagaatcattcaaaATGgtgagtttcagagg cagcagcaattgccacgggctttgagcacacggccgggtgtggtccc attcccatcgacacaagacgccacgtcatccgaccagcactttttgc agtactaaccgcag
```

Methods to deliver expression vectors or expression constructs into microbes, for example, into yeast cells, are well known to those of skill in the art. Nucleic acids, including expression vectors, can be delivered to prokaryotic and eukaryotic microbes by various methods well known to those of skill in the relevant biological arts. Methods for the delivery of nucleic acids to a microbe in accordance with some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising a combination of DGA1, ACC1, and/or SCD encoding nucleic acid sequences, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

In some embodiments, the native promoter of a gene encoding a gene product conferring a required or desirable phenotype to a microbe, for example, the native DGA1, ACC1, or SCD promoter, is modified in the microbe to alter the regulation of its transcriptional activity. In some embodiment, the modified promoter exhibits an increased transcriptional activity as compared to its unmodified counterpart. The term "modified promoter", as used herein, refers to a promoter the nucleotide sequence of which has been artificially altered. Nucleotide deletion(s), insertion(s) or mutation(s), alone or in combination, are examples of such artificial alterations. Artificial promoter alterations can be effected in a targeted fashion, for example by homologous recombination approaches, such as gene targeting, knockout, knock in, site-directed mutagenesis, or artificial zinc finger nuclease-mediated strategies. Alternatively, such alterations may be effected by a random or quasi-random event, such as irradiation or non-targeted nucleotide integration and subsequent selection. Promoter modifications, in general, are fashioned in order to modulate the transcriptional activation properties of the respective promoter. For example, the disruption or deletion of a regulatory element mediating the repression of a DGA1, ACC1, or SCD promoter in response to elevated intracellular fatty acid levels would lead to continued transcriptional activation of the respective gene even under conditions of elevated intracellular fatty acid levels. Similarly, the insertion of a constitutively active transcriptional activator element into a conditional promoter region may effect overexpression of the respective gene under normally inhibitive conditions. Methods for the targeted disruption of a native promoter, for example, a native DGA1, ACC1, or SCD promoter, in a microbe, for example, for targeted disruption resulting in an increased transcription rate, are well known to those of skill in the art.

Some aspects of this invention relate to engineering of a microbe, for example, *Y. lipolytica*, to exhibit a required and/or desirable phenotype for large-scale production of a biofuel or biofuel precursor. Some aspects of this invention relate to the metabolic engineering of the lipid synthesis pathway in order to yield a microbe optimized for biofuel production. Some aspects of this invention relate to metabolic engineering that comprises a combination of genetic modifications modulating the expression of genes regulating carbon flux into a lipid synthesis pathway in order to yield a microbe optimized for biofuel production. In some embodiments, the combination of genetic modifications includes a push modification and a pull modification. In some embodiments, the push modification comprises a genetic modification that increases the level of metabolites, acetyl-CoA, ATP, or NADPH for lipid synthesis in a cell, for example, overexpression of an ACC1 gene product. In some embodiments, the pull modification is a genetic modification that decreases the level of a product or intermediary of lipid synthesis that exhibits a feedback inhibitory function, for example, a fatty acid. In some embodiments, the pull modification comprises overexpression of a DGA1 and/or an SCD gene product.

Some aspects of this invention provide methods to greatly increase the efficiency of *Y. lipolytica* mediated carbon source to lipid conversion by modulating *Y. lipolytica*'s native lipid metabolism. Remarkably and unexpectedly, combinations of push-and-pull modifications of lipid metabolism according to some methods provided by this invention confers significantly increased carbon flux to lipid synthesis pathways as compared to individual modifications modulating only push or pull processes, respectively.

Some aspects of this invention relate to a microbe engineered and/or optimized for large-scale biofuel or biofuel precursor production. In some embodiments, an engineered microbe is provided that has been manipulated by a method or using a nucleic acid or protein provided by some aspects of this invention, for example, an expression construct or a combination of expression constructs as provided herein, resulting in the overexpression of a combination of a gene product mediating a push process of lipid synthesis (e.g., an ACC1 product), and a gene product mediating a pull process of lipid synthesis (e.g., a DGA1 and/or SCD gene product). In some embodiments, an engineered microbe is provided, that overexpresses a push-and-pull combination of gene products that, according to some aspects of this invention, confers a required and/or desirable phenotype for biofuel or biofuel precursor production to the microbe. In some embodiments, a microbe comprising an increased DGA1, ACC1, and/or SCD gene product activity is provided. In some embodiments, the microbe exhibits an increased fatty acid synthesis rate, an increased TAG storage, and/or an additional required or desirable trait.

The term "increased synthesis rate" or "increased rate of synthesis" as used herein in the context of microbial lipid synthesis, e.g., in the context of a fatty acid synthesis rate of an oil-producing microbe described herein, refers to a rate of synthesis in an engineered microbe that is increased as compared to the corresponding rate of synthesis in a wild-type microbe of the same species. E.g., an increased rate of TAG synthesis in an engineered *Y. lipolytica* microbe described herein refers to rate of lipid synthesis that is increased as compared to the rate of TAG synthesis in a wild-type *Y. lipolytica*. In some embodiments, an increased rate of lipid synthesis, e.g., of TAG or of total lipid synthesis, refers to a rate of fatty acid synthesis of a culture of cells, e.g., of a culture of engineered microbes. In some embodiments, an increased rate of lipid synthesis is a rate of lipid synthesis, e.g., of TAG synthesis or total lipid synthesis of at least 0.01 g/L/h (grams of lipid per liter of culture per hour), at least 0.004 g/L/h, at least 0.05 g/L/h, at least 0.1 g/L/h, at least 0.14 g/L/h, at least 0.15 g/L/h, at least 0.2 g/L/h, at least 0.3 g/L/h, at least 0.4 g/L/h, at least 0.5 g/L/h, at least 0.6 g/L/h, at least 0.7 g/L/h, at least 0.8 g/L/h, at least 0.9 g/L/h, at least 1 g/L/h, at least 2 g/L/h, at least 3 g/L/h, at least 4 g/L/h, at least 5 g/L/h, at least 6 g/L/h, at least 7 g/L/h, at least 8 g/L/h, at least 9 g/L/h, at least 10 g/L/h, or at least 25 g/L/h.

In some embodiments, the rate of synthesis in this context is the rate of synthesis measured over a complete run of a bioreactor, e.g., calculating the rate of synthesis from the total amount of lipid, e.g., TAG, synthesized over the total time that the bioreactor was run or the total time lipid production was measured over. This type of synthesis rate is also referred to herein sometimes as "total lipid productivity" or "overall lipid productivity," and it is typically provided in g/L/h (grams of lipid produced per liter of culture medium per run time in hours). In some embodiments, an engineered microbe is provided, e.g., an engineered *Y. lipolytica* that overexpresses an ACC1 gene product, a DGA1 gene product, and/or an SCD gene product, that exhibits at least a 5-fold increase, at least a 6-fold increase, at least a 7-fold increase, at least an 8-fold increase, at least a 9-fold increase, at least a 10-fold increase, at least a 12-fold increase, at least a 10-fold increase, at least a 12.5-fold increase, at least a 15-fold increase, at least a 20-fold increase, at least a 30-fold increase, at least a 40-fold increase, at least a 50-fold increase, at least a 60-fold increase, at least a 70-fold increase, at least an 80-fold increase, at least a 90-fold increase, at least a 100-fold increase, at least a 500-fold increase, or at least a 1000-fold increase in total lipid productivity as compared to a wild-type microbe, e.g., a wild-type *Y. lipolytica*.

In some embodiments, an increased rate of total lipid synthesis or an increased total lipid productivity is at least 0.01 g/L/h, at least 0.004 g/L/h, at least 0.05 g/L/h, at least 0.1 g/L/h, at least 0.14 g/L/h, at least 0.15 g/L/h, at least 0.2 g/L/h, at least 0.3 g/L/h, at least 0.4 g/L/h, at least 0.5 g/L/h, at least 0.6 g/L/h, at least 0.7 g/L/h, at least 0.8 g/L/h, at least 0.9 g/L/h, at least 1 g/L/h, at least 2 g/L/h, at least 3 g/L/h, at least 4 g/L/h, or at least 5 g/L/h.

In some embodiments, the rate of synthesis is the maximum rate of synthesis, or the peak rate of synthesis, measured, e.g., under optimal growth conditions and exposure to nutrients. This type of synthesis rate is also referred to herein sometimes as "maximum lipid productivity". In some embodiments, an increased maximum rate of lipid synthesis is a rate of lipid synthesis, e.g., of TAG synthesis, of at least 0.2 g/L/h, at least 0.3 g/L/h, at least 0.4 g/L/h, at least 0.5 g/L/h, at least 0.6 g/L/h, at least 0.7 g/L/h, at least 0.8 g/L/h, at least 0.9 g/L/h, at least 1 g/L/h, at least 2 g/L/h, at least 3 g/L/h, at least 4 g/L/h, at least 5 g/L/h, at least 6 g/L/h, at least 7 g/L/h, at least 8 g/L/h, at least 9 g/L/h, at least 10 g/L/h, or at least 25 g/L/h.

In some embodiments, the engineered microbe is an oleaginous yeast, for example, *Y. lipolytica*. In some embodiments, an engineered yeast provided by this invention exhibits one or more highly desirable and unexpected phenotypic characteristics, for example: increased carbon to oil conversion rate or efficiency, increased lipid accumulation in a lipid body.

In some embodiments, an engineered microbe, for example, an engineered yeast, provided by aspects of this invention exhibits a carbon to oil conversion rate, also referred to herein as "lipid yield," within the range of about 0.02 g/g (g oil, lipid, or TAG produced/g carbon, e.g., glucose, acetate, or acetic acid consumed) to about 0.3 g/g. In some embodiments, the engineered microbe, for example, the engineered yeast, provided by aspects of this invention exhibits a carbon to oil conversion rate of about 0.010 g/g, about 0.02 g/g, about 0.025 g/g, about 0.03 g/g, about 0.04 g/g, about 0.05 g/g, about 0.06 g/g, about 0.07 g/g, about 0.075 g/g, about 0.08 g/g, about 0.09 g/g, about 0.1 g/g, about 0.11 g/g, about 0.12 g/g, about 0.13 g/g, about 0.14 g/g, about 0.15 g/g, about 0.16 g/g, about 0.17 g/g, about 0.18 g/g, about 0.19 g/g, about 0.2 g/g, about 0.21 g/g, about 0.22 g/g, about 0.23 g/g, about 0.24 g/g, about 0.25 g/g, about 0.26 g/g, about 0.27 g/g, about 0.28 g/g, about 0.29 g/g, about 0.3 g/g, about 0.31 g/g, about 0.32 g/g, or approaching theoretical values. In some embodiments, the engineered microbe, for example, the engineered yeast, provided by aspects of this invention exhibits a carbon to oil conversion rate of at least about 0.010 g/g (g lipid produced/g carbon, e.g., glucose, acetate, or acetic acid consumed), at least about 0.02 g/g, at least about 0.025 g/g, at least about 0.03 g/g, at least about 0.04 g/g, at least about 0.05 g/g, at least about 0.06 g/g, at least about 0.07 g/g, at least about 0.075 g/g, at least about 0.08 g/g, at least about 0.09 g/g, at least about 0.1 g/g, at least about 0.11 g/g, at least about 0.12 g/g, at least about 0.13 g/g, at least about 0.14 g/g, at least about 0.15 g/g, at least about 0.16 g/g, at least about 0.17 g/g, at least about 0.18 g/g, at least about 0.19 g/g, at least about 0.2 g/g, at least about 0.21 g/g, at least about 0.22 g/g, at least about 0.23 g/g, at least about 0.24 g/g, at least about 0.25 g/g, at least about 0.26 g/g, at least about 0.27 g/g, at least about 0.28 g/g, at least about 0.29 g/g, at least about 0.3 g/g, at least about 0.31 g/g, at least about 0.32 g/g, or approaching theoretical values.

The term "lipid titer" as used herein in the context of microbial lipid synthesis, e.g., in the context of a fatty acid synthesis by an oil-producing microbe described herein, refers to an amount of lipid synthesized per volume of a microbial culture comprising the oil-producing microbe. In some embodiments, an engineered microbe, e.g., an engineered *Y. lipolytica* microbe described herein, can achieve or does achieve a lipid titer of at least 1 g/L (grams of lipid per liter of microbial culture), at least 2 g/L, at least 3 g/L, at least 4 g/L, at least 5 g/L, at least 6 g/L, at least 7 g/L, at least 8 g/L, at least 9 g/L, at least 10 g/L, at least 15 g/L, at least 20 g/L, at least 25 g/L, at least 30 g/L, at least 40 g/L, at least 50 g/L, at least 60 g/L, at least 70 g/L, at least 80 g/L, at least 90 g/L, at least 100 g/L, at least 200 g/L, or at least 250 g/L.

In some embodiments, an engineered microbe as provided herein exhibits an increased lipid titer during carbon to oil conversion. The term "increased lipid titer" as used herein in the context of microbial lipid synthesis, e.g., in the context of a fatty acid synthesis by an oil-producing microbe described herein, refers to an amount of lipid synthesized per volume of a microbial culture comprising the oil-producing microbe that is increased as compared to the corresponding lipid titer of a wild-type microbe of the same species and under the same conditions (e.g., in the same growth medium, with the same C/N ratio, the same amount of oxygen, the same pH, the same nutrients, and so forth). For example, an increased lipid titer achieved by an engineered *Y. lipolytica* microbe described herein refers to a lipid titer that is increased as compared to the lipid titer that can be achieved by a wild-type *Y. lipolytica* under identical conditions. In some embodiments, an increased lipid titer refers to a lipid titer of at least 1 g/L (grams of lipid per liter of microbial culture), at least 2 g/L, at least 3 g/L, at least 4 g/L, at least 5 g/L, at least 6 g/L, at least 7 g/L, at least 8 g/L, at least 9 g/L, at least 10 g/L, at least 15 g/L, at least 20 g/L, at least 25 g/L, at least 30 g/L, at least 40 g/L, at least 50 g/L, at least 60 g/L, at least 70 g/L, at least 80 g/L, at least 90 g/L, at least 100 g/L, at least 200 g/L, or at least 250 g/L.

Some aspects of this invention provide engineered microbes for oil production that can use a variety of carbon sources, including, but not limited to fermentable sugars, for example, C6 sugars, such as glucose, and organic acids, e.g., acetic acid, and/or their salts, e.g., acetate.

Some aspects of this invention relate to cultures of genetically modified microbes provided herein. In some embodiments, the culture comprises a genetically modified microbe provided herein and a medium, for example, a liquid medium. In some embodiments, the culture comprises a genetically modified microbe provided herein and a carbon source, for example, a fermentable carbohydrate source, or an organic acid or salt thereof. In some embodiments, the culture comprises a genetically modified microbe provided herein and a salt and/or buffer establishing conditions of salinity, osmolarity, and pH, that are amenable to survival, growth, and/or carbohydrate to biofuel or biofuel precursor conversion by the microbe. In some embodiments, the culture comprises an additional component, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions.

While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); and Christine Guthrie and Gerald R. Fink, *Guide to Yeast Genetics and Molecular and Cell Biology, Part C, Volume* 351, Academic Press; 1st edition (Jul. 9, 2002), all of which are incorporated by reference herein. For oil production, the cultures of engineered microbes described herein are cultured under conditions suitable for oil accumulation, as known in the art.

In some embodiments, the genetically modified microbe exhibits a growth advantage over wild type microbes of the same kind and/or over other microbes, for example, microbes commonly found to contaminate microbial cultures for carbon source to biofuel or biofuel precursor conversion. In some embodiments, the growth and/or proliferation advantage of an engineered microbe provided by aspects of this invention translates into the possibility of using non-sterile culturing and fermentation conditions for biofuel or biofuel precursor production, because the problem of culture overgrowth by contaminating microbes is mitigated or completely abolished. In some embodiments, an engineered microbe provided by aspects of this invention is cultured under non-sterile conditions for biofuel or biofuel precursor production. For example, in some embodiments, non-sterilized feedstock, non-sterilized culture media, non-sterilized supplements, or a non-sterilized bioreactor (e.g. an open reactor under non-sterile conditions) is used for biofuel or biofuel precursor production.

A variety of different microbes can be genetically modified according to some aspects of this invention and used for industrial-scale biofuel or biofuel precursor production, for example, microbes from various sources of yeast, such as oleaginous yeast, bacteria, algae and fungi. Non-limiting examples of suitable yeast cells are cells from *Yarrowia lipolytica, Hansenula polymorpha, Pichia pastoris, Saccharomyces cerevisiae, S. bayanus, S. K. lactis, Waltomyces lipofer. Mortierella alpine, Mortierella isabellina, Hansenula polymorpha., Mucor rouxii, Trichosporon cutaneu, Rhodotorula glutinis Saccharomyces diastasicus, Schwanniomyces occidentalis, S. cerevisiae, Pichia stipitis*, and *Schizosaccharomyces pombe*. Non-limiting examples of suitable bacteria are *Bacillus subtilis, Salmonella, Escherichia coli, Vibrio cholerae, Streptomyces, Pseudomonas fluorescens, Pseudomonas putida, Pseudomonas* sp, *Rhodococcus* sp, *Streptomyces* sp, and *Alcaligenes* sp. Non-limiting examples of suitable fungal cells can, for example, be cultured from species such as *Aspergillus shirousamii, Aspergillus niger* and *Trichoderma reesei*. Non-limiting examples of suitable algal cells are cells from *Neochloris oleoabundans, Scenedesmus obliquus, Nannochloropsis* sp., *Dunaliella tertiolecta, Chlorella vulgaris, Chlorella emersonii*, and *Spirulina maxima*.

Some aspects of this invention provide methods for the production of biofuel or biofuel precursors using genetically modified microbes provided herein. In some embodiments, methods for biofuel or biofuel precursor production on an industrial scale are provided.

A variety of carbon sources can be converted into a biofuel or biofuel precursor using a method and/or a genetically modified microbe provided herein. In some embodiments, the carbon source comprises a carbohydrate. Sugars, starches, and fibers are non-limiting examples of carbohydrate sources suitable for conversion methods provided herein. According to some aspects of this invention, a carbohydrate source may comprise a refined and/or unrefined sugar, starch, and/or fiber, or a combination of any of these. Non-limiting examples of sugars are fermentable sugars, such as glucose, fructose, sucrose, xylose, and lactose. Non-limiting examples of starches are amylase and amylopectin. Non-limiting examples of fibers are plant fibers, such as cellulose, hemi-cellulose and wood fibers. Some aspects of this invention relate to the use of industrial byproducts, intermediates, or waste products, for example raw plant extracts, molasses, stover, or sewage as a carbon source. In some embodiments, the carbon source is derived from algae. In some embodiments, algal biomass is produced specifically for use as a carbon source in microbe-mediated biofuel or biofuel precursor production.

In some embodiments, methods for the production of biofuel or biofuel precursor are provided that include the use of a cheap, abundant, and readily available carbon source feedstock as the carbon source. In some embodiments, cellulose or hemicellulose is used as the carbon source. In some embodiments, the cellulose or hemicellulose is derived from industrial by—or waste products. In some embodiments, the cellulose or hemicellulose is derived directly from plant or algal biomass. Plant or algal biomass is one of the most abundant feedstocks and comprises a significant amount of non-fermentable sugars and fibers, for example, cellulose and hemi-cellulose. In some embodiments, biomass feedstock is pretreated to convert a non-fermentable sugar or fiber into a fermentable sugar, thus making them available for microbe growth and microbe-mediated biofuel or biofuel precursor production. In some embodiments, the pretreatment of biomass feedstock includes depolymerizing cellulose and/or hemicellulose components to monomeric sugars using a pretreatment method known to those of skill in the art, for example, a dilute acid or ammonia fiber expansion (AFEX) method (see, e.g., Yang B, Wyman C E. *Dilute acid and autohydrolysis pretreatment*. Methods Mol. Biol. 2009; 581: 103-14; Balan V, Bals B, Chundawat S P, Marshall D, Dale B E, *Lignocellulosic biomass pretreatment using AFEX Methods* Mol. Biol. 2009; 581:61-77). Other methods for depolymerization of biomass polymers to monomeric sugars are well known to those of skill in the art and are contemplated to be used in some embodiments of this invention.

In some embodiments, a biomass feedstock containing non-fermentable sugars is pretreated using a dilute acid method to depolymerize a non-fermentable sugar to a monomeric, fermentable sugar. In some embodiments, biomass is treated with dilute sulphuric acid at moderately mild temperatures for a defined period of time. For example, in some embodiments, the biomass is treated with about 0.5%, about 1%, about 2%, about 3%, about 4%, about 5%, or about 6% sulphuric acid. In some embodiments, the biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C.

In some embodiments, the resulting hydrolysate contains insoluble lignin and solubilized cellulosic and hemicellulosic polymers. The latter products can be further treated to generate hexose and pentose sugars such as glucose and xylose monomers by methods well known to those of skill in the art, for example, by treatment with cellulase or other hydrolyzing enzymes. In some embodiments, the pretreatment of non-fermentable sugars with dilute acid results in the generation of by-products that include toxic compounds which inhibit growth, decrease viability, and/or inhibit biofuel or biofuel precursor production of microbes not engineered according to aspects of this invention. In some embodiments, the pretreated feedstock is washed, supplemented with media supporting microbial growth and biofuel or biofuel precursor production, and/or over-limed for detoxification.

In some embodiments, a biomass feedstock containing non-fermentable sugars is pretreated using an AFEX method to depolymerize a non-fermentable sugar to a monomeric, fermentable sugar. In some embodiments, biomass is treated with liquid ammonia at high temperature and pressure for a defined period of time. In some embodiments, biomass is treated for about 10 minutes, about 20 minutes, about 30 minutes, about 40 minutes, about 50 minutes, about 60 minutes, about 70 minutes, about 80 minutes, about 90 minutes, or longer. In some embodiments, biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C. In some embodiments, the AFEX pretreatment results in the conversion of crystalline cellulose contained in the feedstock into an amorphous, fermentable form. In some embodiments, the AFEX pre-treated biomass feedstock does not contain significant amounts of toxic byproducts that inhibit microbial growth and/or biofuel or biofuel precursor production, and is used without prior detoxification for microbial biofuel or biofuel precursor production.

In some embodiments, biomass feedstock, with or without pre-treatment, is treated with an enzyme that hydrolyzes or depolymerizes sugar polymers, for example, with a cellulase or hemicellulase enzyme. In some embodiments, the feedstock is contacted with the enzyme in a liquid phase and incubated at a temperature allowing for the enzyme to catalyze a depolymerization or hydrolyzation reaction for a time sufficient to hydrolyze or depolymerize a significant amount of the non-fermentable sugar or fiber in the biomass feedstock. In some embodiments, the liquid phase of the feedstock contacted with the enzyme, which contains the soluble, fermentable sugar fraction, is separated from the solid phase, including non-fermentable sugars and fibers, after incubation for hydrolyzation and depolymerization, for example, by centrifugation. In some embodiments, the liquid fraction of the feedstock is subsequently contacted with a microbe, for example, a microbe provided by aspects of this invention, for conversion to biofuel or biofuel precursor. In some embodiments, enzymatic conversion of non-fermentable sugars or fiber occurs in a consolidated bioprocess, for example, at the same time and/or in the same reactor as microbial conversion of the produced fermentable sugars to biofuel or biofuel precursor. In some embodiments, the enzymatic conversion is performed first, and the feedstock contacted with enzyme is subsequently contacted with the microbe for biofuel or biofuel precursor production. In some embodiments, enzymatic and microbial conversion are performed at the same time and in the same reactor.

In some embodiments, an engineered microbe as provided herein, for example, a *Yarrowia lipolytica* overexpressing a DGA1, ACC1, and/or SCD gene product, is grown on acetate as the main carbon source. In some embodiments, the microbe is grown in a solution of acetic acid with a concentration of about 1%, about 2%, about 3%, about 4%, about 5%, about 6%, about 7%, about 8%, about 9%, about 10% vol/vol, about 20% vol/vol, about 25% vol/vol, or about 30% vol/vol. In some embodiments, the acetate concentration is between about 3%-10% wt/vol. In some embodiments, cell cultures comprising genetically modified microbes as provided herein that are cultured on acetate or acetic acid as the main carbon source are contacted, or "spiked," with glycerol. In some embodiments, the genetically modified microbes are intermittently contacted with glycerol. In some embodiments, the microbes are continuously or semi-continuously contacted with glycerol. In some embodiments, the microbes are contacted with glycerol at a concentration of about 0.5%, about 1%, about 2%, about 3%, about 4%, or about 5% vol/vol. Contacting the engineered microbes provided herein with glycerol provides metabolites for the production of TAGs, as well as reducing moieties for the production of fatty acids from carbohydrates. In some embodiments, glycerol spiking is performed in biofuel or biofuel precursor production methods using a carbon source other than acetate, for example, any carbon source described herein.

In some embodiments, an engineered microbe as provided herein, for example, a *Yarrowia lipolytica* overexpressing a DGA1 gene product, and/optionally, and ACC1 and/or SCD gene product, is grown on a carbon source, e.g., on acetate or acetic acid, that is replenished during the growth process or culture period, e.g, by contacting the microbe with an additional amount of the carbon source, or with an amount of an additional carbon source, after a period of time in culture, e.g., after 8 hours, after 24 hours, or after 48 hours. In some embodiments, an engineered microbe as provided herein is grown initially, e.g., for the first 6, 12, 18, 24, 30, 36, 42, 48, 54, 60, 66, or 72 hours in a culture medium that comprises a low carbon to nitrogen (C/N) ratio, e.g., a C/N ratio of about 10, of about 20, of about 25, of about 30, of less than 30, of less than 25, or of less than 20. In some embodiments, a low C/N ratio is achieved by supplementing the culture media with a nitrogen source, e.g., with ammonia, to achieve the desired C/N ratio. In some embodiments, e.g., in embodiments, where carbon source, e.g., acetate or acetic acid, is fed into a culture of oil-producing microbes as described herein, the carbon source is supplemented with a nitrogen source, e.g., ammonia. In some embodiments, the supplementation with a nitrogen source is ceased after an initial period of time in culture, e.g., after for the first 6, 12, 18, 24, 30, 36, 42, 48, 54, 60, 66, or 72 hours in culture, thus allowing the engineered microbes in culture to consume the nitrogen source, which, in turn, results in an increase of the C/N ratio. This shift in C/N ratio can be enhanced or sped up by feeding additional carbon source into the culture that is not supplemented with a nitrogen source, e.g., by feeding acetic acid or acetate that is not supplemented with ammonia or any other nitrogen source. In some embodiments, the optimal C/N ratio for oil production by an engineered microbe described herein is within the range of 80-120.

In some embodiments, fermentation processes for large-scale microbe-mediated carbohydrate to lipid conversion may be carried out in bioreactors. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate a product, for example a biofuel or biofuel precursor, for example a fatty acid and/or TAG, on a commercial or quasi-commercial scale. Large scale bioreactors typically have volumes in the range of liters, hundreds of liters, thousands of liters, or more.

A bioreactor in accordance with aspects of this invention may comprise a microbe or a microbe culture. In some embodiments, a bioreactor may comprise a spore and/or any kind of dormant cell type of any isolated microbe provided by aspects of this invention, for example, in a dry state. In some embodiments, addition of a suitable carbohydrate source to such bioreactors may lead to activation of the dormant cell, for example to germination of a yeast spore, and subsequent conversion of the carbohydrate source, at least in part, to a biofuel or biofuel precursor.

Some bioreactors according to aspects of this invention may include cell culture systems where microbes are in contact with moving liquids and/or gas bubbles. Microbes or microbe cultures in accordance with aspects of this invention may be grown in suspension or attached to solid phase carriers. Non-limiting examples of carrier systems include microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

Industrial-scale carbohydrate to lipid conversion processes in accordance with aspects of this invention may be operated in continuous, semi-continuous or non-continuous modes. Non-limiting examples of operation modes in accordance with this invention are batch, fed batch, extended batch, repetitive batch, draw/fill, rotating-wall, spinning flask, and/or perfusion mode of operation.

In some embodiments, bioreactors may be used that allow continuous or semi-continuous replenishment of the substrate stock, for example a carbohydrate source and/or continuous or semi-continuous separation of the product, for example a secreted lipid, an organic phase comprising a lipid, and/or cells exhibiting a desired lipid content, from the reactor.

Non-limiting examples of bioreactors in accordance with this invention are: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multiwell plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

Bioreactors and fermentors according to aspects of this invention may, optionally, comprise a sensor and/or a control system to measure and/or adjust reaction parameters. Non-limiting examples of reaction parameters are: biological parameters, for example growth rate, cell size, cell number, cell density, cell type, or cell state, chemical parameters, for example pH, redox-potential, concentration of reaction substrate and/or product, concentration of dissolved gases, such as oxygen concentration and $CO_2$ concentration, nutrient concentrations, metabolite concentrations, glucose concentration, glutamine concentration, pyruvate concentration, apatite concentration, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products, physical/mechanical parameters, for example density, conductivity, degree of agitation, pressure, and flow rate, shear stress, shear rate, viscosity, color, turbidity, light absorption, mixing rate, conversion rate, as well as thermodynamic parameters, such as temperature, light intensity/quality etc.

Sensors able to measure parameters as described herein are well known to those of skill in the relevant mechanical and electronic arts. Control systems able to adjust the parameters in a bioreactor based on the inputs from a sensor as described herein are well known to those of skill in the art of bioreactor engineering.

The type of carbon source to be employed for conversion to a biofuel or biofuel precursor according to aspects of this invention depends on the specific microbe employed. Some microbes provided by aspects of this invention may be able to efficiently convert a specific carbohydrate source, while a different carbohydrate source may not be processed by the same microbe at high efficiency or at all. According to aspects of this invention, the oleaginous yeast *Y. lipolytica*, for example, can efficiently convert sugars, such as glucose, fructose, sucrose, and/or lactose, and carbohydrate sources high in sugars, for example molasses, and plant fibers into fatty acids and their derivatives.

In some embodiments, a biofuel or biofuel precursor, for example, a fatty acid or a triacylglycerol, generated from a carbon source feedstock is secreted, at least partially, by a microbe provided by aspects of this invention, for example, an oleaginous yeast, such as a *Y. lipolytica* cell. In some embodiments, a microbe provided by aspects of this invention is contacted with a carbohydrate source in an aqueous solution in a bioreactor, and secreted biofuel or biofuel precursor forms an organic phase that can be separated from the aqueous phase. The term organic phase, as used herein, refers to a liquid phase comprising a non-polar, organic compound, for example a fatty acid, TAG, and/or other non-polar lipid. And organic phase in accordance to this invention might further contain a microbe, a carbohydrate, or other compound found in other phases found in a respective bioreactor. Methods useful for industrial scale phase separation are well known to those of ordinary skill in the art. In some embodiments, the organic phase is continuously or semi-continuously siphoned off. In some embodiments, a bioreactor is employed, comprising a separator, which continuously or semi-continuously extracts the organic phase.

In some embodiments, a biofuel or biofuel precursor is accumulated in cells according to aspects of this invention. In some embodiments, cells that have accumulated a desirable amount of biofuel or biofuel precursor, are separated continuously or semi-continuously from a bioreactor, for example, by centrifugation, sedimentation, or filtration. Cell separation can further be effected, for example, based on a change in physical cell characteristics, such as cell size or density, by methods well known to those skilled in the art. The accumulated biofuel or biofuel precursor can subsequently be extracted from the respective cells using standard methods of extraction well known to those skilled in the art, for example, solvent hexane extraction. In some embodiments, microbial cells are collected and extracted with 3 times the collected cell volume of hexane. In some embodiments, the extracted biofuel or biofuel precursor are further refined. In some embodiments, a biofuel precursor, for example a triacylglycerol is converted to a biofuel, for example, biodiesel, using a method well known to those of skill in the art, for example, a transesterification procedure.

The function and advantage of these and other embodiments of the present invention will be more fully understood from the examples below. The following examples are intended to illustrate the benefits of the present invention, but do not exemplify the full scope of the invention. Accordingly, it will be understood that the example section is not meant to limit the scope of the invention.

EXAMPLES

Example 1

Materials and Methods

Yeast Strains, Growth, and Culture Conditions

The *Y. lipolytica* strains used in this study were derived from the wild-type *Y. lipolytica* W29 strain (ATCC20460). The auxotrophic Po1g (Leu⁻) used in all transformations was obtained from Yeastern Biotech Company (Taipei, Taiwan). All strains used in this study are listed in Table 1.

TABLE 1

Total fatty acid content, yield and distribution for *Y. lipolytica* strains. Total fatty acid content is given as means ± S.D. (n = 3) for a 50 mL culture after 100 hrs (C/N molar ratio of 20). Fatty acid profiles are given as percent of fatty acid of total fatty acids, with error less than 2.5%.

| | Biomass (g DCW) | Lipid Content (%) | Oil Yield (g/g glucose) | Fatty Acid (Fractional Abundance %) | | | | |
|---|---|---|---|---|---|---|---|---|
| | | | | C16 | C16:1 | C18:0 | C18:1 | C18:2 |
| Control (MTYL037) | 10.49 | 8.77 ± 0.37 | 2.28 | 20.5 | 3.9 | 24.0 | 43.0 | 8.7 |
| ACC1 (MTYL040) | 6.04 | 17.9 ± 1.13 | 6.25 | 20.3 | 3.5 | 23.4 | 41.7 | 11.0 |
| DGA1 (MTYL053) | 7.53 | 33.8 ± 0.55 | 9.36 | 18.3 | 2.6 | 34.1 | 38.6 | 6.4 |
| ACC1 + DGA1 (MTYL065) | 8.60 | 41.4 ± 1.90 | 11.4 | 16.0 | 2.3 | 32.8 | 44.9 | 4.0 |

Media and growth conditions for *Escherichia coli* have been previously described by Sambrook et al. (21), and those for *Y. lipolytica* have been described by Barth and Gaillardin (11). Rich medium (YPD) was prepared with 20 g/L Bacto peptone (Difco Laboratories, Detroit, Mich.), 10 g/L yeast extract (Difco), 20 g/L glucose (Sigma-Aldrich, St. Louis, Mo.). YNB medium was made with 1.7 g/L yeast nitrogen base (without amino acids) (Difco), 0.69 g/L CSM-Leu (MP Biomedicals, Solon, Ohio), and 20 g/L glucose. Selective YNB plates contained 1.7 g/L yeast nitrogen base (without amino acids), 0.69 g/L CSM-Leu, 20 g/L glucose, and 15 g/L Bacto agar (Difco).

Shake flask experiments were carried out using the following medium: 1.7 g/L yeast nitrogen base (without amino acids), 1.5 g/L yeast extract, and 50 g/L glucose. From frozen stocks, precultures were inoculated into YNB medium (5 mL in Falcon tube, 200 rpm, 28° C., 24 hr). Overnight cultures were inoculated into 50 mL of media in 250 mL Erlenmeyer shake flask to an optical density ($A_{600}$) of 0.05 and allowed to incubate for 100 hours (200 rpm, 28° C.), after which biomass, sugar content, and lipid content were taken and analyzed.

Bioreactor scale fermentation was carried out in a 2-liter baffled stirred-tank bioreactor. The medium used contained 1.5 g/L yeast nitrogen base (without amino acids and ammonium sulfate), 2 g/L ammonium sulfate, 1 g/L yeast extract, and 90 g/L glucose. From a selective plate, an initial preculture was inoculated into YPD medium (40 mL in 250 mL Erlenmeyer flask, 200 rpm, 28° C., 24 hr). Exponentially growing cells from the overnight preculture were transferred into the bioreactor to an optical density ($A_{600}$) of 0.1 in the 2-L reactor (2.5 vvm aeration, pH 6.8, 28° C., 250 rpm agitation). Time point samples were stored at −20° C. for subsequent lipid analysis. Sugar organic acid content was determined by HPLC. Biomass was determined by determined gravimetrically from samples dried at 60° C. for two nights.

Plasmid Construction

Standard molecular genetic techniques were used throughout this study (21). Restriction enzymes and Phusion High-Fidelity DNA polymerase used in cloning were obtained from New England Biolabs (Ipswich, Mass.). Genomic DNA from yeast transformants was prepared using Yeastar Genomic DNA kit (Zymo Research, Irvine, Calif.). All constructed plasmids were verified by sequencing. PCR products and DNA fragments were purified with PCR Purification Kit or QIAEX II kit (Qiagen, Valencia, Calif.). Plasmids used are described in Table 3. Primers used are described in Table 4.

Plasmid pMT010 was constructed by amplifying the translation elongation factor-1α (TEF) promoter region (Accession number: AF054508) from *Y. lipolytica* Po1g genomic DNA using primers MT078 and MT079. The amplicon was inserted between SalI and KpnI sites of the starting vector, pINA1269, also known as pYLEX1, obtained from Yeastern Biotech Company (Taipei, Taiwan). Also included in the reverse primer MT079 were MluI and NsiI sites to add restriction sites to the multi-cloning site.

Plasmid pMT015 was constructed by amplifying from *Y. lipolytica* Po1g genomic DNA the TEF promoter and the 5' coding region containing the ATG start codon and 113 bp of the endogenous intron (Accession number: CR382129). Primers MT118 and MT122 were used for this amplification and inserted between SalI and MluI sites of pMT010. For cloning purposes, some of the intron was omitted so that the SnaBI restriction site could be incorporated. Cloning a gene into this plasmid thus requires the omission of the gene's ATG start codon, addition of TAACCGCAG to the beginning of the 5' primer, and blunt-end ligation at the 5' end.

Plasmid pMT025 was constructed by amplifying the LacZ gene, encoding β-galactosidase, from *E. coli* and inserting it into the PmlI and BamHI sites of starting vector pINA1269 using primers MT170 and MT171. Plasmid pMT038 was constructed by amplifying the LacZ gene and inserting it into the MluI and NsiI sites of pMT010 using primers MT168 and MT169. Since LacZ contains multiple MluI sites, AscI was used as the 5' restriction site on MT168 which has a matching overhang. Plasmid pMT037 was constructed by amplifying LacZ gene and inserting it into the SnaBI and NsiI sites of pMT015. Primers MT172 and MT169 were used, where forward primer MT127 omits the ATG start codon of LacZ and instead begins with the sequence TAACCGCAG which completes the intron sequence of pMT015.

Plasmid pMT013 was constructed by amplifying the ACC1 gene from *Y. lipolytica* Po1g genomic DNA (Accession Number: XM_501721) and inserting it into the MluI and NsiI sites of pMT010 using primers MT080 and MT081. Plasmid pMT040 was constructed by amplifying the ACC1 gene and its terminator from pMT013 using primers MT222 and MT137 and inserting this into starting vector pINA1269 digested with PmlI and ClaI.

Plasmid pMT053 was constructed by amplifying the DGA1 gene from *Y. lipolytica* Po1g genomic DNA (Accession Number: XM_504700) using primers MT271 and MT272. The amplified gene was digested with NsiI and was inserted into PMT015 in the same manner as in the construction of pMT037.

To produce a single plasmid which could express both ACC1 and DGA1, a promoter-gene-terminator cassette was amplified from pMT053 using primers MT220 and MT265. This was then digested with DpnI and AseI and inserted into pMT040 which was digested with NruI and AseI resulting in tandem gene construct pMT065. The AseI restriction site was selected to facilitate selection, as it resides within the Ampicillin resistance marker. Because NruI is a blunt end restriction site, insertion of the amplicon does not increase the total number of NruI sites to facilitate progressive insertions.

Plasmids were linearized with either NotI or SacII and chromosomally integrated into Po1g according to the one-step lithium acetate transformation method described by Chen et al. (22). Transformants were plated on selective media and verified by PCR of prepared genomic DNA. Verified transformants were then stored as frozen stocks at −80° C. and on selective YNB plates at 4° C.

RNA Isolation and Transcript Quantification

The yeast strains were grown on YNB for 24 hr, harvested, frozen with liquid nitrogen and kept at 80° C. Samples were crushed in liquid nitrogen, and total RNA was isolated from *Y. lipolytica* with the RNeasy Mini Kit (Qiagen) and treated with RNase-free DNase during the isolation step according to the manufacturer's instructions. The isolated RNA was quantified by spectrophotometry at 260 nm. qRT-PCR analyses were carried out using iScript One-step RT-PCR Kit with SYBR Green (Bio-Rad, Hercules, Calif.). Relative quantification was based on the $2^{\Delta CT}$ method using ACT1, encoding for actin, as an internal control. Samples were analyzed in triplicate.

β-Galactosidase Assay

LacZ enzyme activity was measured using the β-gal assay kit from Sigma-Aldrich. Cells were resuspended in PBS buffer and lysed by vortexing with 500 μm glass beads (Sigma-Aldrich) for 2 minutes. 40 μL of the cell lysate was transferred into 340 μL reaction mix containing 47 mg/mL ONPG, 0.6 M Na2HPO4-7H2O, 0.4 M NaH2PO4-H2O, 0.1 M KCl, 0.01 M MgSO4-7H2O. Reaction was incubated at 37° C. for color evolution to occur, and was finally quenched using 500 μL 1 M Sodium Carbonate. Absorbance was then measured with a spectrophotometer at 420 nm. Enzymatic units are calculated based on enzyme activity divided by incubation time and dry cell weight.

Lipid Analysis

Total lipids were extracted using the procedure by Folch et al (23). A measured quantity of cell biomass (roughly 1 mg) was suspended in 1 mL of chloroform:methanol (2:1) solution and vortexed for 1 hour. After centrifugation, 500 μL was transferred to 125 μL saline solution. The upper aqueous layer was removed and the bottom layer was evaporated and resuspend in 100 μL hexane. Samples were then stored at −20° C. until transesterification.

Transesterification of total lipid extracts was performed by adding 1 mL 2% (wt/vol) sulfuric acid in methanol to each sample. Samples were then incubated at 60° C. for 2 hours. After that the samples were partially evaporated, and the fatty acid methyl esters (FAME) were extracted by adding 1 mL hexane and vortexing for 10 min. 800 μL of this hexane was then transferred into glass vials for GC analysis.

GC analysis of FAMEs was performed with a Bruker 450-GC instrument equipped with a flame-ionization detector and a capillary column HP-INNOWAX (30 m×0.25 mm). The GC oven conditions were as follows: 150° C. (1 min), a 10 min ramp to 230° C., hold at 230° C. for 2 min. The split ratio was 10:1. Fatty acids were identified and quantified by comparison with commercial FAME standards normalized to methyl tridecanoate (C13:0). Total lipid content was calculated as the sum of total fatty acid contents for five FAMEs: methyl palmitate (C16:0), methyl palmitoleate (C16:1), methyl stearate (C18:0), methyl oleate (C18:1), methyl linoleate (C18:2) (Sigma-Aldrich). The addition of tridecanoic acid to the chloroform-methanol extraction fluid was used as the internal standard, which was carried through the entire analysis procedure and transesterified into its methyl ester.

Results and Discussion

Establishing a High Expression Platform Utilizing the Expression-Enhancing Intron of Translation Elongation Factor-1α

In *Y. lipolytica*, a number of promoters are available for gene expression, including inducible and constitutive ones (24). The TEF promoter was originally identified as being a strong constitutive promoter; however, subsequent cloning and characterization resulted in lower expression relative to the inducible XPR2 promoter (25). More recently, the hybrid hp4d promoter has become popular for its strong quasi-constitutive expression (26), and has been used in a number of applications requiring high protein expression (20, 27, 28).

Analysis of the genomic sequence for TEF reveals the presence of a 122-bp spliceosomal intron immediately after the start codon in the 5' region of the open reading frame. Promoter-proximal spliceosomal introns have often been found to dramatically affect expression of their corresponding genes in a variety of organisms (29). We speculated that the strong expression of TEF was dependent on this intron, and that stronger expression could be achieved by including the intron along with the promoter in the expression vector. Indeed, the initial screening and isolation of the TEF promoter likely relied on the intron enhancement for enrichment in cDNA libraries, a feature which would not have been noticed once the intron was spliced.

Plasmids pMT025, pMT037 and pMT038 were constructed expressing LacZ to compare the relative expression of three promoters: synthetic hybrid promoter (php4d), TEF promoter without intron (pTEF), and TEF promoter with intron (pTEFin). Remarkably, the TEFin promoter exhibits a 17-fold increase in expression over the intronless TEF promoter, and a 5-fold increase in expression over the hp4d promoter after 50 hrs of culture.

The intron enhancement observed in other systems varies wildly: from only 2-fold in human cells and yeast to over 1000-fold in maize (30, 31). Introns are believed to enhance gene expression in a number of ways: by containing regulatory elements, facilitating mRNA export, and increasing transcription initiation rates (29). Intronic genes, as a group, tend to exhibit higher levels of expression relative to non-intronic genes. For example, in *S. cerevisiae*, intronic genes only represent less than 4% of the total gene count, yet account for 27% of the total RNA generated in the cell (32). The genome *Y. lipolytica* contains introns in 10.6% of its genes, compared to only 4.5% in *S. cerevisiae* (33). Enlisting this endogenous process to enhance our own desired genes represents a simple means for maximizing expression, applicable to a broad range of eukaryotic organisms. For example, there is high sequence homology of splice sequences among hemiascomycetous yeast (34). While research continues to elucidate more about the function, evolution, and purpose of introns, the utilization of introns for biotechnological purposes is a relatively untapped opportunity.

Overexpression of ACC1 and DGA1 Leads to Significant Increases in Lipid Accumulation The use of the TEF promoter along with its expression-enhancing intron provides an excellent platform for high gene expression in *Y. lipolytica*. We therefore used this for overexpression of DGA1 (pMT053), which has been shown to be important in lipid accumulation in both *Y. lipolytica* and *S. cerevisiae* (19, 35). ACC1, already having two endogenous promoter-proximal introns, was not cloned with the TEFin promoter. Instead it was cloned with TEF and hp4d promoters (pMT013 and pMT040, respectively). Growth rates and lipid production was relatively similar between the two (data not shown), so php4d-ACC1 was used for lipid experiments and for the tandem gene construction of ACC1+DGA1 (pMT065). The hp4d promoter also was selected to minimize the possibility of homologous recombination of the two parallel gene cassettes in the ACC1+DGA1 construct. Simultaneous coexpression of two genes in *Y. lipolytica* using tandem gene construction has been successfully performed elsewhere (20).

The effect of ACC1 and DGA1 overexpression on lipid production was first assessed in shake flask experiments. The control LacZ strain only produced 8.77% (g/g DCW) lipids, which is similar to wild-type performance in shake flasks with glucose as sole substrate (36). ACC1 and DGA1 transformants both outperformed the control, accumulating 17.9% and 33.8% lipid content, respectively. DGA1 in particular exhibited almost twice as much lipid accumulation as ACC1, almost 4-fold over the control. The biomass generated from the control was significantly higher than the other strains, suggesting that the expression of ACC1 and DGA1 may perturb the growth potential of *Y. lipolytica*. Overall oil yields were relatively low in comparison to a theoretical maximum yield of 0.32 g/g (37). There were also slight shifts in the fatty acid profile, with ACC1 producing significantly more linoleic acid and DGA1 maintaining a higher proportion of stearic acid. The proportion of oleic acid stayed relatively flat across all transformants.

Improving upon both single gene transformants, ACC1+DGA1 was able to achieve 41.4% lipid content, a 4.7-fold improvement over the control. The biomass production was improved over the single transformants, but still less than the control. Oil yield improved proportionally, to 0.114 g/g, or 35% of theoretical yield.

In eukaryotic organisms, overexpression of ACC has been met with only limited improvement of lipid production. Heterologous expression of ACC1 from the oleaginous fungus *Mucor rouxii* in the non-oleaginous yeast *Hansenula polymorpha* was only able to achieve a 40% increase in total fatty acid content, from 3.8% to 5.3% (38). In plants, overexpression of *Arabidopsis* ACC1 has led to dramatic increases in enzyme activity, but to no more than 30% increase in final lipid content (39, 40). It is suspected that improvements have been limited because of the strong metabolic and regulatory control maintained over this enzyme in eukarotes. ACC expression and activity is influenced by numerous transcription factors, protein kinases, and metabolites (41). For example, in *Candida* (*Yarrowia*) *lipolytica*, the accumulation of acyl-CoA in acetyl-CoA synthetase mutants led to an 8-fold decrease in ACC activity (42). Nonetheless, *Y. lipolytica* might represent a regulatory exception in eukaryotic organisms, lending much to its oleaginous nature, as here we achieve a 2-fold increase in lipid content through overexpression of endogenous ACC1.

The role of DGA has only recently been found to be important for lipid synthesis. In *Y. lipolytica*, DGA1p predominantly localizes to the membrane surface of lipid bodies and acts in concert with triglyceride lipase (TGL3) to balance TAG flux in and out of lipid bodies (16). One thus expects the storage of TAGs to rest heavily on the relative activity (and abundance) of DGA1p with respect to its TGL3p counterpart. It has also been hypothesized that DGA diverts flux away from phospholipid synthesis, and thus creates a driving force for lipid synthesis as more flux is required to produce the still necessary phospholipids (6). Consequently, overexpression of DGA1 has led to marked effects on lipid accumulation. DGA1 overexpression in an oleaginous Δsnf2 mutant led to accumulation of up to 27% lipid content in *S. cerevisiae*, a 2.3-fold increase (35). In plants, *Arabidopsis* DGAT overexpression led to a 20-fold increase in lipid content in the leaves, and two-fold overall (43).

The balance between fatty acid and TAG synthesis pathways revolves around the acyl-CoA intermediates, since they function as both product and feedback inhibitors in the fatty acid (upstream) pathway and primary precursors in the TAG (downstream) pathway. Up-regulation of the upstream pathway increases the throughput of fatty acid synthesis and, for ACC in particular, diverts flux away from any pathways which would compete for cytosolic acetyl-CoA. Up-regulation of the downstream pathway creates a driving force by depleting acyl-CoA intermediates and increasing the rate of storage of TAG in lipid bodies. However, when modulated individually, they can lead to imbalances which can produce adverse effects on cell metabolism and growth.

By coexpressing ACC1 and DGA1, both upstream and downstream pathways are simultaneously up-regulated, which leads to increased lipid production without perturbing intermediate-mediated regulation. It also combines high flux through lipid synthesis from ACC with the driving force provided by the sequestration of TAG into lipid bodies by DGA. The result is a synergistic increase in lipid accumulation, almost 5-fold greater than the control. Indeed, coupling overproduction and driving forces with a metabolic sink has become a very powerful strategy in recent efforts of metabolic engineering, particularly for biofuels (44-46).

Fermentation Performance of the ACC1+DGA1 Transformant

To further characterize the ACC1+DGA1 transformant (MTYL065) and explore its lipid accumulation characteristics, large-scale fermentation was conducted using a 2-L stirred-tank bioreactor. Glucose concentration was increased and ammonium sulfate concentration was reduced to achieve a C/N molar ratio of 100. Optimal C/N molar ratios for lipid accumulation typically range from 80-120 (15).

Figure 3:
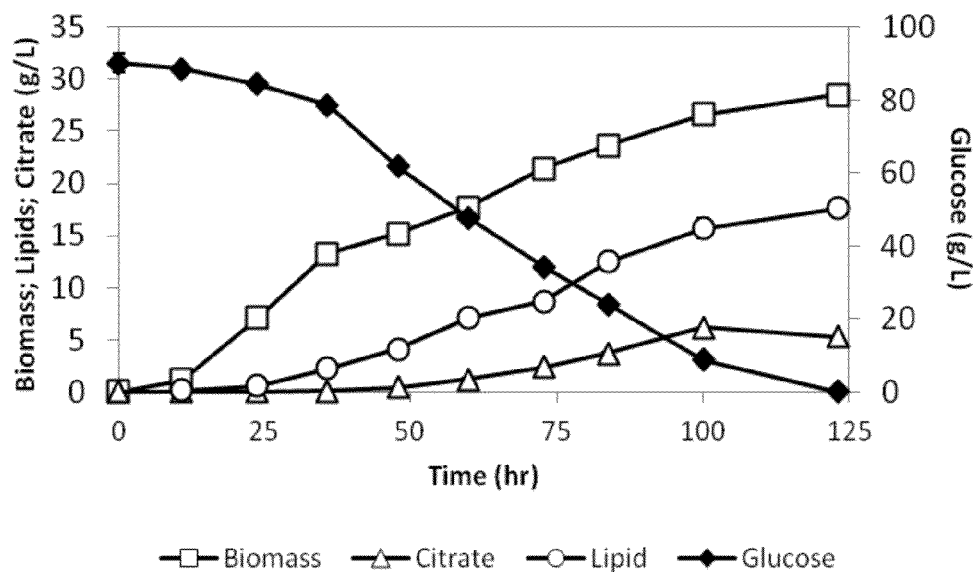
FIG. 3. Bioreactor fermentation of ACC1+DGA1 transformant (MTYL065).

Glucose was fully consumed over the course of the 120 hour fermentation, with final biomass reaching 28.49 g/L (FIG. 3). Final lipid content was 61.7% of DCW, a 50% increase in lipid accumulation compared to the shake flask experiment. This compares favorably with other sugar fermentations (28, 47-49), as well as values found in ex novo lipid accumulation schemes (19, 50). Overall yield and productivity was 0.195 g/g and 0.143 g/L/hr, respectively; however, during maximum lipid production observed between 70-100 hours, a yield of 0.270 g/g, and a productivity of 0.253 g/L/hr were reached (Table 2). Almost all biomass produced during this phase can be accounted for by the increase in lipid content. The overall and maximum yields achieved are 60.9% and 84.3% of the theoretical yield for TAG synthesis.

TABLE 2

Yield and Productivity calculations for 2-L bioreactor fermentation of ACC1 + DGA1 transformant. Yield is calculated by grams lipids produced divided by grams glucose consumed. Productivity calculated by concentration of lipids produced per hour. Maximum values calculated from the time points between 70-100 hrs.

| Oil Yield (g/g glucose) | |
| --- | --- |
| Overall | 0.195 |
| Maximum | 0.270 |
| Oil Productivity (g/L/hr) | |
| Overall | 0.143 |
| Maximum | 0.253 |

Figure 4:
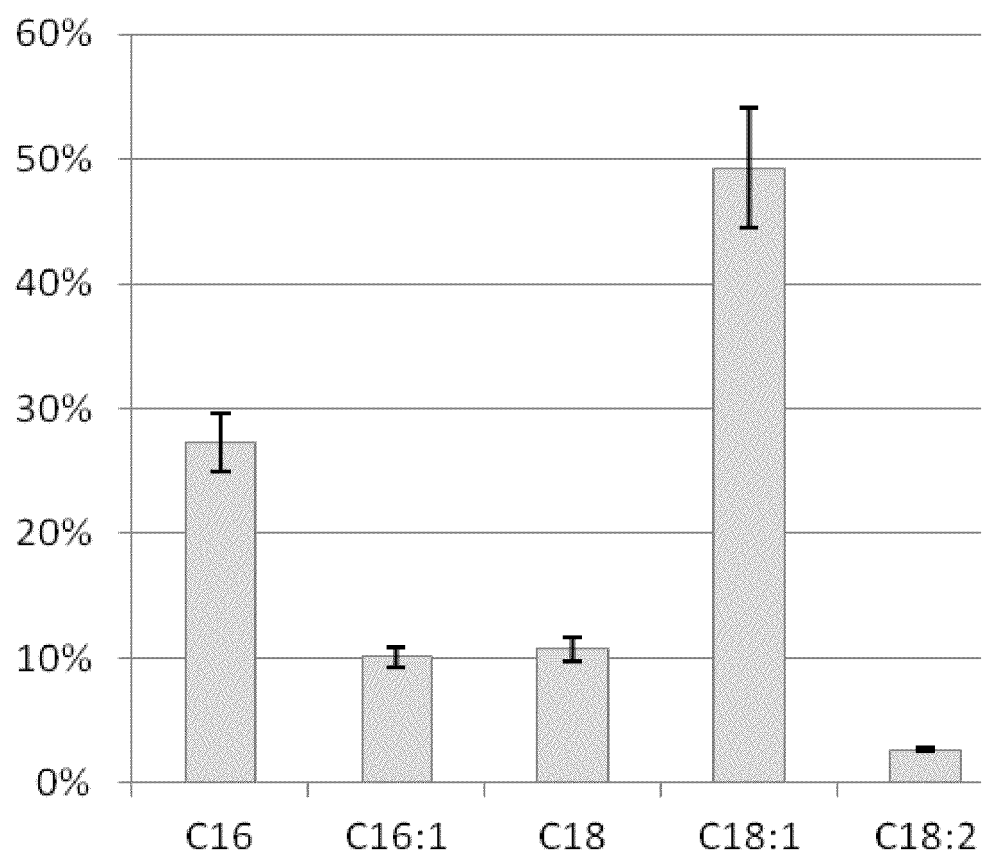
FIG. 4. Fatty Acid Profile (FAP) of ACC1+DGA1 transformant in 2-L bioreactor fermentation.
Figure 5:
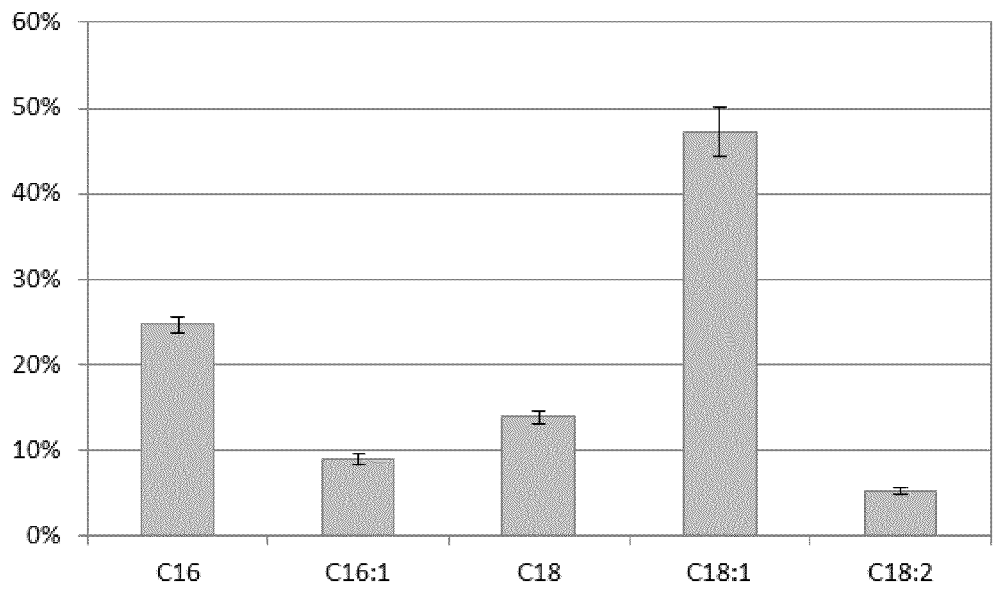
FIG. 5. Fatty acid profile of ACC+DGA transformant grown in 2-L bioreactor with acetate as carbon source.

The fatty acid profile changed dramatically during the scale up (FIG. 4). Relative depletion of stearic acid and enrichment of palmitic acid and oleic acid was observed, with oleic acid ultimately comprising 49.3% of total fatty acids. The ratio between oleic and stearic acids steadily increased throughout the fermentation (data not shown), finally ending in a ratio of 4.6. This is a dramatic change from the ratio of 1.3 seen in shake flask experiments. A similar experiment was performed with acetate as the carbon source. The fatty acid profile was analyzed at 134 hrs and the results are shown in FIG. 5.

High relative oleate concentrations (up to 58.5%) has also been observed in other 2-L fermentations (51), and is more similar to profiles of other oleaginous yeasts that accumulate more than 50% lipid content (15). In conditions of rapid lipid production, oleic acid might be more rapidly stored and easier to accumulate, as DGA1p is known to have varying specificities for different acyl-CoA; in *S. cerevisiae*, C18:1 is the most preferred substrate, having twice the activity of C18:0 (52). Furthermore, the high oleic acid concentration might also be a response to the higher aeration rate achieved in the bioreactor and not easily seen in shake flask fermentations.

The high lipid content, yield, and productivity seen in the ACC1+DGA1 strain demonstrate the innate capacity of *Y. lipolytica* to accommodate high flux through the lipid synthesis pathway. With further modifications and process optimization, *Y. lipolytica* with engineered lipid synthesis pathways can yield promising breakthroughs in the robust, efficient de novo synthesis of lipids

TABLE 3

Strains and plasmids used in this study

| Strains (host strain) | Genotype or plasmid | Source |
|---|---|---|
| *E. coli* | | |
| DH5α | fhuA2 Δ(argF-lacZ)U169 phoA glnV44 Φ80 Δ(lacZ)M15 gyrA96 recA1 relA1 endA1 thi-1 hsdR17 | Invitrogen |
| pINA1269 | JMP62-LEU | Yeastern |
| pMT010 | pINA1269 php4d::TEF | This Example |
| pMT015 | pINA1269 php4d::TEFin | This Example |
| pMT025 | hp4d-LacZ | This Example |
| pMT038 | YTEF-LacZ | This Example |
| pMT037 | YTEFin-LacZ | This Example |
| pMT013 | YTEF-ACC1 | This Example |
| pMT040 | php4d-ACC1 | This Example |
| pMT053 | YTEFin-DGA | This Example |
| pMT065 | php4d-ACC1 + YTEFin-DGA | This Example |
| *Y. lipolytica* | | |
| Po1g | MATa, leu2-270, ura3-302::URA3, xpr2-332, axp-2 | Yeastern |
| MTYL038 | MATa, leu2-270, ura3-302::URA3, xpr2-332, axp-2 TEF-LacZ-LEU2 | This Example |
| MTYL037 | MATa, leu2-270, ura3-302::URA3, xpr2-332, axp-2 TEFin-LacZ-LEU2 | This Example |
| MTYL040 | MATa, leu2-270, ura3-302::URA3, xpr2-332, axp-2 hp4d-ACC1-LEU2 | This Example |
| MTYL053 | MATa, leu2-270, ura3-302::URA3, xpr2-332, axp-2 TEFin-DGA1-LEU2 | This Example |
| MTYL065 | MATa, leu2-270, ura3-302::URA3, xpr2-332, axp-2 hp4d-ACC1 + TEFin-DGA1-LEU2 | This Example |

Production of Lipids from Acetate Using Engineered ACC+DGA Strain

*Yarrowia lipolytica* naturally grows on the organic acid acetate. Acetate is an attractive substrate as it can be produced at high yields by homoacetogenic organisms from carbon dioxide or carbon monoxide via non-photosynthetic carbon fixation pathways. Acetate enters cellular metabolic pathways in the form of acetyl-coA, which is the main precursor for lipid synthesis via acetyl-coA carboxylase (ACC). As such, the ACC+DGA strain looked to be a promising candidate for lipid production on acetate substrate, since there is a direct overexpression of an acetyl-CoA utilizing enzyme coupled with the strong driving force for lipid accumulation.

Figure 6:
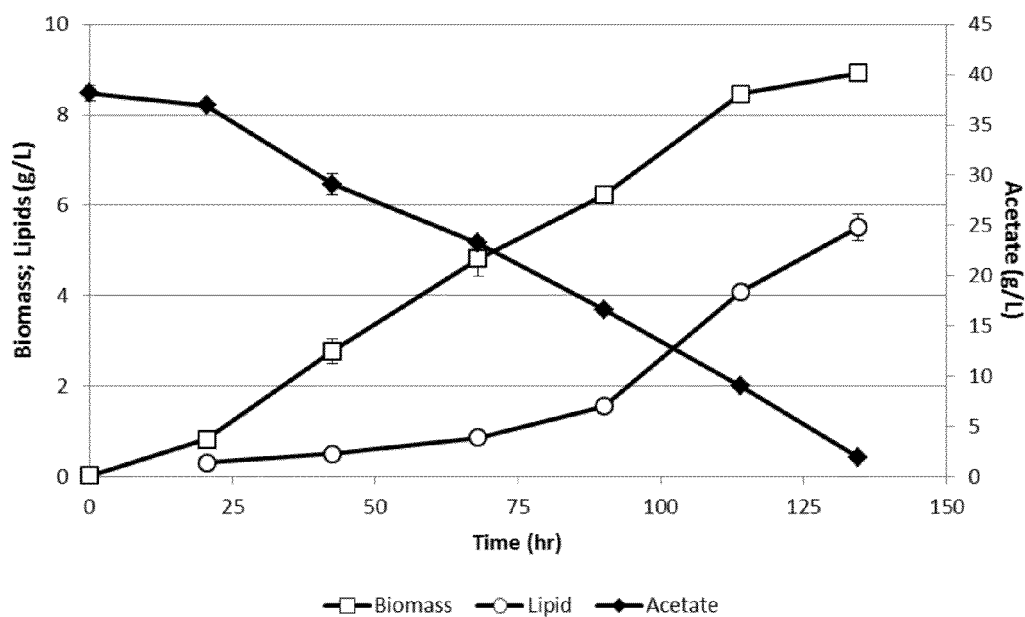
FIG. 6. Fatty acid production by ACC+DGA1 *Y. lipolytica* on acetate.

A 2-liter bioreactor fermentation was performed using the ACC+DGA strain with acetate as carbon substrate (FIG. 6). At high oxygen content, it was observed that acetate would be rapidly consumed with low biomass generation, so the fermentation was conducted under both nitrogen and oxygen-limited conditions to maximize lipid production and yield.

Final titer of oil production was 5.5 g/L after 130 hours, which constitutes 62% of the total 8.9 g/L biomass dry cell weight. The overall lipid yield on acetate was 0.152 g oil/g acetate. During the lipid production phase (between 90-130 hrs), maximum lipid production was achieved at a yield of 0.27 g oil/g acetate, which is 96% of the theoretical maximum yield.

A comparison of the fermentation characteristics to that on glucose show that despite lower biomass yields and growth rates, lipid accumulation and maximum lipid yield were commensurate.

TABLE 4

Primers used in this study

| Primer | Description | Sequence | SEQ ID |
|---|---|---|---|
| PCR | | | |
| MT078 | TEF | GACTGTCGACAGAGACCGGGTTGGCGGCGCATTTGTG | 14 |
| MT079 | TEF | GACTGGTACCTCAAGATGCATAGCACGCGTTTTGAATGATTCTTATACTC | 15 |
| MT118 | TEFin | GGCAGTCGACAGAGACCGGGTTGGCGGC | 16 |
| MT122 | TEFin | TTATTCACGCGTGTAGATACGTACTGCAAAAAGTGCTGGTCGGA | 17 |
| MT170 | LacZ | AATGACCATGATTACGGATTCACTGG | 18 |
| MT171 | LacZ | CTAGGTGGATCCTTATTTTTGACACCAGACCAACTGGTAA | 19 |
| MT172 | LacZ | TAACCGCAGACCATGATTACGGATTCACTGGCC | 20 |
| MT173 | LacZ | CTAGGTATGCATATGACCATGATTACGGATTCACTGG | 21 |
| MT174 | LacZ | CTTACAGGTACCTTATTTTTGACACCAGACCAACTGGTAA | 22 |
| MT080 | TEF-ACC | GACTACGCGTCACAATGCGACTGCAATTGA | 23 |
| MT081 | TEF-ACC | TAGCATGCATTCACAACCCCTTGAGCAGCT | 24 |
| MT222 | Hp4d-ACC | AATGCGACTGCAATTGAGGACACTAA | 25 |
| MT137 | Hp4d-ACC1 | CGTTGAATCGATTTCGGACACGGGCATCTCAC | 26 |
| MT271 | DGA | TAACCGCAGACTATCGACTCACAATACTACAAGTCGCG | 27 |
| MT272 | DGA | CTAGGTATGCATTTACTCAATCATTCGGAACTCTGGG | 28 |
| MT220 | NruI AseI | CCCGCAACAATTAATAGACTGGAT | 29 |
| MT265 | NruI AseI | TTCGGACACGGGCATCTCAC | 30 |
| RT-PCR | | | |
| | Actin | | |
| | Actin | | |
| | LacZ | | |
| | LacZ | | |
| | ACC1 | | |
| | ACC1 | | |
| | DGA | | |
| | DGA | | |

TABLE 5

Comparison of fermentation on glucose and acetate.

| | Glucose | Acetate |
|---|---|---|
| Exponential Growth Rate | 0.0982 hr$^{-1}$ | 0.0368 hr$^{-1}$ |
| Overall Biomass Yield | 0.316 g/g | 0.246 g/g |
| Overall Lipid Yield | 0.195 g/g | 0.152 g/g |
| Lipid Production Phase | 70-120 hrs | 90-130 hrs |
| Maximum Lipid Yield | 0.249 g/g | 0.270 g/g |
| Maximum Productivity | 0.258 g/L/hr | 0.103 g/L/hr |
| Final Lipid Titer | 17.6 g/L | 5.5 g/L |

Conclusions

Lipid biosynthesis is a tightly regulated metabolic pathway. For industrially-relevant applications for the production of lipids, thoughtful metabolic engineering is necessary to maximize yields and productivity. The use of the oleaginous yeast *Y. lipolytica* benefits from having high capacity for lipid accumulation and tools for engineering the lipid metabolic pathway. Here we show that the intron-enhanced co-overexpression of two important genes in the lipid synthesis pathway, ACC1 and DGA1, provides driving force towards the production of lipids even under moderate C/N ratios. As the two enzymes carry out the first and last steps of lipid synthesis, the simultaneous push and pull of carbon flux towards TAG allows for enhanced production with minimal intermediate accumulation, which can lead to inhibition. The resulting ACC1+DGA1 strain was able to accumulate up to 62% of its DCW as lipids through de novo synthesis at an overall volumetric productivity of 0.143 g/L/hr.

The concepts of (a) strong overexpression of pathway genes, (b) balance of upstream and downstream pathways, (c) diversion of flux towards desired pathways, and (d) driving forces towards the final product, are prominent strategies in the practice of metabolic engineering, where metabolic networks are engineered and optimized for the generation of desirable products. Implementation of these concepts with respect to lipid accumulation may readily extend to a number of biological platforms, including microalgae. These strategies will be foundational in enabling the technologies of robust, efficient, commodity-scale production of biologically-derived chemicals and fuels. Their application to lipid biosynthesis opens the path for microbial oil overproduction and cost-effective biofuel manufacturing.

REFERENCES

1. G. Stephanopoulos, Science 315, 801 (2007).
2. J. Hill, E. Nelson, D. Tilman, S. Polasky, D. Tiffany, Proceedings of the National Academy of Sciences 103, 11206 (2006).
3. Q. Li, W. Du, D. Liu, Applied Microbiology and Biotechnology 80, 749 (2008).
4. A. Beopoulos, J.-M. Nicaud, C. Gaillardin, Applied Microbiology and Biotechnology 90, 1193 (2011).
5. J. D. Keasling, Science 330, 1355 (Dec. 3, 2010, 2010).
6. N. M. D. Courchesne, A. Parisien, B. Wang, C. Q. Lan, Journal of Biotechnology 141, 31 (2009).
7. J. B. Ohlrogge, J. G. Jaworski, Annual Review of Plant Biology 48, 109 (1997).
8. S. Papanikolaou, L. Muniglia, I. Chevalot, G. Aggelis, I. Marc, Journal of Applied Microbiology 92, 737 (2002).
9. J. M. Beckerich, A. Boisramé-Baudevin, C. Gaillardin, International microbiology: the official journal of the Spanish Society for Microbiology 1, 123 (1998).
10. C. Scioli, L. Vollaro, Water Research 31, 2520 (1997).
11. G. Barth, C. Gaillardin, FEMS Microbiology Reviews 19, 219 (1997).
12. S. Papanikolaou, L. Muniglia, I. Chevalot, G. Aggelis, I. Marc, Current microbiology 46, 124 (2003).
13. S. Papanikolaou, G. Aggelis, Bioresource Technology 82, 43 (2002).
14. S. Papanikolaou, G. Aggelis, Current microbiology 46, 398 (2003).
15. A. Beopoulos et al., Progress in Lipid Research 48, 375 (2009).
16. K. Athenstaedt et al., Proteomics 6, 1450 (2006).
17. L. M. Blank, F. Lehmbeck, U. Sauer, FEMS Yeast Research 5, 545 (2005).
18. A. Beopoulos et al., Applied and environmental microbiology 74, 7779 (2008).
19. T. Dulermo, J.-M. Nicaud, Metabolic Engineering In Press, Corrected Proof (2011).
20. L.-T. Chuang et al., New Biotechnology 27, 277 (2010).
21. J. Sambrook, D. W. Russell, Molecular cloning: a laboratory manual (CSHL press, 2001)
22. D. C. Chen, J. M. Beckerich, C. Gaillardin, Applied Microbiology and Biotechnology 48, 232 (1997).
23. J. Folch, M. Lees, G. H. Sloane-Stanley, J. biol. Chem 226, 497 (1957).
24. C. Madzak, C. Gaillardin, J. M. Beckerich, Journal of Biotechnology 109, 63 (2004).
25. S. Müller, T. Sandal, P. Kamp Hansen, H. Dalbøge, Yeast 14, 1267 (1998).
26. C. Madzak, B. Treton, S. Blanchin-Roland, Journal of Molecular Microbiology and Biotechnology 2, 207 (2000).
27. N. Gasmi, A. Ayed, J. M. Nicaud, H. Kallel, Microbial Cell Factories 10, 38 (2011).
28. W. Cui et al., Process Biochemistry 46, 1442 (2011).
29. H. Le Hir, A. Nott, M. J. Moore, Trends in biochemical sciences 28, 215 (2003).
30. J. Callis, M. Fromm, V. Walbot, Genes & Development 1, 1183 (1987).
31. A. Furger, J. M. O. S. A. Binnie, B. A. Lee, N. J. Proudfoot, Genes & Development 16, 2792 (Nov. 1, 2002, 2002).
32. M. Ares, L. Grate, M. H. Pauling, Rna 5, 1138 (1999).
33. A. T. Ivashchenko, M. I. Tauasarova, S. A. Atambayeva, Molecular Biology 43, 24 (2009).
34. E. Bon et al., Nucleic acids research 31, 1121 (2003).
35. Y. Kamisaka, N. Tomita, K. Kimura, K. Kainou, H. Uemura, Biochem J 408, 61 (2007).
36. S. Papanikolaou et al., Current microbiology 52, 134 (2006).
37. C. Ratledge, in Single Cell Oil R. S. Moreton, Ed. (Longman Scientific & Technical, 1988) pp. 33-70.
38. R. Ruenwai, S. Cheevadhanarak, K. Laoteng, Molecular biotechnology 42, 327 (2009).
39. D. Klaus, J. B. Ohlrogge, H. E. Neuhaus, P. Dörmann, Planta 219, 389 (2004).
40. K. Roesler, D. Shintani, L. Savage, S. Boddupalli, J. Ohlrogge, Plant Physiology 113, 75 (Jan. 1, 1997, 1997).
41. R. W. Brownsey, A. N. Boone, J. E. Elliott, J. E. Kulpa, W. M. Lee, Biochemical Society Transactions 34, 223 (2006).
42. T. Kamiryo, Y. Nishikawa, M. Mishina, M. Terao, S. Numa, Proceedings of the National Academy of Sciences 76, 4390 (1979).
43. V. Andrianov et al., Plant biotechnology journal 8, 277 (2009).
44. C. R. Shen et al., Appl. Environ. Microbiol. 77, 2905 (May 1, 2011, 2011).

45. X. Liu, J. Sheng, R. Curtiss Iii, Proceedings of the National Academy of Sciences 108, 6899 (Apr. 26, 2011, 2011).
46. Y. X. Huo et al., Nature biotechnology 29, 346 (2011).
47. G. Aggelis, M. Komaitis, Biotechnology Letters 21, 747 (1999).
48. S. E. Karatay, G. Dönmez, Bioresource Technology 101, 7988 (2010).
49. Y. A. Tsigie, C.-Y. Wang, C.-T. Truong, Y.-H. Ju, Bioresource Technology In Press, Corrected Proof (2011).
50. S. Papanikolaou, I. Chevalot, M. Komaitis, I. Marc, G. Aggelis, Applied Microbiology and Biotechnology 58, 308 (2002).
51. C. H. Zhao, W. Cui, X. Y. Liu, Z. M. Chi, C. Madzak, Metabolic Engineering (2010).
52. P. Oelkers, D. Cromley, M. Padamsee, J. T. Billheimer, S. L. Sturley, Journal of Biological Chemistry 277, 8877 (2002).

Example 2

Combinatorial Expression of Lipid Synthesis Genes in Yarrowia lipolytica

The study of cellular metabolism can be elucidated using metabolic engineering. Metabolic engineering is the use of recombinant DNA technologies to manipulate metabolic pathways in organisms (Bailey 1991). Through manipulation and engineering of specific metabolic networks, controlling factors and rate-limiting steps can be identified and elaborated. Building upon existing knowledge and tools for a specific organism or pathway, one can evaluate how novel perturbations can be used to redirect and control the generation of desired products.

Lipid biosynthesis is an excellent pathway for study using for metabolic engineering, having wide applications ranging from health, cancer and medicine, to biochemicals and biofuels production (Beopoulos et al. 2011; Courchesne et al. 2009; Kohlwein and Petschnigg 2007). The physiology, enzymology, and metabolism for lipid biosynthesis in a wide range of organisms, from bacteria to humans, have been extensively studied, forming a strong knowledge base for both comparative and exploratory analysis (Kurat et al. 2006; Ohlrogge and Jaworski 1997). Lipid metabolism plays an integral role in numerous aspects of cell physiology, from cell growth and proliferation to energy storage and metabolism (Kohlwein and Petschnigg 2007; Tehlivets et al. 2007). To utilize these pathways for both medicinal and industrial purposes, it is important to understand which perturbations have the greatest impact on the overall process.

The oleaginous yeast Yarrowia lipolytica stands as an excellent model organism to study lipid metabolism. As an oleaginous yeast, Y. lipolytica can naturally accumulate up to 36% lipids in carbon rich environments (Beopoulos et al. 2009). These lipids are stored in the form of triacylglycerides (TAG) in lipid bodies. It is one of the most extensively studied 'non-conventional' yeast species, with a sequenced genome and a range of genetic tools available (Barth and Gaillardin 1997). It has been used in a number of industrial applications and has been viewed as a model organism for protein secretion, hydrophobic substrate utilization, lipid metabolism, and mitochondrial respiration (Beckerich et al. 1998; Beopoulos et al. 2009; Coelho et al. 2010; Kerscher et al. 2002). While Y. lipolytica naturally accumulates large quantities of lipids, a number of engineering efforts have been successful in further increasing or otherwise improving its lipid accumulation characteristics (Beopoulos et al. 2008; Chuang et al. 2010; Dulermo and Nicaud 2011; Zhang et al. 2011). However the number and variety of genetic manipulations examined has remained relatively limited towards this end and the potential for Y. lipolytica as a platform for lipid overproduction remains relatively unexplored.

A number of interesting gene targets have been linked to lipid accumulation through a variety of approaches and strategies (Courchesne et al. 2009). Acetyl-coA carboxylase (ACC) is generally known as the rate-limiting step in fatty biosynthesis, controlling the flux entering the pathway. It is responsible for producing malonyl-coA, which can be utilized in fatty acid elongation. ACC utilizes cytosolic acetyl-coA as its main metabolic precursor. The enzyme that supplies cytosolic acetyl-coA in most eukaryotes is ATP citrate lyase (ACL). ACL cleaves citrate, which has been shuttled out of the mitochondria as a product of the TCA cycle, to form acetyl-coA and oxaloacetate. After fatty acid production is completed with the fatty acid synthase complex, acyl-coA molecules can be further manipulated through elongation and desaturation at the endoplasmic reticulum. These processes help modify the chemical properties of the acyl-coA chains to facilitate storage or utilization in other metabolic pathways. Enzymes such as Δ9-desaturase (D9) convert stearoyl-coA molecules into oleoyl-coA molecules, which seem to be very important in both lipid regulation and metabolism (Dobrzyn and Ntambi 2005). The final step in lipid assembly and storage is the conversion of diacylglycerol (DAG) into TAG via the enzyme diacylglycerol acyltransferase (DGA). This step occurs at both the endoplasmic reticulum and on the surface of lipid bodies, with the latter establishing a dynamic equilibrium of TAG assembly and degradation depending on the energy needs of the organism (Athenstaedt et al. 2006). In Y. lipolytica, a number of DGA genes have been identified that perform this function (Zhang et al. 2011). These enzymatic steps exhibit an interesting relationship to lipid accumulation. ACC controls flux entering lipid synthesis, and overexpression of ACC in the bacteria Escherichia coli resulted in 6-fold increase in fatty acid synthesis (Davis et al. 2000). The citrate shuttle, which is under control of ACL, is differentially observed in oleaginous fungi compared to non-oleaginous fungi, and is speculated as a necessary pathway for high flux into the lipid biosynthesis pathway (Boulton and Ratledge 1981; Vorapreeda et al. 2012). It is also thought that deactivation of ACL leads to citrate accumulation and secretion, an undesirable phenomenon in lipid production (Papanikolaou and Aggelis 2002; Papanikolaou et al. 2002). D9 has been implicated in cancer metabolism, being upregulated in mammalian tumor cells. It is potentially a strong positive regulator of lipogenesis and facilitates the lipid production necessary for rapid growth found in cancer cells (Dobrzyn and Ntambi 2005; Hulver et al. 2005; Ntambi and Miyazaki 2004). DGA is the final committed step for lipid storage, and overexpression of DGA in a S. cerevisiae Δsnf2 mutant resulted in dramatic increases in lipid accumulation (Kamisaka et al. 2007). While these results have produced interesting results and implications, analysis of their contributions within a single model organism can allow us to systematically identify how they can contribute and cooperate to achieve the increased lipid production.

Here we look at the impact of several important genes involved in lipid biosynthesis and explore their contributions towards increasing lipid accumulation in the oleaginous yeast Y. lipolytica. By overexpression of gene targets, both individually and in combination, we can explore how genes can positively impact flux through lipid biosynthesis pathway. Furthermore we investigate the lipid production performance of two candidate strains to elucidate the importance of balanced metabolic flux within the cell to achieve high productivity.

Materials and Methods

Yeast Strains, Growth, and Culture Conditions

The *Y. lipolytica* strains used in this study were derived from the wild-type *Y. lipolytica* W29 strain (ATCC20460). The auxotrophic Po1g (Leu-) used in all transformations was obtained from Yeastern Biotech Company (Taipei, Taiwan). All strains used in this study are listed in Table 6. Constructed plasmids were linearized with SacII and chromosomally integrated into Po1g according to the one-step lithium acetate transformation method described by Chen et al. (Chen et al. 1997). MTYL transformants were named after the numbering of their corresponding integrated plasmids, with the exception of MTYL088 and MTYL089. For construction of strains MTYL088 and MTYL089, strains MTYL078 and MTYL079 underwent two additional rounds of transformation: (1) transformed with URA KO cassette on selective 5-FOA to knock out endogenous URA; (2) transformed with PMT092 linearized with SacII. Transformants were plated on selective media and verified by PCR of prepared genomic DNA. Verified transformants were then stored as frozen glycerol stocks at −80° C. and on selective YNB plates at 4° C. A summary of the designed overexpression of genes for each strain is described in Table 7.

Media and growth conditions for *Escherichia coli* have been previously described by Sambrook et al. (Sambrook and Russell 2001), and those for *Y. lipolytica* have been described by Barth and Gaillardin (Barth and Gaillardin 1997). Rich medium (YPD) was prepared with 20 g/L Bacto peptone (Difco Laboratories, Detroit, Mich.), 10 g/L yeast extract (Difco), 20 g/L glucose (Sigma-Aldrich, St. Louis, Mo.). YNB medium was made with 1.7 g/L yeast nitrogen base (without amino acids) (Difco), 0.69 g/L CSM-Leu (MP Biomedicals, Solon, Ohio), and 20 g/L glucose. Selective YNB plates contained 1.7 g/L yeast nitrogen base (without amino acids), 0.69 g/L CSM-Leu, 20 g/L glucose, and 15 g/L Bacto agar (Difco). Shake flask experiments were carried out using the following medium: 1.7 g/L yeast nitrogen base (without amino acids), 1.5 g/L yeast extract, and 50 g/L glucose. From frozen stocks, precultures were inoculated into YNB medium (5 mL in Falcon tube, 200 rpm, 28° C., 24 hr). Overnight cultures were inoculated into 50 mL of media in 250 mL Erlenmeyer shake flask to an optical density (A600) of 0.05 and allowed to incubate for 100 hours (200 rpm, 28° C.), after which biomass, sugar content, and lipid content were taken and analyzed.

Bioreactor scale fermentation was carried out in a 2-liter baffled stirred-tank bioreactor. The medium used contained 1.7 g/L yeast nitrogen base (without amino acids and ammonium sulfate), 2 g/L ammonium sulfate, 1 g/L yeast extract, and 90 g/L glucose. From a selective plate, an initial preculture was inoculated into YPD medium (40 mL in 250 mL Erlenmeyer flask, 200 rpm, 28° C., 24 hr). Exponentially growing cells from the overnight preculture were transferred into the bioreactor to an optical density (A600) of 0.1 in the 2-L reactor (2.5 vvm aeration, pH 6.8, 28° C., 250 rpm agitation). Time point samples were stored at −20° C. for subsequent lipid analysis. Sugar organic acid content was determined by HPLC. Biomass was determined by determined gravimetrically from samples washed and dried at 60° C. for two nights.

Genetic Techniques

Standard molecular genetic techniques were used throughout this study (Sambrook and Russell 2001). Restriction enzymes and Phusion High-Fidelity DNA polymerase used in cloning were obtained from New England Biolabs (Ipswich, Mass.). Genomic DNA from yeast transformants was prepared using Yeastar Genomic DNA kit (Zymo Research, Irvine, Calif.). All constructed plasmids were verified by sequencing. PCR products and DNA fragments were purified with PCR Purification Kit or QIAEX II kit (Qiagen, Valencia, Calif.). Plasmids used are described in Table 6. Primers used are described in Table 9.

Deletion of URA3

To increase the availability of markers in strains of *Y. lipolytica*, the gene encoding for uracil prototrophy, orotidine-5′-phosphate decarboxylase (URA3, Accession Number: AJ306421), was amplified and used as the basis of a knockout cassette for the generation of URA auxotrophic strains. Upstream and downstream sequences of the URA open reading frame were amplified using primer pairs MT310-MT311 and MT312-MT313, respectively. The primers are designed such that the two amplicons carry 23 bp overlapping region. Upon purification of the two amplicons, both products are mixed and a PCR is performed using the primers MT310 and MT313 to produce a 456 bp amplicon fusing the upstream and downstream amplicons. This DNA was purified and subsequently transformed into Po1g. Transformed cells were then plated on a selective media plate containing uracil and 5-Fluoroorotic Acid (5-FOA). Colonies which grew were replated on 5-FOA plates to reselect for URA auxotrophy, and verified by PCR of prepared genomic DNA. The resulting ΔLEU2 ΔURA3 strain was named MTYL100.

Plasmid Construction

The construction of plasmids pMT010, pMT015, pMT038, pMT040, pMT013 and pMT065 were described above, and are similar to methods described here. Plasmid pMT047 expressing ATP:citrate lyase subunit 1 was constructed by amplifying the ACL1 gene from *Y. lipolytica* Po1g genomic DNA (Accession Number: XM_504787) and inserting it into the MluI and NsiI sites of pMT010 using primers MT252 and MT253. Plasmid pMT049 expressing ATP:citrate lyase subunit 2 was likewise constructed by amplifying the ACL2 gene from *Y. lipolytica* Po1g genomic DNA (Accession Number: XM_503231) and inserting it into the MluI and NsiI sites of pMT010 using primers MT254 and MT255. Plasmid pMT061 expressing Delta-9 fatty acid desaturase (D9) was amplified from Po1g genomic DNA (Accession Number: XM_501496) and inserted into pINA1269 under control of the php4d promoter using the restriction sites PmlI and BamHI with primers MT283 and MT284.

Figure 7:
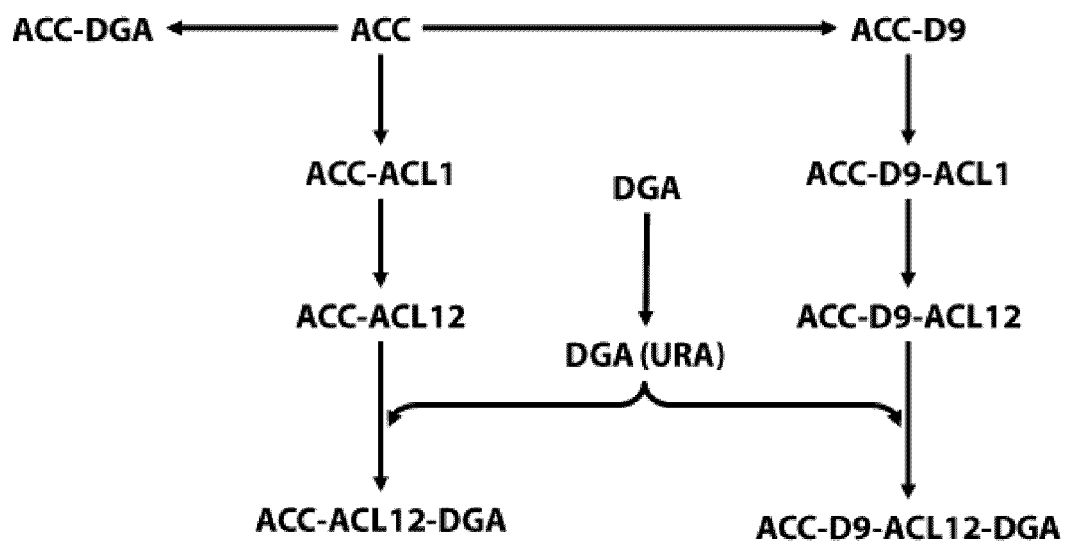
FIG. 7. Combinatorial expression construction scheme. Cloning path and strategy for construction of plasmids containing a combination of lipid accumulation gene targets. These plasmids were then transformed into *Y. lipolytica* for study of lipid accumulation.

To produce plasmids that express multiple genes (pMT050, pMT065, pMT066, pMT073, pMT074, pMT075, pMT078, pMT079), a promoter-gene-terminator cassette was amplified from one plasmid using primers MT220 and MT265. This was then digested with DpnI and AseI and inserted into a second plasmid that was digested with NruI and AseI resulting in tandem gene construct pMT065. The AseI restriction site was selected to facilitate selection, as it resides within the ampicillin resistance marker. Because NruI is a blunt end restriction site, ligation of the insertion does not increase the total number of NruI sites, thus enabling iterative insertions using the same process. The overall sequence and scheme used for the combinatorial construction of these plasmids is described in FIG. 7. For the construction of a complementary vector, pACYCDUET-1 was selected as the complementary shuttle vector, as it utilizes a different backbone, selective marker and origin of replication. The upstream sequences of LIP2 (Accession Number: XM_500282) was amplified from *Y. lipolytica* Po1g genomic DNA using the primer pairs MT316-MT317 and integrated into pDUET using the restriction sites BamHI and EcoRI. The downstream sequence of LIP2 was amplified using primer pairs MT318-MT319 and integrated into pDUET using the restriction sites KpnI and AvrII. The selective marker for yeast uracil prototrophy was amplified from the plasmid JMP62-URA using primers pairs MT314-MT315 and integrated into pDUET using the restriction sites PvuI and KpnI. The resulting plasmid pMT091 contained a multi-cloning site flanked by upstream and downstream LIP2 sequences and a URA3 marker. Digestion with the restriction enzyme SacII linearizes the plasmid and separates the integration vector from the plasmid backbone, minimizing the integration of foreign and unnecessary DNA. Use of the complementary plasmid requires construction of the expression cassette on the original pINA1269 backbone and then transferring the cassette over to pMT091 using restriction enzyme subcloning. The large multi-cloning site and differential antibiotic marker facilitate the cloning and selection process.

RNA Isolation and Transcript Quantification

Shake flask cultures grown for 42 hrs were collected and centrifuged for 5 min at 10,000 g. Each pellet was resuspended in 1.0 ml of Trizol reagent (Invitrogen) and 100 µL of acid-washed glass beads were added (Sigma-Aldrich). Tubes were vortexed for 15 min at 4° C. for cell lysis to occur. The tubes were then centrifuged for 10 min at 12,000 g at 4° C. and the supernatant was collected in a fresh 2-mL tube. 200 µL chloroform was then added and tubes were shaken by hand for 10 seconds. The tubes were again centrifuged for 10 min at 12,000 g at 4° C. 400 µL of the upper aqueous phase was transferred to a new tube, and an equal volume of phenol-chloroform-isoamyl alcohol (pH 4.7) (Ambion, Austin, Tex.) was added. Tubes were again shaken by hand for 10 seconds and centrifuged for 10 min at 12,000 g at 4° C. 250 µL of the upper phase was transferred to a new tube with an equal volume of cold ethanol and 1/10th volume sodium acetate (pH 5.2). Tubes were chilled at −20° C. for thirty minutes to promote precipitation. Tubes were then centrifuged for 5 min at 12,000 g, washed twice with 70% ethanol, dried in a 60° C. oven and finally resuspended in RNAse free water. RNA quantity was analyzed using a NanoDrop ND-1000 spectrophotometer (NanoDrop Technologies, Wilmington, Del.) and samples were stored in −80° C. freezer. qRT-PCR analyses were carried out using iScript One-step RT-PCR Kit with SYBR Green (Bio-Rad, Hercules, Calif.) using the Bio-Rad iCycler iQ Real-Time PCR Detection System. Fluorescence results were analyzed using Real-time PCR Miner and relative quantification and statistical analysis was determined with REST 2009 (Qiagen) using actin as the reference gene and MTYL038 as the reference strain (Zhao and Fernald 2005). Samples were analyzed in quadruplicate.

Lipid Extraction and Quantification

Total lipids were extracted using the procedure by Folch et al (Folch et al. 1957). A measured quantity of cell biomass (roughly 1 mg) was suspended in 1 mL of chloroform:methanol (2:1) solution and vortexed for 1 hour. After centrifugation, 500 µL was transferred to 125 µL saline solution. The upper aqueous layer was removed and the bottom layer was evaporated and resuspend in 100 µL hexane. Samples were then stored at −20° C. until transesterification.

Transesterification of total lipid extracts was performed by adding 1 mL 2% (wt/vol) sulfuric acid in methanol to each sample. Samples were then incubated at 60° C. for 2 hours. After that the samples were partially evaporated, and the fatty acid methyl esters (FAME) were extracted by adding 1 mL hexane and vortexing for 10 min. 800 µL of this hexane was then transferred into glass vials for GC analysis.

GC analysis of FAMEs was performed with a Bruker 450-GC instrument equipped with a flame-ionization detector and a capillary column HP-INNOWAX (30 m×0.25 mm). The GC oven conditions were as follows: 150° C. (1 min), a 10 min ramp to 230° C., hold at 230° C. for 2 min. The split ratio was 10:1. Fatty acids were identified and quantified by comparison with commercial FAME standards normalized to methyl tridecanoate (C13:0). Total lipid content was calculated as the sum of total fatty acid contents for five FAMEs: methyl palmitate (C16:0), methyl palmitoleate (C16:1), methyl stearate (C18:0), methyl oleate (C18:1), methyl linoleate (C18:2) (Sigma-Aldrich). The addition of tridecanoic acid to the chloroform-methanol extraction fluid was used as the internal standard, which was carried through the entire analysis procedure and transesterified into its methyl ester.

Results & Discussion

Complementary Vector Construction Allows for Alternative Method for Expression of DGA.

Figure 8:
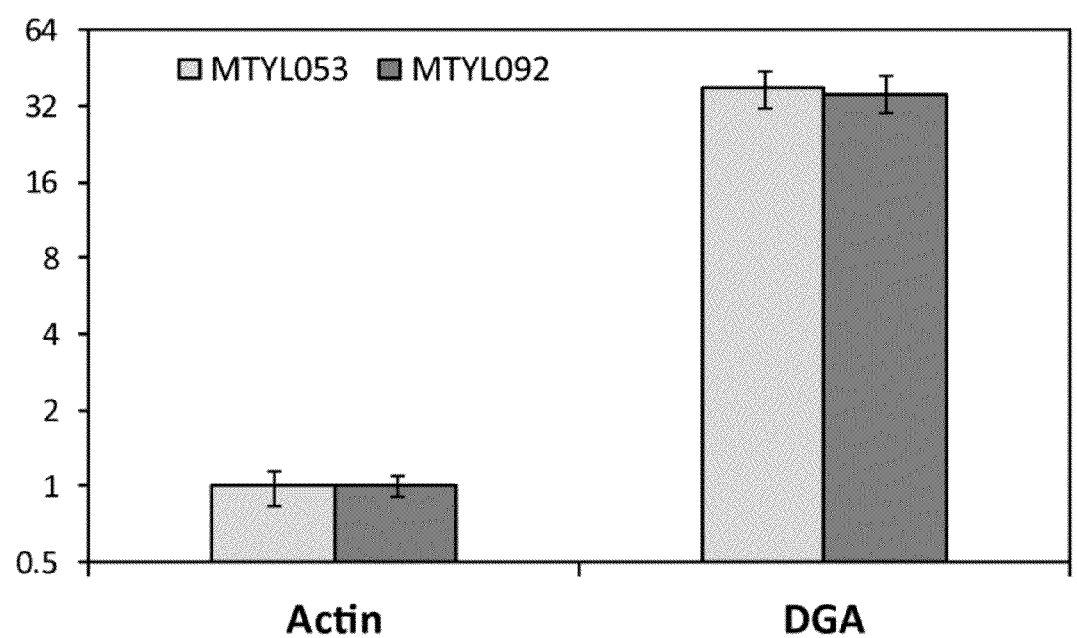
FIG. 8. Transcriptional expression of TEFin-DGA cassette when integrated via pMT053 compared to pMT092.

In order to provide an alternative and complementary method for expressing genes in *Y. lipolytica*, the URA marker was knocked out of the parent strain Po1g. As part of the design of a complementary integration vector, the extracellular lipase LIP2 gene was selected as the docking site, as this gene is well characterized and likely has a negligible or neutral effect on de novo lipid synthesis and accumulation. Thus in the process of integrating the complementary vector, LIP2 will be knocked out. Upon construction of the complementary vector for gene expression, it was necessary to examine whether the expression of a gene would be affected depending on which transformation vector was used. To test this, the gene encoding for diacylglycerol acyltransferase (DGA) was cloned into both pMT015 and pMT091 vectors. While the expression cassette was the same in both vectors, the docking site was different: a pBR322 docking site for pMT015 (and all pINA1269-based vectors), and the LIP2 gene for pMT091. Upon transformation of these vectors and verification of genomic integration, RT-PCR of extracted RNA was performed on both strains, examining the overexpression of DGA in both cases relative to a control strain (MTYL038). As shown in FIG. 8, both strains exhibit 32-fold increases in DGA expression relative to MTYL038 control strains. These results validate the use of pMT091 as a complementary vector and LIP2 as an alternative docking site for gene expression, with no detectable interference from possible epigenetic phenomena.

Full Survey of Combinatorial Constructs Identifies Improved Strains with Select Genes.

Figure 9:
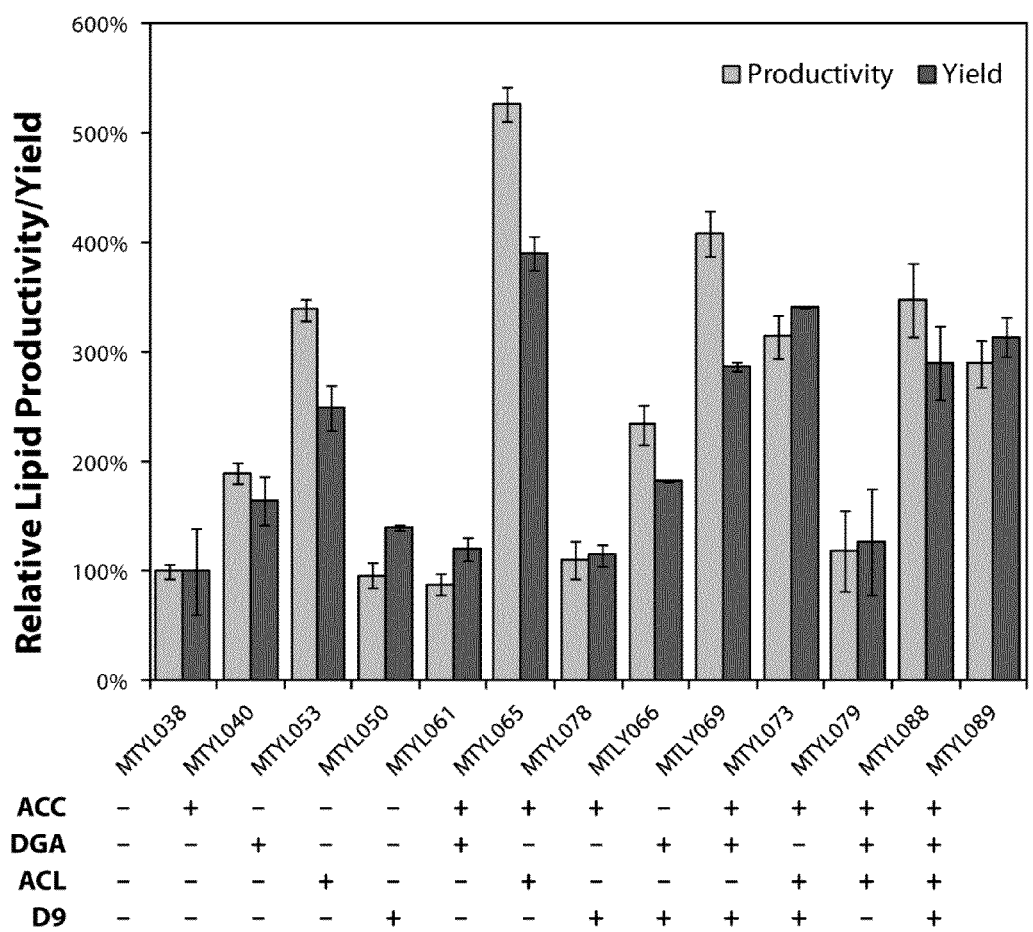
FIG. 9. Relative lipid productivity and yield among *Y. lipolytica* strains expressing combinatorial constructs, as measured by total fatty acid content normalized to the control strain. The presence (+) or absence (−) of a transformed overexpression cassette for the corresponding gene target are indicated below the graph. The productivity (light grey bars) was calculated as relative lipid accumulation within the first 100 hours of culture. Yield calculations were made by dividing lipid accumulation by sugar consumed. The C/N ratio of the media was 20. Results are averaged values across multiple experiments.

In order to investigate the contributions and interactions of the gene targets, a survey was performed across various intermediate gene expression combinations, testing for the lipid production capabilities of the transformed strains. Table 7 describes the 13 constructed strains and their corresponding gene up-regulation. Lipid measurements were all performed after 100 hrs of culture in order to compare lipid productivity rather than merely lipid accumulation. For industrial purposes, overall productivity is a more important measurement than total lipid content, as a slow growing strain producing high yields might still be less useful than a fast growing, moderately high yielding strain. The results of the complete survey of lipid productivities and yields is depicted in FIG. 9.

Examining strains containing only single gene overexpressions (MTYL040, MTYL053, MTYL050, MTYL061), ACC and DGA have clear improvements in both productivity and yield. ACL and D9 did not have any significant increases in either productivity or yield. These results indicate that for *Y.*

*lipolytica*, ACC and DGA exhibit control over lipid biosynthesis and are rate-limiting steps, while ACL and D9 do not exhibit similar phenomena.

The effects of ACC and DGA were discussed in depth above, but DGA creates driving force by sequestering lipids and depleting acyl-coA intermediates, while ACC increases yields by diverting flux towards lipid synthesis and mobilizing the cytosolic acetyl-coA pool more rapidly. When the two genes are combined in strain MTYL065, they produce a synergistic response by establishing a push-and-pull dynamic within the lipid synthesis pathway, with acyl-coA as the balanced intermediate.

When combined with other genes, the gene D9 was able to confer slight benefits to the lipid productivity. For example, MTYL069, overexpressing D9 and DGA, had higher lipid productivities than MTYL053, which contained only DGA overexpression. Likewise, MTYL066, overexpressing ACC and D9, had higher lipid productivities than MTYL040, overexpressing ACC alone. However, MTYL073, overexpressing ACC+D9+DGA, exhibited lower lipid productivity than MTYL065. There were no significant differences between MTYL089 and its D9-lacking variant, MTYL088. While some benefits were observed for accumulation and productivity, the benefits for yield were not significant. The observation that D9 only improves lipid production in combination with other genes seems to suggest that D9 does not have strong regulatory or rate-limiting control over the lipid synthesis process, but its enzymatic action provides favorable conditions magnifying the effect of other genes. As a membrane-associated enzyme on the lipid body membrane and endoplasmic reticulum, D9 is upregulated during lipid accumulation phases (Morin et al. 2011). Many lipid synthesis enzymes have been found to have the highest specificities for oleate, which is the product of D9 desaturation (Oelkers et al. 2002). This is also demonstrated in the observation that *Y. lipolytica* grows very rapidly on oleate as a carbon source and has extensively been studied growing off of this substrate (Beopoulos et al. 2008; Fickers et al. 2005). Consequently, an increased concentration of oleate, while not specifically driving lipid production or yield, transforms the fatty acid pool to be more rapidly sequestered. This ultimately results in faster rates of lipid accumulation without increases in yield, as increased sequestration will only occur in situations where lipid synthesis has already upregulated by other manipulations.

In contrast, when combining ACL overexpression with other genes, lipid productivity tended to decrease. MTYL078 and MTYL079 exhibited no significant increases in lipid production, despite overexpressing ACC and/or D9. MTYL088, harboring ACC+ACL+DGA, increased lipid production over control, but did not exhibit any lipid production improvements over MTYL065. These results indicate that while ACL may be affecting the distribution of carbon flux throughout the metabolic network, the overexpression of ACL, whether independently or in combination with other lipogenic improvements, does not significantly promote lipid production and in most cases lowers lipid productivity. This is similar to the observation that while ATP citrate lyase is an enzyme differentially expressed in oleaginous yeast compared to non-oleaginous yeast, the activity of the gene in various organisms has no correlation with the measured oleaginicity (Boulton and Ratledge 1981).

Another observation from the lipid survey is that expression of DGA along with multiple other targets typically resulted in similar responses, both in productivity and yield. While it is possible that there is some saturation in expression or activity occurring in these constructs, this plateaued response may also have been due to a limitation of the experiment used, as the measured characteristic in this survey was initial overall productivity, rather than stationary phase lipid accumulation or productivity. Furthermore, while strain MTYL065 clearly demonstrated the strongest productivity, the yield was relatively similar to many of the plateaued strains. This suggests that while all of these strains successfully divert flux towards lipids, giving increased yields, MTYL065 is exceptional in its balance of upstream and downstream pathways to achieve both high productivity and yield. These results highlight the importance of balancing perturbations to the metabolic flux network in order to achieve optimal productivities and yields, which is a common theme in metabolic engineering for growth-coupled products (Feist et al. 2010; Tyo et al. 2007).

RT-PCR Analysis of Full Construct Shows Overexpression in MTYL089.

Figure 10:
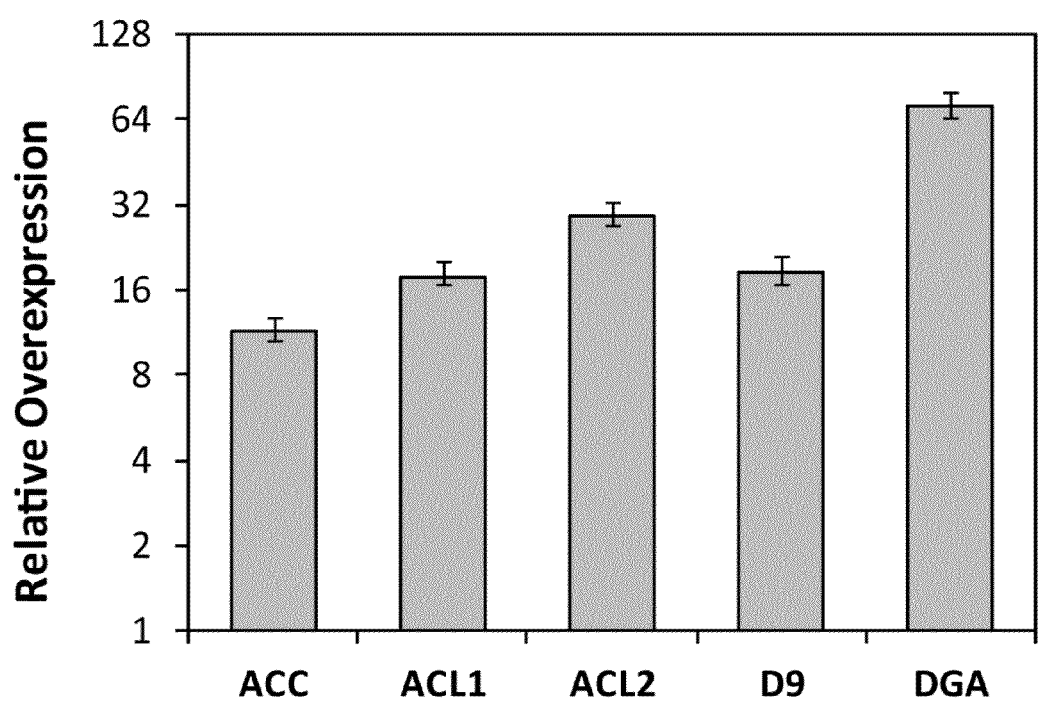
FIG. 10. Transcriptional expression of target genes in the strain MTYL089. Expression is internally normalized to actin expression, and compared against a control (MTYL038) strain and was taken after 66 hours of growth.

To explore the plateaued region of the lipid survey, the strain MTYL089, overexpressing ACC+D9+ACL12+DGA, was further investigated. The strain was constructed from the transformation of two plasmids, pMT079 and pMT092, into the ΔLEU and ΔURA MTYL100 background strain of *Y. lipolytica*. The use of two plasmids was primarily due to plasmid size considerations, as pMT079 already included four tandem expression cassettes and was 23 kb in length. PCR of genomic DNA confirmed the successful integration of both plasmids into the strain, with confirmation of correct integration of each individual expression cassette. RT-PCR analysis of the completed and verified strain relative to the control strain confirmed proper transcriptional overexpression of all five genes (FIG. 10). The strong overexpression of DGA, which was the only gene under TEFin expression, demonstrates the enhancement characteristics of the spliceosomal intron even with the potential competition from numerous cassettes utilizing the same promoter. ACC, which was under control of the intronless TEF promoter, showed the lowest expression. The two subunits of ACL, also under control of a TEF promoter, exhibited higher expression than D9, which was under control of an hp4d promoter. Since sampling occurred well after exponential growth phase (where hp4d can exhibit quasi-growth dependent expression (Madzak et al. 2000)), the constitutive expression of the hp4d and TEF all seem to be relatively close to each other. These results show sufficient overexpression of the targeted genes.

2-L Fermentation of MTYL089 Demonstrates Strong Lipid Accumulation Capacity.

Figure 11:
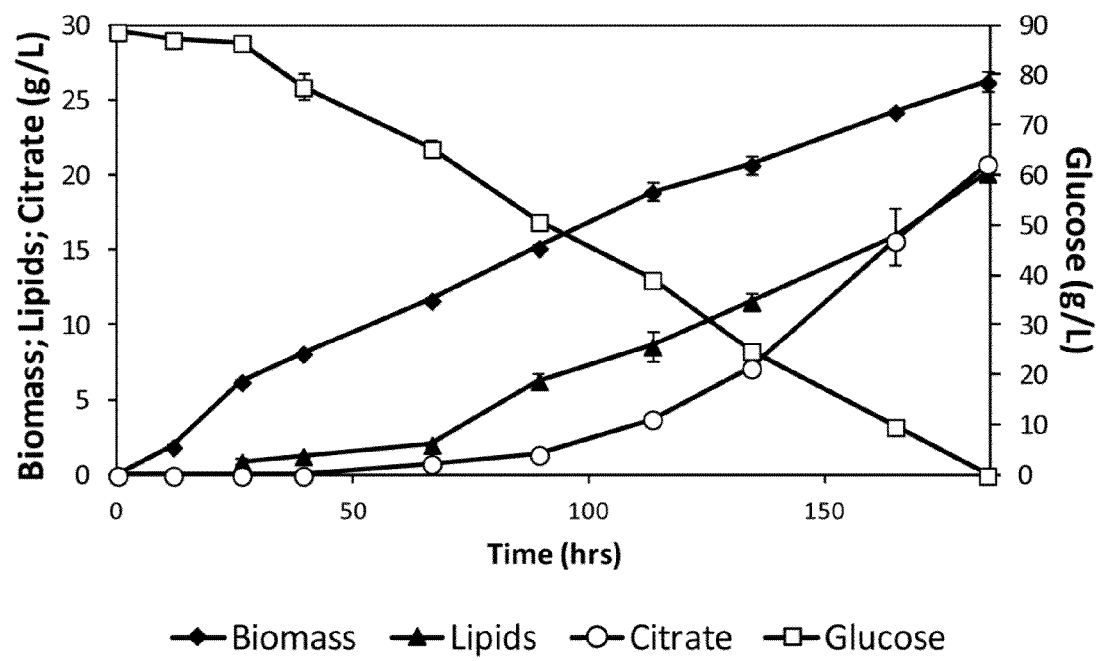
FIG. 11. Batch bioreactor fermentation of strain MTYL089, overexpression ACC, D9, ACL12 and DGA. C/N molar ratio was 100. All sampling was performed in triplicate.

After verification of gene expression in the strain MTYL089, the lipogenic performance of the strain was tested in a 2-L bioreactor fermentation. The C/N ratio of the media was adjusted to 100 to help promote lipid accumulation. The C/N ratio determines the amount of excess carbon available in the fermentation once nitrogen has been depleted, and often requires delicate balancing to optimize lipid production over citrate production (Beopoulos et al. 2009). FIG. 11 shows the time profile for the duration of the batch fermentation. After 185 hrs of fermentation, all 90 g/L of glucose is consumed, yielding 26 g/L of biomass (dry cell weight) and a remarkable 76.8% lipid content for a productivity of 0.109 g lipids/L/hr. The overall yield of lipids on glucose was 0.227 g lipids/g glucose, which is 70% of the theoretical maximum yield. During the lipid accumulation phase, from 66 to 185 hrs, a maximum in lipid productivity and yield were achieved, at 0.154 g lipids/L/hr and 0.277 g lipids/g glucose, respectively, with the yield increasing to 85% of the maximum theoretical yield.

Figure 12:
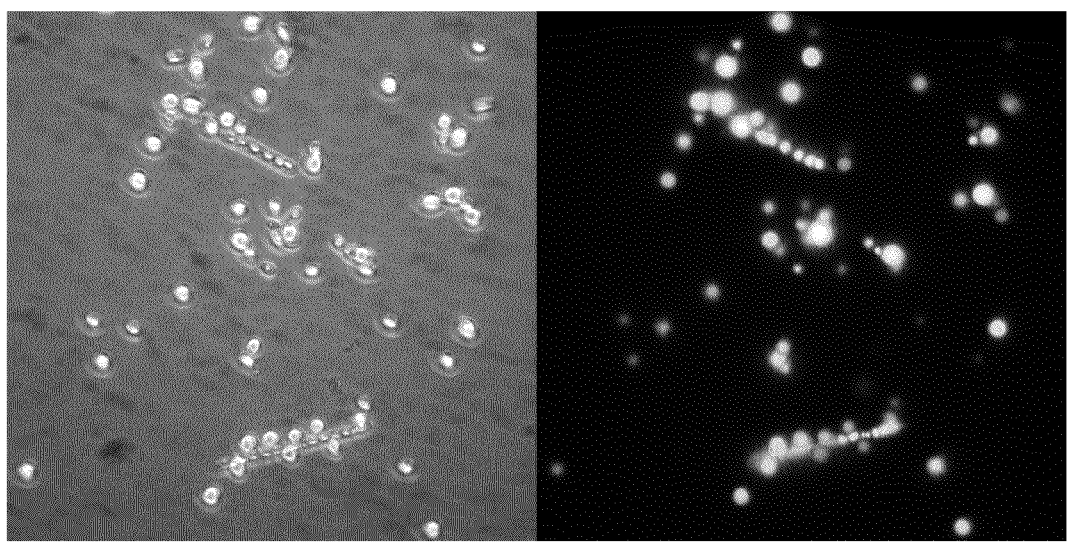
FIG. 12. Microscopy of strain MTYL089 at the end of 2-L fermentation. Normal light microscopy (image left) shows that a majority of the cells are in the yeast form, and contain large vacuoles. Fluorescence microscopy (image right) indicates that these vacuoles are composed of neutral lipids.

Microscopy of the cell culture, shown in FIG. 12, at the end of the fermentation shows that all the cells contain large vacuoles that occupy virtually the entire volume of the cell. Nile red staining and fluorescence indicates that the vacuoles are predominantly composed of neutral lipids. Even the few hyphal cells, which typically are less productive (Coelho et al. 2010), exhibit significant lipid accumulation producing multiple lipid bodies along the length of the cell.

Despite the dramatic accumulation of lipids observed in the culture, a number of characteristics were found to be undesirable, particularly in comparison with previous work using MTYL065. Firstly, there was a significant amount of citrate production occurring concomitantly with lipid production beginning at 75 hrs. Citrate is an intermediate of the lipid biosynthesis pathway, utilizing ATP citrate lyase for the enzymatic conversion to oxaloacetate and the lipogenic precursor acetyl-coA. Despite the overexpression of both ACL enzymes in the MTYL089 strain, the accumulation of citrate was still observed. It is possible that the C/N ratio was too high, which has been shown to lead to citrate production instead of lipid production (Beopoulos et al. 2009); however, our results show both citrate and lipids being produced simultaneously. This coupled production of both products differs from a discrete lipid production phase followed by a citrate production phase observed in experiments with strain MTYL065. Furthermore, the C/N ratio was matched to the batch fermentation of MTYL065, which did not show this large amount of citrate production. This indicates that it is more likely that inadequate amounts of ATP generation under the fermentation conditions, combined with high upstream flux into the pathway, led to accumulation of the intracellular citrate pool, ultimately leading to secretion. Additionally, a significantly lower productivity was observed in MTYL089. Since aeration is kept constant throughout the fermentation, oxygen-limited growth is expected in the latter stages of the fermentation. However, the onset of linear growth occurred much earlier in this fermentation than with MTYL065, occurring only after one day when the biomass concentration reached approximately 6 g/L. The earlier onset of linear growth resulted in a longer fermentation time, and thus lower productivity despite the higher lipid content. Because the aeration was also matched to the fermentation conditions of MTYL065, it is likely that the metabolic changes of MTYL089 are putting greater limitations on growth. On the other hand, MTYL089 exhibited better overall lipid yield, 0.227 g/g compared to 0.195 g lipid/g glucose in MTYL065. It also ended the fermentation with a higher titer, 20.2 g/L lipids, compared to 17.6 g/L.

Figure 13:
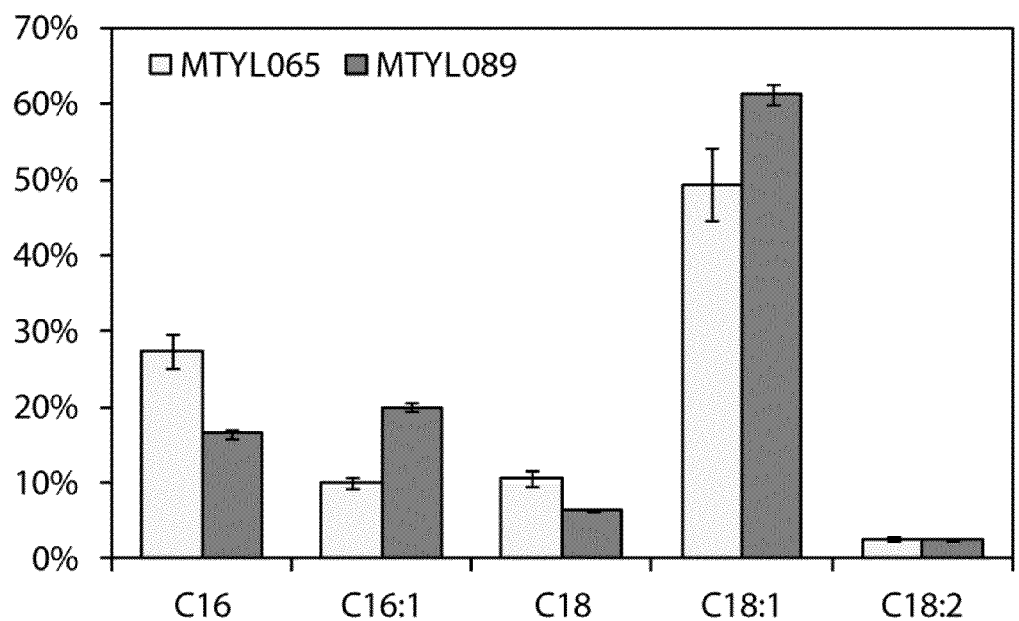
FIG. 13. Comparison of fatty acid profiles between strains MTYL065 and MTYL089. Fatty acid profiles taken from final time point in the respective fermentations, normalizing to the total fatty acid content.

Table 8 summarizes the comparison of key performance characteristics between 2-L fermentations of strain MTYL065 and MTYL089. Comparison of the fatty acid profiles (FIG. 13) indicates only slight changes in the distribution of fatty acids between the strains, having stronger preference for the monounsaturated fatty acids palmitoleate and oleate. The additional effects of ACL and D9 overexpression appear to increase the flux towards lipid synthesis, but at a considerable cost to growth rate. Additionally, since there is no matching increase in ATP generation by the cell metabolism, citrate is secreted as a byproduct rather than utilized in the lipid synthesis pathway. Since lipid synthesis and storage can strongly compete with growth for resources, tight regulation is normally necessary to manage this activity (Tehlivets et al. 2007). Overexpression of these four gene targets has unlocked a great deal of this regulation, and as a result we are observing strong competition between prioritization of cellular growth and lipid production. As a common theme in metabolic engineering, maximizing production of a particular product often requires balancing the flux towards the desired product and the overall health and growth of the organism. The contrasts between MTYL065 and MTYL089 clearly demonstrate this need, with MTYL065 exemplifying more optimized flux through the lipid synthesis pathway.

Conclusion

While the components of the lipid biosynthesis are well-understood, there is still a great deal unknown about how gene perturbations, particularly in combination, affect the capacity and flux through this pathway. By studying the oleaginous yeast *Y. lipolytica*, we are able to utilize a host organism with natural capacity for lipid production to study the extent to which metabolic engineering can improve lipid productivity and yield. We examine four gene targets—ACC, D9, ACL, DGA—and are able to achieve a remarkable 76.8% lipid content in a 2-L bioreactor with a strain carrying all four target overexpressions. By further investigation of these gene targets through combinatorial overexpression, we were able to rank the positive impact of these genes on lipid production, with DGA and ACC being strong positive contributors, D9 making slight contributions only when combined with other genes, and finally ACL making no significant positive contributions. We were also able to explore possible interactions between the individual effects, identifying the strongest synergistic interaction between ACC and DGA. The production of microbial lipids has a wide range of uses, and has fast gained attention for its utilization in the production of biodiesel. Metabolic engineering of the central pathways of lipid synthesis will be critical in providing success in enabling these future technologies and processes.

REFERENCES

Athenstaedt K, Jolivet P, Boulard C, Zivy M, Negroni L, Nicaud J M, Chardot T. 2006. Lipid particle composition of the yeast *Yarrowia lipolytica* depends on the carbon source. Proteomics 6(5):1450-1459.

Bailey J E. 1991. Toward a science of metabolic engineering. Science 252(5013):1668-1675.

Barth G, Gaillardin C. 1997. Physiology and genetics of the dimorphic fungus *Yarrowia lipolytica*. FEMS Microbiol. Rev. 19(4):219-237.

Beckerich J M, Boisramé-Baudevin A, Gaillardin C. 1998. *Yarrowia lipolytica*: a model organism for protein secretion studies. International Microbiology 1(2):123.

Beopoulos A, Cescut J, Haddouche R, Uribelarrea J L, Molina-Jouve C, Nicaud J M. 2009. *Yarrowia lipolytica* as a model for bio-oil production. Progress in Lipid Research 48(6):375-387.

Beopoulos A, Mrozova Z, Thevenieau F, Le Dall M T, Hapala I, Papanikolaou S, Chardot T, Nicaud J M. 2008. Control of lipid accumulation in the yeast *Yarrowia lipolytica*. Appl. Environ. Microbiol. 74(24):7779.

Beopoulos A, Nicaud J-M, Gaillardin C. 2011. An overview of lipid metabolism in yeasts and its impact on biotechnological processes. Appl. Microbiol. Biotechnol. 90(4):1193-1206.

Boulton C A, Ratledge C. 1981. Correlation of Lipid Accumulation in Yeasts with Possession of ATP: Citrate Lyase. Journal of General Microbiology 127(1):169-176.

Chen D C, Beckerich J M, Gaillardin C. 1997. One-step transformation of the dimorphic yeast *Yarrowia lipolytica*. Appl. Microbiol. Biotechnol. 48(2):232-235.

Chuang L-T, Chen D-C, Nicaud J-M, Madzak C, Chen Y-H, Huang Y-S. 2010. Co-expression of heterologous desaturase genes in *Yarrowia lipolytica*. New Biotechnology 27(4):277-282.

Coelho M A Z, Amaral P F F, Belo I. Current Research, Technology and Education Topics in Applied Microbiology and Microbial Biotechnology; 2010. Formatex Research Center. p 930-944.

Courchesne N M D, Parisien A, Wang B, Lan C Q. 2009. Enhancement of lipid production using biochemical, genetic and transcription factor engineering approaches. J. Biotechnol. 141(1-2):31-41.

Davis M S, Solbiati J, Cronan Jr. J E. 2000. Overproduction of Acetyl-CoA Carboxylase Activity Increases the Rate of Fatty Acid Biosynthesis in *Escherichia coli*. J. Biol. Chem. 275(37):28593-28598.

Dobrzyn A, Ntambi J M. 2005. The role of stearoyl-CoA desaturase in the control of metabolism. Prostaglandins Leukot Essent Fatty Acids 73(1):35-41.

Dulermo T, Nicaud J-M. 2011. Involvement of the G3P shuttle and β-oxidation pathway in the control of TAG synthesis and lipid accumulation in *Yarrowia lipolytica*. Metab. Eng. 13(5):482-491.

Feist A M, Zielinski D C, Orth J D, Schellenberger J, Herrgard M J, Palsson B O. 2010. Model-driven evaluation of the production potential for growth-coupled products of *Escherichia coli*. Metab Eng 12(3):173-186.

Fickers P, Benetti P H, Wache Y, Marty A, Mauersberger S, Smit M S, Nicaud J M. 2005. Hydrophobic substrate utilisation by the yeast *Yarrowia lipolytica*, and its potential applications. FEMS Yeast Res. 5(6-7):527-543.

Folch J, Lees M, Sloane-Stanley G H. 1957. A simple method for the isolation and purification of total lipids from animal tissues. The Journal of Biological Chemistry 226(1):497-509.

Hulver M W, Berggren J R, Carper M J, Miyazaki M, Ntambi J M, Hoffman E P, Thyfault J P, Stevens R, Dohm G L, Houmard J A and others. 2005. Elevated stearoyl-CoA desaturase-1 expression in skeletal muscle contributes to abnormal fatty acid partitioning in obese humans. Cell Metab 2(4):251-261.

Kamisaka Y, Tomita N, Kimura K, Kainou K, Uemura H. 2007. DGA1 (diacylglycerol acyltransferase gene) overexpression and leucine biosynthesis significantly increase lipid accumulation in the Δsnf2 disruptant of *Saccharomyces cerevisiae*. Biochemal Journal 408(1):61-68.

Kerscher S, Drose S, Zwicker K, Zickermann V, Brandt U. 2002. *Yarrowia lipolytica*, a yeast genetic system to study mitochondrial complex I. Biochim Biophys Acta 1555(1-3):83-91.

Kohlwein S, Petschnigg J. 2007. Lipid-induced cell dysfunction and cell death: Lessons from yeast. Current Hypertension Reports 9(6):455-461.

Kurat C F, Natter K, Petschnigg J, Wolinski H, Scheuringer K, Scholz H, Zimmermann R, Leber R, Zechner R, Kohlwein S D. 2006. Obese Yeast: Triglyceride Lipolysis Is Functionally Conserved from Mammals to Yeast. J. Biol. Chem. 281(1):491-500.

Madzak C, Tréton B, Blanchin-Roland S. 2000. Strong hybrid promoters and integrative expression/secretion vectors for quasi-constitutive expression of heterologous proteins in the yeast *Yarrowia lipolytica*. J. Mol. Microbiol. Biotechnol. 2(2):207-216.

Morin N, Cescut J, Beopoulos A, Lelandais G, Le Berre V, Uribelarrea J-L, Molina-Jouve C, Nicaud J-M. 2011. Transcriptomic Analyses during the Transition from Biomass Production to Lipid Accumulation in the Oleaginous Yeast *Yarrowia lipolytica*. PLoS ONE 6(11):e27966.

Nicaud J-M, Madzak C, van den Broek P, Gysler C, Duboc P, Niederberger P, Gaillardin C. 2002. Protein expression and secretion in the yeast *Yarrowia lipolytica*. FEMS Yeast Res. 2(3):371-379.

Ntambi J M, Miyazaki M. 2004. Regulation of stearoyl-CoA desaturases and role in metabolism. Prog Lipid Res 43(2): 91-104.

Oelkers P, Cromley D, Padamsee M, Billheimer J T, Sturley S L. 2002. The DGA1 gene determines a second triglyceride synthetic pathway in yeast. J. Biol. Chem. 277(11):8877.

Ohlrogge J B, Jaworski J G. 1997. Regulation of fatty acid synthesis. Annu. Rev. Plant Biol. 48(1):109-136.

Papanikolaou S, Aggelis G. 2002. Lipid production by *Yarrowia lipolytica* growing on industrial glycerol in a single-stage continuous culture. Bioresour. Technol. 82(1):43-49.

Papanikolaou S, Muniglia L, Chevalot I, Aggelis G, Marc I. 2002. *Yarrowia lipolytica* as a potential producer of citric acid from raw glycerol. Journal of Applied Microbiology 92(4):737-744.

Sambrook J, Russell D W. 2001. Molecular cloning: a laboratory manual: CSHL press. Tehlivets O, Scheuringer K, Kohlwein S D. 2007. Fatty acid synthesis and elongation in yeast. Biochimica et Biophysica Acta (BBA)—Molecular and Cell Biology of Lipids 1771(3):255-270.

Tyo K E, Alper H S, Stephanopoulos G N. 2007. Expanding the metabolic engineering toolbox: more options to engineer cells. Trends Biotechnol. 25(3):132-137.

Vorapreeda T, Thammarongtham C, Cheevadhanarak S, Laoteng K. 2012. Alternative routes of acetyl-CoA synthesis identified by comparative genomic analysis: involvement in the lipid production of oleaginous yeast and fungi. Microbiology 158(1):217-228.

Zhang H, Damude H G, Yadav N S. 2011. Three diacylglycerol acyltransferases contribute to oil biosynthesis and normal growth in *Yarrowia lipolytica*. Yeast 1:25-38.

Zhao S, Fernald R D. 2005. Comprehensive Algorithm for Quantitative Real-Time Polymerase Chain Reaction. Journal of Computational Biology 12(8):1047-1064.

TABLE 6

Strains and plasmids used in this study

| Strains (host strain) | Genotype or plasmid | Source |
|---|---|---|
| *E. coli* | | |
| NEB10β | araD139 Δ(ara-leu)7697 fhuA lacX74 galK (φ80 Δ(lacZ)M15) mcrA galU recA1 endA1 nupG rpsL (StrR) Δ(mrr-hsdRMS-mcrBC) | New England Biolabs |
| pINA1269 | JMP62-LEU | Yeastern |
| pDUET1 | pACYCDUET-1 | Novagen |
| JMP-URA | JMP62-URA | (Nicaud et al. 2002) |
| pMT010 | pINA1269 php4d::TEF | Example 1 |
| pMT015 | pINA1269 php4d::TEFin | Example 1 |

TABLE 6-continued

Strains and plasmids used in this study

| Strains (host strain) | Genotype or plasmid | Source |
|---|---|---|
| pMT038 | YTEF-LacZ | Example 1 |
| pMT013 | YTEF-ACC1 | Example 1 |
| pMT040 | php4d-ACC1 | Example 1 |
| pMT047 | YTEF-ACL1 (LEU) | This Example |
| pMT049 | YTEF-ACL2 (LEU) | This Example |
| pMT050 | YTEF-ACL1 + YTEF-ACL2 (LEU) | This Example |
| pMT053 | YTEFin-DGA | Example 1 |
| pMT061 | php4d-D9 (LEU) | This Example |
| pMT065 | php4d-ACC1 + YTEFin-DGA | Example 1 |
| pMT066 | YTEF-ACC + YLEX-D9 (LEU) | This Example |
| pMT073 | YTEF-ACC + YLEX-D9 + YTEFin-DGA (LEU) | This Example |
| pMT074 | YTEF-ACC + YTEF-ACL1 (LEU) | This Example |
| pMT075 | YTEF-ACC + YLEX-D9 + YTEF-ACL1 (LEU) | This Example |
| pMT078 | YTEF-ACC + YTEF-ACL1 + YTEF-ACL2 (LEU) | This Example |
| pMT079 | YTEF-ACC + YLEX-D9 + YTEF-ACL1 + YTEF-ACL2 (LEU) | This Example |
| pMT091 | pACYC Lip2 KO plasmid (URA) | This Example |
| pMT092 | YTEFin-DGA (URA) | This Example |
| *Y. lipolytica* | | |
| Po1g | MATa, leu2-270, ura3-302::URA3, xpr2-332, axp-2 | Yeastern |
| MTYL038 | MATa, leu2-270, ura3-302::URA3, xpr2-332, axp-2 TEF-LacZ-LEU2 | Example 1 |
| MTYL040 | MATa, leu2-270, ura3-302::URA3, xpr2-332, axp-2 hp4d-ACC1-LEU2 | Example 1 |
| MTYL050 | MATa, leu2-270, ura3-302::URA3, xpr2-332, axp-2 TEF-ACL1 + TEF-ACL2 | This Example |
| MTYL053 | MATa, leu2-270, ura3-302::URA3, xpr2-332, axp-2 TEFin-DGA1-LEU2 | Example 1 |
| MTYL065 | MATa, leu2-270, ura3-302::URA3, xpr2-332, axp-2 hp4d-ACC1 + TEFin-DGA1-LEU2 | Example 1 |
| MTYL066 | MATa, leu2-270, ura3-302::URA3, xpr2-332, axp-2 TEF-ACC + hp4d-D9 | This Example |
| MTYL073 | MATa, leu2-270, ura3-302::URA3, xpr2-332, axp-2 TEF-ACC + hp4d-D9 + TEFin-DGA1 | This Example |
| MTYL078 | MATa, leu2-270, ura3-302::URA3, xpr2-332, axp-2 TEF-ACC + TEF-ACL1 + TEF-ACL2 | This Example |
| MTYL079 | MATa, leu2-270, ura3-302::URA3, xpr2-332, axp-2 TEF-ACC + hp4d-D9 + TEF-ACL1 + TEF-ACL2 | This Example |
| MTYL088 | MATa, leu2-270, ura3-302::URA3, xpr2-332, axp-2 TEF-ACC + TEF-ACL1 + TEF-ACL2 + TEFin-DGA | This Example |
| MTYL089 | MATa, leu2-270, ura3-302::URA3, xpr2-332, axp-2 TEF-ACC + hp4d-D9 + TEF-ACL1 + TEF-ACL2 + TEFin-DGA | This Example |
| MTYL092 | MATa, leu2-270, ura3-302::URA3, xpr2-332, axp-2 LIP2::TEFin-DGA | This Example |

TABLE 7

List of all strains examined for lipid accumulation, labeled with the presence (+) or absence (−) of overexpression cassettes for the four targets: acetyl-coA carboxylase (ACC), diacylglycerol acyltransferase (DGA), ATP: citrate lyase (ACL12), and Δ9-desaturase (D9).

| Plasmid | ACC | DGA | ACL | D9 | Number of Targets |
|---|---|---|---|---|---|
| MTYL038 | − | − | − | − | 0 |
| MTYL040 | + | − | − | − | 1 |
| MTYL053 | − | + | − | − | 1 |
| MTYL050 | − | − | + | − | 1 |
| MTYL061 | − | − | − | + | 1 |
| MTYL065 | + | + | − | − | 2 |
| MTYL078 | + | − | + | − | 2 |
| MTYL066 | + | − | − | + | 2 |
| MTYL069 | − | + | − | + | 2 |
| MTYL073 | + | + | − | + | 3 |
| MTYL079 | + | − | + | + | 3 |
| MTYL088 | + | + | + | − | 3 |
| MTYL089 | + | + | + | + | 4 |

TABLE 8

Comparison of fermentation characteristics between strains MTYL065 and MTYL089. C/N ratio of both fermentations were 100, performed in 2-L bioreactors. Glucose reactor initially charged with 90 g/L glucose.

| | MTYL065 | MTYL089 |
|---|---|---|
| Overall Biomass Yield | 0.316 g/g | 0.295 g/g |
| Overall Lipid Yield | 0.195 g/g | 0.227 g/g |
| Overall Productivity | 0.143 g/L/hr | 0.109 g/L/hr |
| Lipid Production Phase | 70-120 hrs | 66-185 hrs |
| Maximum Lipid Yield | 0.249 g/g | 0.277 g/g |
| Maximum Productivity | 0.178 g/L/hr | 0.154 g/L/hr |
| Final Lipid Titer | 17.6 g/L | 20.2 g/L |

Primers used in this study. Relevant restriction sites are in bold.

| Primer | Description | Sequence | SEQ ID |
|---|---|---|---|
| PCR | | | |
| MT252 | ACL1 | CTTACAACGCGTATGTCTGCCAACGAGAACATCTCC | 31 |
| MT253 | ACL1 | CTAGGTATGCATCTATGATCGAGTCTTGGCCTTGGA | 32 |
| MT254 | ACL2 | CTTACAACGCGTATGTCAGCGAAATCCATTCACGA | 33 |
| MT255 | ACL2 | CTAGGTATGCATTTAAACTCCGAGAGGAGTGGAAGC | 34 |
| MT283 | D9 | AATGGTGAAAAACGTGGACCAAGTG | 35 |
| MT284 | D9 | CTCACAGGATCCCTAAGCAGCCATGCCAGACATACC | 36 |
| MT220 | Cassette | CCCGGCAACAATTAATAGACTGGAT | 37 |
| MT265 | Cassette | TTCGGACACGGGCATCTCAC | 38 |
| RT-PCR | | | |
| MTR001 | Actin | TCCAGGCCGTCCTCTCCC | 39 |
| MTR002 | Actin | GGCCAGCCATATCGAGTCGCA | 40 |
| MTR031 | DGA | AACGGAGGAGTGGTCAAGCGA | 41 |
| MTR032 | DGA | TTATGGGGAAGTAGCGGCCAA | 42 |
| MTR033 | D9 | GACCGACTCCAACAAGGACCCTT | 43 |
| MTR034 | D9 | GGGTTGGGCACAAGCAGCAT | 44 |
| MTR041 | ACC | GCTTCTCACGGAGGTCATACAGT | 45 |
| MTR042 | ACC | CTGCGGCAATACCGTTGTTAG | 46 |
| MTR068 | ACL1 | CCTCCTTGGTGAGGTTGGTGGT | 47 |
| MTR069 | ACL1 | GCGACGATGGGCTTCTTGATC | 48 |
| MTR070 | ACL2 | CCTTCAAGGGCATCATCCGG | 49 |
| MTR071 | ACL2 | CGCCTCGTCGCACGTAAATCT | 50 |

Example 3

Materials and Methods

Yeast Strains, Growth, and Culture Conditions

The ACC+DGA1 transformant strain of *Yarrowia lipolytica* (MTLY065), as discussed in Example 1, was employed in the experiments described in this section. YPD media was prepared as described in Example 1. The media constituents used in the bioreactor were yeast nitrogen base (without amino acids and ammonium sulfate) (Amresco), yeast extract (Difco), ammonium sulfate (Macron Chemicals), sodium acetate (Macron Chemicals) and acetic acid (Sigma Aldrich, St. Louis, Mo.). Bioreactor runs were carried out in 2 L baffled stirred tank reactors. The inoculum for the bioreactor was prepared as described in Example 1.

Bioreactor Operation: Acetate, Acetic Acid, and Ammonium Sulfate Feeding

The initial media composition in the reactor was: 30 g/L sodium acetate, 2.5 g/L yeast extract, 4.25 g/L yeast nitrogen base and 2.4 g/L ammonium sulfate. The yeast extract and yeast nitrogen base concentrations used in the experiments described in this section were higher as compared to those discussed in Example 1. A carbon to nitrogen ratio (C/N) of 20 was chosen to provide sufficient nitrogen for biomass production. A constant dissolved oxygen level of 20% was maintained at all times in the reactor using cascade control. A pH setpoint of 7.3 was used.

In order to generate high cell densities, which would then serve as the platform for lipid accumulation, a strategy was devised and implemented in which the carbon source of 30 g/L of sodium acetate was supplemented by feeding acetic acid. The use of acetic acid had several advantages, in that it served the dual purpose of providing a source of carbon to the growing and dividing cells and at the same time provided pH control. In order to maintain a low C/N ratio for the initial period of growth, a nitrogen source was fed concurrently with the acetic acid. The initial period of growth involved feeding 15 g/L ammonium sulfate per liter of 30% (vol/vol) acetic acid. The subsequent feed contained pure 100% acetic acid (and no ammonium sulfate), thus creating an increase in the C/N ratio as the nitrogen was consumed by the cells and depleted from the medium, resulting in improved lipid accumulation.

The working volume at the beginning of the run was 1.6 L. 1 L of the acid and ammonium sulfate solution was added over the first 60 h. Around 200 ml of pure acetic acid was added over the subsequent 40 h. Culture volume was not removed at any point other than the sampling done every 24 h for the purpose of measurements. To compensate for the additional volume entering the reactor, liquid was allowed to evaporate. The high aeration rate (2.5 vvm) led to sufficient evaporation, which helped in maintaining the volume of the reactor. Even with evaporation, the volume of the broth did go up slightly to around 1.8 L during the run.

Optical density (OD) of the culture broth was measured every 24 hours. Samples were stored at −20° C. for lipid analysis. HPLC analysis yielded acetate levels in the reactor. Ammonium was measured with an YSI 7100 ammonium electrode (YSI Life Sciences). Biomass was determined as discussed in Example 1.

Lipid Analysis

The lipid analysis involved a direct transesterification protocol, which was adapted from U.S. Pat. No. 7,932,077 and Griffiths et al. LIPIDS (2010) 45:1053-1060, the entire contents of each of which are incorporated herein by reference. The protocol employed 0.5 N sodium methoxide and 18 M sulfuric acid (Sigma Aldrich, St. Louis, Mo.). Sodium methoxide was generated in-house using sodium hydroxide (Macron Chemicals) and methanol (Sigma Aldrich, St. Louis, Mo.). 500 µl of the 0.5 N sodium methoxide was first added to 1 mg of the pelleted cell sample followed by vortexing for 1 hour. This was followed by addition of 40 µl sulfuric acid and 500 µl hexane followed by another vortex step for 30 min to dissolve the transesterified methyl esters into the hexane. The reaction mixture was centrifuged for 1 min at 8000 rpm, and 800 µl of the upper hexane phase were transferred into GC vials and analyzed in a GC-FID. The GC column, operating method, and final analysis followed the methods discussed in Example 1, except that glyceryl triheptadecanoate was used as the control instead of tridecanoic acid.

Results and Discussion

The results of the bioreactor run are summarized in Table 10.

TABLE 10

Results of the bioreactor run with acetate

| Lipid titer | 55 g/L |
|---|---|
| Lipid content | 67% |
| Overall lipid productivity | 0.56 g/L/h |
| Maximum lipid productivity | 1 g/L/h |
| Overall lipid yield (g lipid/g acetate) | 0.16 g/g |
| Maximum lipid yield | 0.24 g/g |

Figure 14:
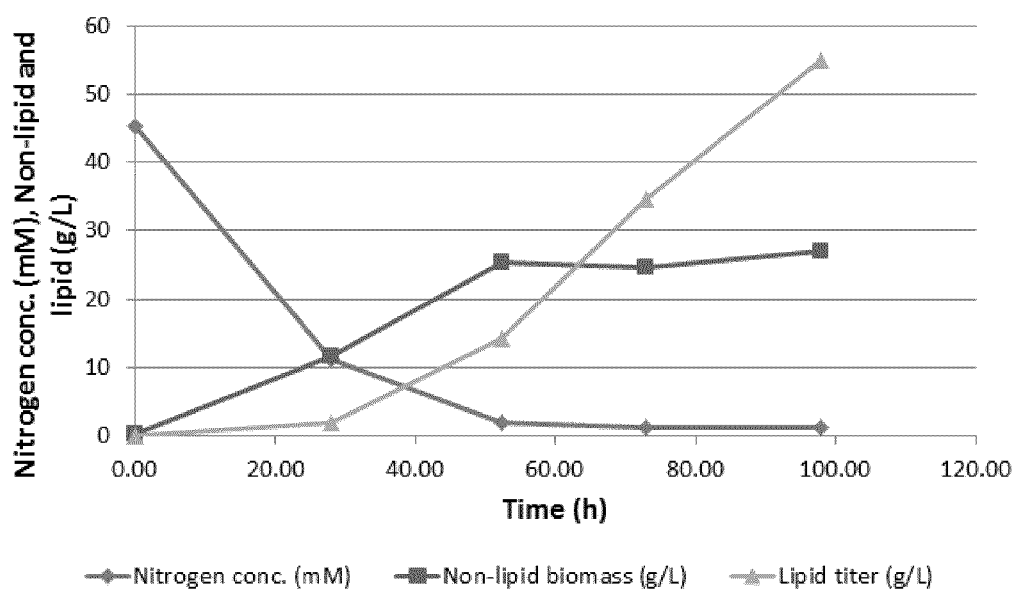
FIG. 14. Trends of nitrogen (mM), non-lipid and lipid titers (g/L).
Figure 15:
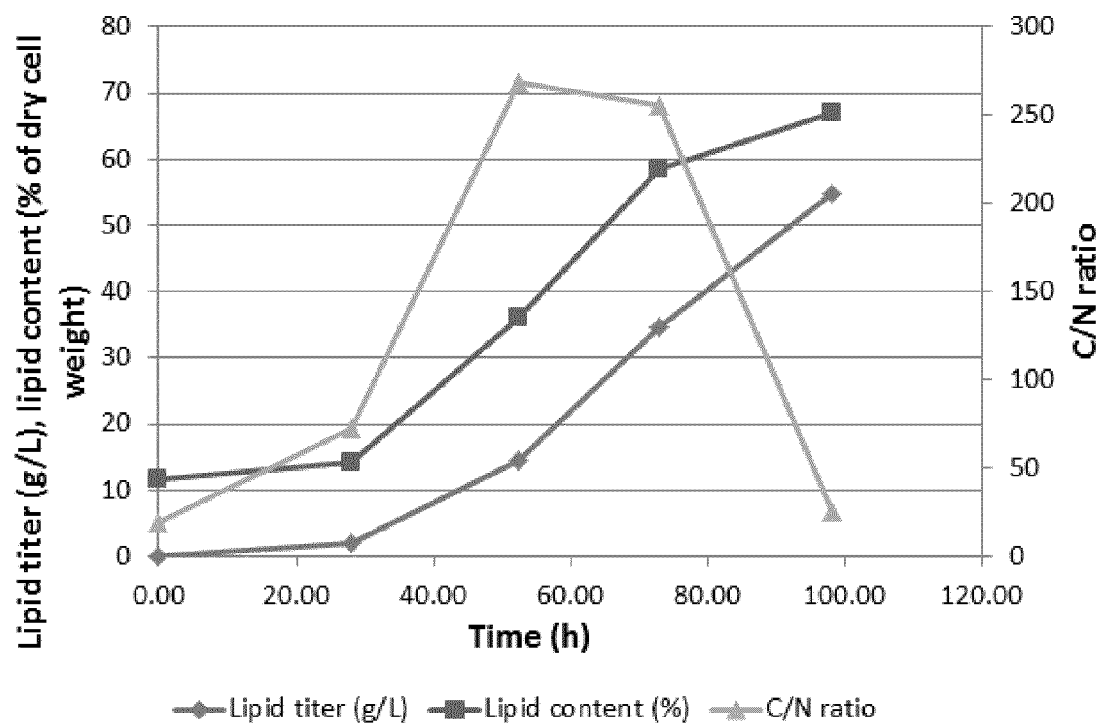
FIG. 15. Trends of lipid titer (g/L), lipid content (%) and C/N ratio. Primary axis shows lipid titer and lipid content as % of dry cell weight. Secondary axis shows C/N ratio. C/N ratio drops at the end due to the rapid consumption of acetate.

FIGS. 14 and 15 show trends of nitrogen, non-lipid and lipid titers, lipid content and C/N ratios during a representative acetate bioreactor run. The non-lipid biomass went up for the initial period of growth, when nitrogen was fed into the reactor. After 48 h, nearly all the biomass increase was due to lipid accumulation. In this period, the cells synthesized lipids at a yield of 0.24 g/g and at a rate of 1 g/L/h to produce a final lipid titer of 55 g/L, which is at least 10-fold higher than the titers achieved in the experiments described in Example 1. The final lipid content and overall lipid yield, though, were very similar to the lipid content and overall lipid yield in Example 1. These numbers depend mostly on the microbial strain employed. Almost 70% of the lipid was found to be oleate, which is consistent with the finding described in Example 1.

The run discussed here was aimed at maximizing lipid production using the ACC+DGA1 mutant through the adoption of above mentioned operating strategies and optimal process conditions. A comparison of the results of this run with those shown in Example 1 is been shown in table 11 below. A titer improvement of 10 fold and overall productivity improvement of 14 fold is seen between the acetate runs.

TABLE 11

Comparison of the run on acetate with the runs shown in example 1

|  | Glucose (example 1) | Acetate (example 1) | Acetate (this section) |
|---|---|---|---|
| Lipid titer | 17.6 g/L | 5.5 g/L | 55 g/L |
| Overall lipid productivity | 0.14 g/L/h | 0.04 g/L/h | 0.56 g/L/h |
| Max. lipid productivity | 0.26 g/L/h | 0.10 g/L/h | 1 g/L/h |
| Overall lipid yield | 0.19 g/g | 0.15 g/g | 0.16 g/g |
| Maximum lipid yield | 0.25 g/g | 0.27 g/g | 0.24 g/g |

Figure 16:
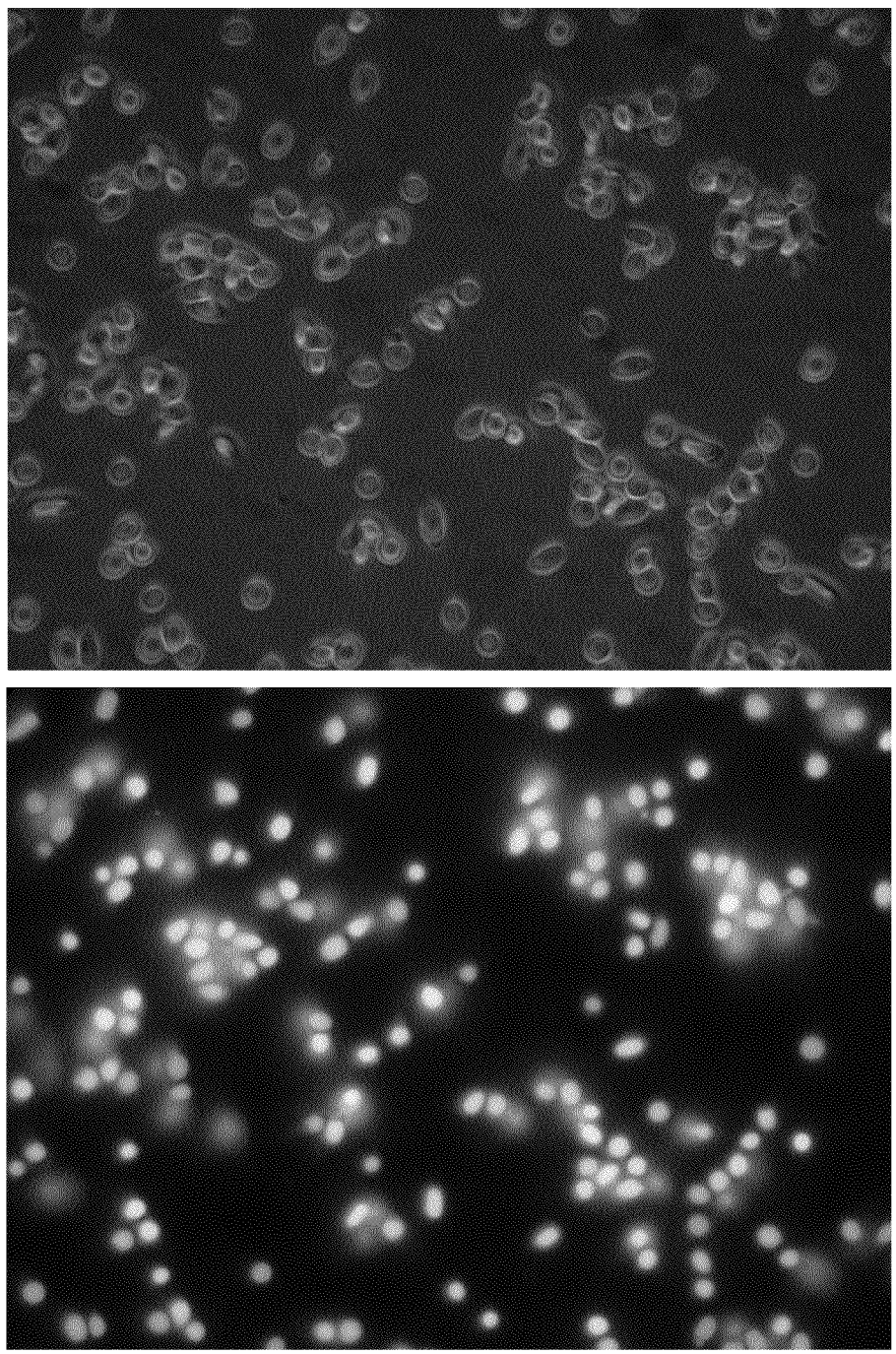
FIG. 16. Top—'Floating cells' seen under oil immersion microscope (100×) without fluorescence. Below—Same frame under fluorescence shows the bright red lipid body

Cells with high lipid content (greater than 80%) on centrifugation float at the top instead of settling down. These cells appear to be filled with oil under microscope. FIG. 16 shows such cells under an oil immersion microscope (100×) when stained with Nile Red. The bright spots are the lipid vacuoles.

All publications, patents and sequence database entries mentioned in the specification herein are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The invention claimed is:

1. An isolated oleaginous yeast cell, comprising a genetic modification that increases expression of a diacylglycerol acyltransferase (DGA1) gene product and an acetyl-CoA carboxylase (ACC1) gene product, wherein the genetic modification comprises
a first nucleic acid construct comprising an expression cassette comprising a coding nucleic acid encoding the DGA1 gene product; and
a second nucleic acid construct comprising an expression cassette comprising a coding nucleic acid encoding the ACC 1 gene product;
wherein the first nucleic acid construct and the second nucleic acid construct further comprises an intron-enhanced promoter that comprises a promoter sequence, a transcription start site, and an intronic sequence downstream of the transcription start site, and wherein the promoter is a translation elongation factor-1α (TEF) promoter.

2. The isolated oleaginous yeast cell of claim 1, further comprising a genetic modification that increases expression of a stearoyl-CoA-desaturase (SCD) gene product and/or of an ATP-citrate lyase (ACL) gene product, wherein the genetic modification comprises a nucleic acid construct comprising an expression cassette comprising a coding nucleic acid encoding the SCD and/or ACL gene product or an expression cassette comprising an intron-enhanced promoter that comprises a promoter sequence, a transcription start site, and an intronic sequence downstream of the transcription start site; and a coding nucleic acid encoding the SCD and/or ACL gene product.

3. The isolated oleaginous yeast cell of claim 1, wherein the first nucleic acid construct and/or the nucleic acid construct cassette comprises a suitable homologous or heterologous promoter.

4. The isolated oleaginous yeast cell of claim 1, wherein the increased expression of the gene product confers a beneficial phenotype for the conversion of a carbon source to a fatty acid, fatty acid derivative and/or triacylglycerol (TAG) to the cell, and wherein the beneficial phenotype comprises a modified fatty acid profile, a modified TAG profile, an increased fatty acid and/or triacylglycerol synthesis rate, an increase conversion yield, an increased triacylglycerol accumulation in the cell, and/or an increased triacylglycerol accumulation in a lipid body of the cell.

5. The isolated oleaginous yeast cell of claim 4, wherein the synthesis rate of a fatty acid or a TAG of the cell is at least 2-fold increased as compared to unmodified cells of the same cell type.

6. The isolated oleaginous yeast cell of claim 4, wherein the cell converts a carbon source to a fatty acid or a TAG at a conversion rate within the range of about 0.025 g/g to about 0.32 g/g (g TAG produced/g Glucose consumed), or at a conversion rate of at least 0.11 g/g.

7. A culture, comprising the oleaginous yeast cell of claim 1.

8. The culture of claim 7, further comprising a carbon source.

9. The culture of claim 8, wherein the carbon source comprises a fermentable sugar, an organic acid, and/or acetate.

10. The culture of claim 7, wherein the culture comprises glycerol.

11. The culture of claim 7, wherein the culture comprises ammonium sulfate.

12. A method, comprising
contacting a carbon source with the isolated oleaginous yeast cell of claim 1; and
incubating the carbon source contacted with the cell under conditions suitable for at least partial conversion of the carbon source into a fatty acid or a triacylglycerol by the cell.

13. The method of claim 12, wherein the oleaginous yeast cell further comprises a genetic modification that increases expression of an SCD gene product and/or an ACL gene product.

14. The isolated oleaginous yeast cell of claim 1, wherein the yeast is *Yarrowia lipolytica* or is derived from *Yarrowia lipolytica*.

15. The isolated oleaginous yeast cell of claim 1, wherein the coding nucleic acid encoding the DGA1 gene product comprises the nucleic acid sequence of SEQ ID NO: 1.

16. The isolated oleaginous yeast cell of claim 1, wherein the coding nucleic acid encoding the DGA1 gene product encodes for a protein comprising the amino acid sequence of SEQ ID NO: 2.

17. The isolated oleaginous yeast cell of claim 1, wherein the coding nucleic acid encoding the ACC1 gene product comprises the nucleic acid sequence of SEQ ID NO: 3.

18. The isolated oleaginous yeast cell of claim 1, wherein the coding nucleic acid encoding the ACC1 gene product encodes for a protein comprising the amino acid sequence of SEQ ID NO: 4.

* * * * *

SEQUENCE LISTING

```
<160> NUMBER OF SEQ ID NOS: 50

<210> SEQ ID NO 1
<211> LENGTH: 1545
<212> TYPE: DNA
<213> ORGANISM: Yarrowia lipolytica

<400> SEQUENCE: 1
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa tttcatgct atgctgcgca      180
attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg ccgctactt ccccataact ctgcacaaga cggtggatct ggagcccacg      360
cacacatact accctctgga cgtccaggag tatcacctga ttgctgagag atactggccg     420
cagaacaagt acctccgagc aatcatctcc accatcgagt actttctgcc cgccttcatg    480
aaacggtctc tttctatcaa cgagcaggag cagcctgccg agcgagatcc tctcctgtct    540
cccgtttctc ccagctctcc gggttctcaa cctgacaagt ggattaacca cgacagcaga    600
tatagccgtg gagaatcatc tggctccaac ggccacgcct cgggctccga acttaacggc    660
aacggcaaca atggcaccac taaccgacga ccttgtcgt ccgcctctgc tggctccact    720
gcatctgatt ccacgcttct taacgggtcc ctcaactcct acgccaacca gatcattggc    780
gaaaacgacc cacagctgtc gcccacaaaa ctcaagccca ctggcagaaa atacatcttc    840
ggctaccacc cccacggcat tatcggcatg ggagcctttg gtggaattgc caccgaggga    900
gctggatggt ccaagctctt tccgggcatc cctgtttctc ttatgactct caccaacaac    960
ttccgagtgc ctctctacag agagtacctc atgagtctgg gagtcgcttc tgtctccaag   1020
aagtcctgca aggccctcct caagcgaaac cagtctatct gcattgtcgt tggtggagca   1080
caggaaagtc ttctggccag acccggtgtc atggacctgg tgctactcaa gcgaagggt   1140
tttgttcgac ttggtatgga ggtcggaaat gtcgcccttg ttcccatcat ggcctttggt   1200
gagaacgacc tctatgacca ggttagcaac gacaagtcgt ccaagctgta ccgattccag   1260
cagtttgtca agaacttcct tggattcacc cttcctttga tgcatgcccg aggcgtcttc   1320
aactacgatg tcggtcttgt ccctacagg cgacccgtca acattgtggt tggttccccc   1380
attgacttgc cttatctccc acacccccacc gacgaagaag tgtccgaata ccacgaccga   1440
tacatcgccg agctgcagcg aatctacaac gagcacaagg atgaatattt catcgattgg   1500
accgaggagg gcaaaggagc cccagagttc cgaatgattg agtaa                   1545

<210> SEQ ID NO 2
<211> LENGTH: 514
<212> TYPE: PRT
<213> ORGANISM: Yarrowia lipolytica

<400> SEQUENCE: 2

Met Thr Ile Asp Ser Gln Tyr Tyr Lys Ser Arg Asp Lys Asn Asp Thr
1               5                   10                  15
```

```
Ala Pro Lys Ile Ala Gly Ile Arg Tyr Ala Pro Leu Ser Thr Pro Leu
             20                  25                  30

Leu Asn Arg Cys Glu Thr Phe Ser Leu Val Trp His Ile Phe Ser Ile
         35                  40                  45

Pro Thr Phe Leu Thr Ile Phe Met Leu Cys Cys Ala Ile Pro Leu Leu
     50                  55                  60

Trp Pro Phe Val Ile Ala Tyr Val Val Tyr Ala Val Lys Asp Asp Ser
 65                  70                  75                  80

Pro Ser Asn Gly Gly Val Val Lys Arg Tyr Ser Pro Ile Ser Arg Asn
                 85                  90                  95

Phe Phe Ile Trp Lys Leu Phe Gly Arg Tyr Phe Pro Ile Thr Leu His
                100                 105                 110

Lys Thr Val Asp Leu Glu Pro Thr His Thr Tyr Tyr Pro Leu Asp Val
            115                 120                 125

Gln Glu Tyr His Leu Ile Ala Glu Arg Tyr Trp Pro Gln Asn Lys Tyr
        130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
```

```
            435                 440                 445
Tyr Arg Arg Pro Val Asn Ile Val Val Gly Ser Pro Ile Asp Leu Pro
        450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu

<210> SEQ ID NO 3
<211> LENGTH: 7270
<212> TYPE: DNA
<213> ORGANISM: Yarrowia lipolytica

<400> SEQUENCE: 3
```

| | | | | | |
|---|---|---|---|---|---|
| atgcgactgc | aattgaggac | actaacacgt | cggtttttca | ggtgagtaaa | cgacggtggc | 60 |
| cgtggccacg | acagccgagg | cgtcacgatg | ggccagacga | gcacattctc | gccgccacaa | 120 |
| cctcgccagc | acaagaaact | aacccagtat | ggcttcagga | tcttcaacgc | agatgtggc | 180 |
| tcccttggtg | accccaaca | ttcacaaagg | tctcgcctct | catttctttg | gactcaattc | 240 |
| tgtccacaca | gccaagccct | caaaagtcaa | ggagtttgtg | gcttctcacg | gaggtcatac | 300 |
| agttatcaac | aaggtgagta | tttgacgttt | agactgtata | acaggcggcc | gcagtgcaac | 360 |
| aacgaccaaa | aagggtcgaa | aaggggtcga | aacggacac | aaaagctgga | aaacaagagt | 420 |
| gtaatacatt | cttacacgtc | caattgttag | acaaacacgg | ctgttcggtc | caaaaccac | 480 |
| cagtatcacc | tattttccac | ttgtgtctcg | gatctgatca | taatctgatc | tcaagatgaa | 540 |
| atttacgcca | ccgacatgat | attgtgattt | tcggattctc | cagaccgagc | agattccagc | 600 |
| aataccacca | cttgcccacc | ttcagcggcc | tctcggcgcg | attcgccact | tccccaacg | 660 |
| agtgttacta | acccaggtcc | tcatcgctaa | caacggtatt | gccgcagtaa | aggagatccg | 720 |
| ttcagtacga | aaatgggcct | acgagacctt | ggcgacgag | cgagcaatct | cgttcaccgt | 780 |
| catggccacc | cccgaagatc | tcgctgccaa | cgccgactac | attagaatgg | ccgatcagta | 840 |
| cgtcgaggtg | cccggaggaa | ccaacaacaa | caactacgcc | aacgtcgagc | tgattgtcga | 900 |
| cgtggctgag | cgattcggcg | tcgatgccgt | gtgggccgga | tggggccatg | ccagtgaaaa | 960 |
| tccccctgctc | cccgagtcgc | tagcggcctc | tccccgcaag | attgtcttca | tcggccctcc | 1020 |
| cggagctgcc | atgagatctc | tgggagacaa | aatttcttct | accattgtgg | cccagcacgc | 1080 |
| aaaggtcccg | tgtatcccgt | ggtctggaac | cggagtggac | gaggttgtgg | ttgacaagag | 1140 |
| caccaacctc | gtgtccgtgt | ccgaggaggt | gtacaccaag | ggctgcacca | ccggtcccaa | 1200 |
| gcagggtctg | gagaaggcta | agcagattgg | attccccgtg | atgatcaagg | cttccgaggg | 1260 |
| aggaggagga | aagggtattc | gaaaggttga | gcgagaggag | gacttcgagg | ctgcttacca | 1320 |
| ccaggtcgag | ggagagatcc | ccggctcgcc | catcttcatt | atgcagcttg | caggcaatgc | 1380 |
| ccggcatttg | gaggtgcagc | ttctggctga | tcagtacggc | aacaatattt | cactgtttgg | 1440 |
| tcgagattgt | tcggttcagc | gacggcatca | aaagattatt | gaggaggctc | ctgtgactgt | 1500 |
| ggctggccag | cagaccttca | ctgccatgga | gaaggctgcc | gtgcgactcg | gtaagcttgt | 1560 |
| cggatatgtc | tctgcaggta | ccgttgaata | tctgtattcc | catgaggacg | acaagttcta | 1620 |
| cttcttggag | ctgaatcctc | gtcttcaggt | cgaacatcct | accaccgaga | tggtcaccgg | 1680 |

```
tgtcaacctg cccgctgccc agcttcagat cgccatgggt atcccsctcg atcgaatcaa    1740
ggacattcgt ctcttttacg gtgttaaccc tcacaccacc actccaattg atttcgactt    1800
ctcgggcgag gatgctgata agacacagcg acgtcccgtc ccccgaggtc acaccactgc    1860
ttgccgaatc acatccgagg accctggaga gggtttcaag ccctccggag gtactatgca    1920
cgagctcaac ttccgatcct cgtccaacgt gtggggttac ttctccgttg gtaaccaggg    1980
aggtatccat tcgttctcgg attcgcagtt tggtcacatc ttcgccttcg gtgagaaccg    2040
aagtgcgtct cgaaagcaca tggttgttgc tttgaaggaa ctatctattc gaggtgactt    2100
ccgaaccacc gtcgagtacc tcatcaagct gctggagaca ccggacttcg aggacaacac    2160
catcaccacc ggctggctgg atgagcttat ctccaacaag ctgactgccg agcgacccga    2220
ctcgttcctc gctgttgttt gtggtgctgc taccaaggcc catcgagctt ccgaggactc    2280
tattgccacc tacatggctt cgctagagaa gggccaggtc cctgctcgag acattctcaa    2340 gaccctttc cccgttgact tcatctacga gggccagcgg tacaagttca ccgccacccg    2400
gtcgtctgag gactcttaca cgctgttcat caacggttct cgatgcgaca ttggagttag    2460
acctcttcct gacggtggta ttctgtgtct tgtaggtggg agatcccaca atgtctactg    2520
gaaggaggag gttggagcca cgcgactgtc tgttgactcc aagacctgcc ttctcgaggt    2580
ggagaacgac cccactcagc ttcgatctcc ctctcccggt aagctggtta agttcctggt    2640
cgagaacggc gaccacgtgc gagccaacca gccctatgcc gagattgagg tcatgaagat    2700
gtacatgact ctcactgctc aggaggacgg tattgtccag ctgatgaagc agcccggttc    2760
caccatcgag gctggcgaca tcctcggtat cttggcccctt gatgatcctt ccaaggtcaa    2820
gcatgccaag ccctttgagg ccagcttcc cgagcttgga cccccactc tcagcggtaa    2880 caagcctcat cagcgatacg agcactgcca gaacgtgctc cataacattc tgcttggttt    2940
cgataaccag gtggtgatga agtccactct tcaggagatg gttggtctgc tccgaaaccc    3000
tgagcttcct tatctccagt gggctcatca ggtgtcttct ctgcacaccc gaatgagcgc    3060
caagctggat gctactcttg ctggtctcat tgacaaggcc aagcagcgag gtggcgagtt    3120
tcctgccaag cagcttctgc gagcccttga gaaggaggcg agctctggcg aggtcgatgc    3180
gctcttccag caaactcttg ctcctctgtt tgaccttgct cgagagtacc aggacggtct    3240
tgctatccac gagcttcagg ttgctgcagg ccttctgcag gcctactacg actctgaggc    3300
ccggttctgc ggacccaacg tacgtgacga ggatgtcatt ctcaagcttc gagaggagaa    3360
ccgagattct cttcgaaagg ttgtgatggc ccagctgtct cattctcgag tcggagccaa    3420
gaacaacctt gtgctggccc ttctcgatga atacaaggtg gccgaccagg ctggcaccga    3480
ctctcctgcc tccaacgtgc acgttgcaaa gtacttgcga cctgtgctgc gaaagattgt    3540
ggagctggaa tctcgagctt ctgccaaggt atctctgaaa gcccgagaga ttctcatcca    3600
gtgcgctctg ccctctctaa aggagcgaac tgaccagctt gagcacattc tgcgatcttc    3660
tgtcgtcgag tctcgatacg gagaggttgg tctggagcac cgaactcccc gagccgatat    3720
tctcaaggag gttgtcgact ccaagtacat tgtctttgat gtgcttgccc agttcttttgc    3780 ccacgatgat ccctggatcg tccttgctgc cctggagctg tacatccgac gagcttgcaa    3840
ggcctactcc atcctggaca tcaactacca ccaggactcg gacctgcctc ccgtcatctc    3900
gtggcgattt agactgccta ccatgtcgtc tgctttgtac aactcagtag tgtcttctgg    3960 ctccaaaaacc cccacttccc cctcggtgtc tcgagctgat tccgtctccg actttttcgta    4020
```

```
caccgttgag cgagactctg ctcccgctcg aaccggagcg attgttgccg tgcctcatct    4080
ggatgatctg gaggatgctc tgactcgtgt tctggagaac ctgcccaaac ggggcgctgg    4140
tcttgccatc tctgttggtg ctagcaacaa gagtgccgct gcttctgctc gtgacgctgc    4200
tgctgctgcc gcttcatccg ttgacactgg cctgtccaac atttgcaacg ttatgattgg    4260
tcgggttgat gagtctgatg acgacgacac tctgattgcc cgaatctccc aggtcattga    4320
ggactttaag gaggactttg aggcctgttc tctgcgacga atcaccttct ccttcggcaa    4380
ctcccgaggt acttatccca agtatttcac gttccgaggc cccgcatacg aggaggaccc    4440
cactatccga cacattgagc ctgctctggc cttccagctg gagctcgccc gtctgtccaa    4500
cttcgacatc aagcctgtcc acaccgacaa ccgaaacatc cacgtgtacg aggctactgg    4560
caagaacgct gcttccgaca gcggttctt cacccgaggt atcgtacgac ctggtcgtct    4620
tcgagagaac atccccacct cggagtatct catttccgag gctgaccggc tcatgagcga    4680
tattttggac gctctagagg tgattggaac caccaactcg gatctcaacc acattttcat    4740
caacttctca gccgtctttg ctctgaagcc cgaggaggtt gaagctgcct ttggcggttt    4800
cctggagcga tttggccgac gtctgtggcg acttcgagtc accggtgccg agatccgaat    4860
gatggtatcc gaccccgaaa ctggctctgc tttccctctg cgagcaatga tcaacaacgt    4920
ctctggttac gttgtgcagt ctgagctgta cgctgaggcc aagaacgaca agggccagtg    4980
gattttcaag tctctgggca gcccggctc catgcacatg cggtctatca acactcccta    5040
ccccaccaag gagtggctgc agcccaagcg gtacaaggcc catctgatgg gtaccaccta    5100
ctgctatgac ttccccgagc tgttccgaca gtccattgag tcggactgga agaagtatga    5160
cggcaaggct cccgacgatc tcatgacttg caacgagctg attctcgatg aggactctgg    5220
cgagctgcag gaggtgaacc gagagcccgg cgccaacaac gtcggtatgg ttgcgtggaa    5280
gtttgaggcc aagaccccg agtaccctcg aggccgatct ttcatcgtgg tggccaacga    5340
tatcaccttc cagattggtt cgtttggccc tgctgaggac cagttcttct tcaaggtgac    5400
ggagctggct cgaaagctcg gtattcctcg aatctatctg tctgccaact ctggtgctcg    5460
aatcggcatt gctgacgagc tcgttggcaa gtacaaggtt gcgtggaacg acgagactga    5520 ccccctccaag ggcttcaagt accttttactt caccccctgag tctcttgcca ccctcaagcc    5580
cgacactgtt gtcaccactg agattgagga ggagggtccc aacggcgtgg agaagcgtca    5640
tgtgatcgac tacattgtcg gagagaagga cggtctcgga gtcgagtgtc tgcggggctc    5700
tggtctcatt gcaggcgcca cttctcgagc ctacaaggat atcttcactc tcactcttgt    5760
cacctgtcga tccgttggta tcggtgctta ccttgttcgt cttggtcaac gagccatcca    5820
gattgagggc cagcccatca ttctcactgg tgccccgcc atcaacaagc tgcttggtcg    5880
agaggtctac tcttccaact tgcagcttgg tggtactcag atcatgtaca caacggtgt    5940 gtctcatctg actgcccgag atgatctcaa cggtgtccac aagatcatgc agtggctgtc    6000
atacatccct gcttctcgag gtcttccagt gcctgttctc cctcacaaga ccgatgtgtg    6060
ggatcgagac gtgacgttcc agcctgtccg aggcgagcag tacgatgtta gatggcttat    6120
ttctggccga actctcgagg atggtgcttt cgagtctggt ctctttgaca aggactcttt    6180
ccaggagact ctgtctggct gggccaaggg tgttgttgtt ggtcgagctc gtcttggcgg    6240
cattcccttc ggtgtcattg gtgtcgagac tgcgaccgtc gacaatacta cccctgccga    6300 tccgccaac ccggactcta ttgagatgag cacctctgaa gccggccagg tttggtaccc    6360
caactcggcc ttcaagacct ctcaggccat caacgacttc aaccatggtg aggcgcttcc    6420
```

```
tctcatgatt cttgctaact ggcgaggctt ttctggtggt cagcgagaca tgtacaatga   6480
ggttctcaag tacggatctt tcattgttga tgctctggtt gactacaagc agcccatcat   6540
ggtgtacatc cctcccaccg gtgagctgcg aggtggttct tgggttgtgg ttgaccccac   6600
catcaactcg gacatgatgg agatgtacgc tgacgtcgag tctcgaggtg gtgtgctgga   6660
gcccgaggga atggtcggta tcaagtaccg acgagacaag ctactggaca ccatggctcg   6720
tctggatccc gagtactcct ctctcaagaa gcagcttgag gagtctcccg attctgagga   6780
gctcaaggtc aagctcagcg tgcgagagaa gtctctcatg cccatctacc agcagatctc   6840
cgtgcagttt gccgacttgc atgaccgagc tggccgaatg gaggccaagg tgtcattcg   6900 tgaggctctt gtgtggaagg atgctcgtcg attcttcttc tggcgaatcc gacgacgatt   6960
agtcgaggag tacctcatta ccaagatcaa tagcattctg ccctcttgca ctcggcttga   7020
gtgtctggct cgaatcaagt cgtggaagcc tgccactctt gatcagggct ctgaccgggg   7080
tgttgccgag tggtttgacg agaactctga tgccgtctct gctcgactca gcagctcaa   7140 gaaggacgct tctgcccagt cgtttgcttc tcaactgaga aaggaccgac agggtactct   7200
ccagggcatg aagcaggctc tcgcttctct ttctgaggct gagcgggctg agctgctcaa   7260
ggggttgtga                                                          7270

<210> SEQ ID NO 4
<211> LENGTH: 2266
<212> TYPE: PRT
<213> ORGANISM: Yarrowia lipolytica

<400> SEQUENCE: 4

Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Phe Gly Leu Asn Ser Val His Thr
        35                  40                  45

Ala Lys Pro Ser Lys Val Lys Glu Phe Val Ala Ser His Gly Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Asn Tyr Ala Asn Val Glu Leu Ile Val Asp
    130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175

Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Val Asp Lys Ser
```

-continued

```
            210                 215                 220
Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Lys Gly Ile Arg Lys
                260                 265                 270

Val Glu Arg Glu Glu Asp Phe Glu Ala Ala Tyr His Gln Val Glu Gly
            275                 280                 285

Glu Ile Pro Gly Ser Pro Ile Phe Ile Met Gln Leu Ala Gly Asn Ala
    290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg His Gln Lys Ile
                325                 330                 335

Ile Glu Glu Ala Pro Val Thr Val Ala Gly Gln Gln Thr Phe Thr Ala
                340                 345                 350

Met Glu Lys Ala Ala Val Arg Leu Gly Lys Leu Val Gly Tyr Val Ser
            355                 360                 365

Ala Gly Thr Val Glu Tyr Leu Tyr Ser His Glu Asp Asp Lys Phe Tyr
    370                 375                 380

Phe Leu Glu Leu Asn Pro Arg Leu Gln Val Glu His Pro Thr Thr Glu
385                 390                 395                 400

Met Val Thr Gly Val Asn Leu Pro Ala Ala Gln Leu Gln Ile Ala Met
                405                 410                 415

Gly Ile Pro Leu Asp Arg Ile Lys Asp Ile Arg Leu Phe Tyr Gly Val
                420                 425                 430

Asn Pro His Thr Thr Pro Ile Asp Phe Asp Phe Ser Gly Glu Asp
            435                 440                 445

Ala Asp Lys Thr Gln Arg Arg Pro Val Pro Arg Gly His Thr Thr Ala
    450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Asn Val Trp Gly
                485                 490                 495

Tyr Phe Ser Val Gly Asn Gln Gly Gly Ile His Ser Phe Ser Asp Ser
                500                 505                 510

Gln Phe Gly His Ile Phe Ala Phe Gly Glu Asn Arg Ser Ala Ser Arg
            515                 520                 525

Lys His Met Val Val Ala Leu Lys Glu Leu Ser Ile Arg Gly Asp Phe
    530                 535                 540

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
                580                 585                 590

Ala Ala Thr Lys Ala His Arg Ala Ser Glu Asp Ser Ile Ala Thr Tyr
            595                 600                 605

Met Ala Ser Leu Glu Lys Gly Gln Val Pro Ala Arg Asp Ile Leu Lys
    610                 615                 620

Thr Leu Phe Pro Val Asp Phe Ile Tyr Glu Gly Gln Arg Tyr Lys Phe
625                 630                 635                 640
```

-continued

```
Thr Ala Thr Arg Ser Ser Glu Asp Ser Tyr Thr Leu Phe Ile Asn Gly
            645                 650                 655
Ser Arg Cys Asp Ile Gly Val Arg Pro Leu Ser Asp Gly Gly Ile Leu
            660                 665                 670
Cys Leu Val Gly Gly Arg Ser His Asn Val Tyr Trp Lys Glu Glu Val
            675                 680                 685
Gly Ala Thr Arg Leu Ser Val Asp Ser Lys Thr Cys Leu Leu Glu Val
            690                 695                 700
Glu Asn Asp Pro Thr Gln Leu Arg Ser Pro Ser Pro Gly Lys Leu Val
705                 710                 715                 720
Lys Phe Leu Val Glu Asn Gly Asp His Val Arg Ala Asn Gln Pro Tyr
                725                 730                 735
Ala Glu Ile Glu Val Met Lys Met Tyr Met Thr Leu Thr Ala Gln Glu
                740                 745                 750
Asp Gly Ile Val Gln Leu Met Lys Gln Pro Gly Ser Thr Ile Glu Ala
                755                 760                 765
Gly Asp Ile Leu Gly Ile Leu Ala Leu Asp Asp Pro Ser Lys Val Lys
            770                 775                 780
His Ala Lys Pro Phe Glu Gly Gln Leu Pro Glu Leu Gly Pro Pro Thr
785                 790                 795                 800
Leu Ser Gly Asn Lys Pro His Gln Arg Tyr Glu His Cys Gln Asn Val
                805                 810                 815
Leu His Asn Ile Leu Leu Gly Phe Asp Asn Gln Val Val Met Lys Ser
                820                 825                 830
Thr Leu Gln Glu Met Val Gly Leu Leu Arg Asn Pro Glu Leu Pro Tyr
            835                 840                 845
Leu Gln Trp Ala His Gln Val Ser Ser Leu His Thr Arg Met Ser Ala
            850                 855                 860
Lys Leu Asp Ala Thr Leu Ala Gly Leu Ile Asp Lys Ala Lys Gln Arg
865                 870                 875                 880
Gly Gly Glu Phe Pro Ala Lys Gln Leu Leu Arg Ala Leu Glu Lys Glu
                885                 890                 895
Ala Ser Ser Gly Glu Val Asp Ala Leu Phe Gln Thr Leu Ala Pro
                900                 905                 910
Leu Phe Asp Leu Ala Arg Glu Tyr Gln Asp Gly Leu Ala Ile His Glu
            915                 920                 925
Leu Gln Val Ala Ala Gly Leu Leu Gln Ala Tyr Tyr Asp Ser Glu Ala
            930                 935                 940
Arg Phe Cys Gly Pro Asn Val Arg Asp Glu Asp Val Ile Leu Lys Leu
945                 950                 955                 960
Arg Glu Glu Asn Arg Asp Ser Leu Arg Lys Val Val Met Ala Gln Leu
                965                 970                 975
Ser His Ser Arg Val Gly Ala Lys Asn Asn Leu Val Leu Ala Leu Leu
            980                 985                 990
Asp Glu Tyr Lys Val Ala Asp Gln Ala Gly Thr Asp Ser Pro Ala Ser
            995                 1000                1005
Asn Val His Val Ala Lys Tyr Leu Arg Pro Val Leu Arg Lys Ile
        1010                1015                1020
Val Glu Leu Glu Ser Arg Ala Ser Ala Lys Val Ser Leu Lys Ala
        1025                1030                1035
Arg Glu Ile Leu Ile Gln Cys Ala Leu Pro Ser Leu Lys Glu Arg
        1040                1045                1050
```

```
Thr Asp Gln Leu Glu His Ile Leu Arg Ser Ser Val Val Glu Ser
1055                1060                1065

Arg Tyr Gly Glu Val Gly Leu Glu His Arg Thr Pro Arg Ala Asp
1070                1075                1080

Ile Leu Lys Glu Val Val Asp Ser Lys Tyr Ile Val Phe Asp Val
1085                1090                1095

Leu Ala Gln Phe Phe Ala His Asp Asp Pro Trp Ile Val Leu Ala
1100                1105                1110

Ala Leu Glu Leu Tyr Ile Arg Arg Ala Cys Lys Ala Tyr Ser Ile
1115                1120                1125

Leu Asp Ile Asn Tyr His Gln Asp Ser Asp Leu Pro Pro Val Ile
1130                1135                1140

Ser Trp Arg Phe Arg Leu Pro Thr Met Ser Ser Ala Leu Tyr Asn
1145                1150                1155

Ser Val Val Ser Ser Gly Ser Lys Thr Pro Thr Ser Pro Ser Val
1160                1165                1170

Ser Arg Ala Asp Ser Val Ser Asp Phe Ser Tyr Thr Val Glu Arg
1175                1180                1185

Asp Ser Ala Pro Ala Arg Thr Gly Ala Ile Val Ala Val Pro His
1190                1195                1200

Leu Asp Asp Leu Glu Asp Ala Leu Thr Arg Val Leu Glu Asn Leu
1205                1210                1215

Pro Lys Arg Gly Ala Gly Leu Ala Ile Ser Val Gly Ala Ser Asn
1220                1225                1230

Lys Ser Ala Ala Ala Ser Ala Arg Asp Ala Ala Ala Ala Ala Ala
1235                1240                1245

Ser Ser Val Asp Thr Gly Leu Ser Asn Ile Cys Asn Val Met Ile
1250                1255                1260

Gly Arg Val Asp Glu Ser Asp Asp Asp Thr Leu Ile Ala Arg
1265                1270                1275

Ile Ser Gln Val Ile Glu Asp Phe Lys Glu Asp Phe Glu Ala Cys
1280                1285                1290

Ser Leu Arg Arg Ile Thr Phe Ser Phe Gly Asn Ser Arg Gly Thr
1295                1300                1305

Tyr Pro Lys Tyr Phe Thr Phe Arg Gly Pro Ala Tyr Glu Glu Asp
1310                1315                1320

Pro Thr Ile Arg His Ile Glu Pro Ala Leu Ala Phe Gln Leu Glu
1325                1330                1335

Leu Ala Arg Leu Ser Asn Phe Asp Ile Lys Pro Val His Thr Asp
1340                1345                1350

Asn Arg Asn Ile His Val Tyr Glu Ala Thr Gly Lys Asn Ala Ala
1355                1360                1365

Ser Asp Lys Arg Phe Phe Thr Arg Gly Ile Val Arg Pro Gly Arg
1370                1375                1380

Leu Arg Glu Asn Ile Pro Thr Ser Glu Tyr Leu Ile Ser Glu Ala
1385                1390                1395

Asp Arg Leu Met Ser Asp Ile Leu Asp Ala Leu Glu Val Ile Gly
1400                1405                1410

Thr Thr Asn Ser Asp Leu Asn His Ile Phe Ile Asn Phe Ser Ala
1415                1420                1425

Val Phe Ala Leu Lys Pro Glu Glu Val Glu Ala Ala Phe Gly Gly
1430                1435                1440

Phe Leu Glu Arg Phe Gly Arg Arg Leu Trp Arg Leu Arg Val Thr
```

-continued

```
                1445                1450                1455
Gly Ala Glu Ile Arg Met Met Val Ser Asp Pro Glu Thr Gly Ser
        1460                1465                1470
Ala Phe Pro Leu Arg Ala Met Ile Asn Asn Val Ser Gly Tyr Val
        1475                1480                1485
Val Gln Ser Glu Leu Tyr Ala Glu Ala Lys Asn Asp Lys Gly Gln
        1490                1495                1500
Trp Ile Phe Lys Ser Leu Gly Lys Pro Gly Ser Met His Met Arg
        1505                1510                1515
Ser Ile Asn Thr Pro Tyr Pro Thr Lys Glu Trp Leu Gln Pro Lys
        1520                1525                1530
Arg Tyr Lys Ala His Leu Met Gly Thr Thr Tyr Cys Tyr Asp Phe
        1535                1540                1545
Pro Glu Leu Phe Arg Gln Ser Ile Glu Ser Asp Trp Lys Lys Tyr
        1550                1555                1560
Asp Gly Lys Ala Pro Asp Asp Leu Met Thr Cys Asn Glu Leu Ile
        1565                1570                1575
Leu Asp Glu Asp Ser Gly Glu Leu Gln Glu Val Asn Arg Glu Pro
        1580                1585                1590
Gly Ala Asn Asn Val Gly Met Val Ala Trp Lys Phe Glu Ala Lys
        1595                1600                1605
Thr Pro Glu Tyr Pro Arg Gly Arg Ser Phe Ile Val Val Ala Asn
        1610                1615                1620
Asp Ile Thr Phe Gln Ile Gly Ser Phe Gly Pro Ala Glu Asp Gln
        1625                1630                1635
Phe Phe Phe Lys Val Thr Glu Leu Ala Arg Lys Leu Gly Ile Pro
        1640                1645                1650
Arg Ile Tyr Leu Ser Ala Asn Ser Gly Ala Arg Ile Gly Ile Ala
        1655                1660                1665
Asp Glu Leu Val Gly Lys Tyr Lys Val Ala Trp Asn Asp Glu Thr
        1670                1675                1680
Asp Pro Ser Lys Gly Phe Lys Tyr Leu Tyr Phe Thr Pro Glu Ser
        1685                1690                1695
Leu Ala Thr Leu Lys Pro Asp Thr Val Val Thr Thr Glu Ile Glu
        1700                1705                1710
Glu Glu Gly Pro Asn Gly Val Glu Lys Arg His Val Ile Asp Tyr
        1715                1720                1725
Ile Val Gly Glu Lys Asp Gly Leu Gly Val Glu Cys Leu Arg Gly
        1730                1735                1740
Ser Gly Leu Ile Ala Gly Ala Thr Ser Arg Ala Tyr Lys Asp Ile
        1745                1750                1755
Phe Thr Leu Thr Leu Val Thr Cys Arg Ser Val Gly Ile Gly Ala
        1760                1765                1770
Tyr Leu Val Arg Leu Gly Gln Arg Ala Ile Gln Ile Glu Gly Gln
        1775                1780                1785
Pro Ile Ile Leu Thr Gly Ala Pro Ala Ile Asn Lys Leu Leu Gly
        1790                1795                1800
Arg Glu Val Tyr Ser Ser Asn Leu Gln Leu Gly Gly Thr Gln Ile
        1805                1810                1815
Met Tyr Asn Asn Gly Val Ser His Leu Thr Ala Arg Asp Asp Leu
        1820                1825                1830
Asn Gly Val His Lys Ile Met Gln Trp Leu Ser Tyr Ile Pro Ala
        1835                1840                1845
```

```
Ser Arg Gly Leu Pro Val Pro Val Leu Pro His Lys Thr Asp Val
1850                1855                1860

Trp Asp Arg Asp Val Thr Phe Gln Pro Val Arg Gly Glu Gln Tyr
1865                1870                1875

Asp Val Arg Trp Leu Ile Ser Gly Arg Thr Leu Glu Asp Gly Ala
1880                1885                1890

Phe Glu Ser Gly Leu Phe Asp Lys Asp Ser Phe Gln Glu Thr Leu
1895                1900                1905

Ser Gly Trp Ala Lys Gly Val Val Gly Arg Ala Arg Leu Gly
1910                1915                1920

Gly Ile Pro Phe Gly Val Ile Gly Val Glu Thr Ala Thr Val Asp
1925                1930                1935

Asn Thr Thr Pro Ala Asp Pro Ala Asn Pro Asp Ser Ile Glu Met
1940                1945                1950

Ser Thr Ser Glu Ala Gly Gln Val Trp Tyr Pro Asn Ser Ala Phe
1955                1960                1965

Lys Thr Ser Gln Ala Ile Asn Asp Phe Asn His Gly Glu Ala Leu
1970                1975                1980

Pro Leu Met Ile Leu Ala Asn Trp Arg Gly Phe Ser Gly Gly Gln
1985                1990                1995

Arg Asp Met Tyr Asn Glu Val Leu Lys Tyr Gly Ser Phe Ile Val
2000                2005                2010

Asp Ala Leu Val Asp Tyr Lys Gln Pro Ile Met Val Tyr Ile Pro
2015                2020                2025

Pro Thr Gly Glu Leu Arg Gly Gly Ser Trp Val Val Val Asp Pro
2030                2035                2040

Thr Ile Asn Ser Asp Met Met Glu Met Tyr Ala Asp Val Glu Ser
2045                2050                2055

Arg Gly Gly Val Leu Glu Pro Glu Gly Met Val Gly Ile Lys Tyr
2060                2065                2070

Arg Arg Asp Lys Leu Leu Asp Thr Met Ala Arg Leu Asp Pro Glu
2075                2080                2085

Tyr Ser Ser Leu Lys Lys Gln Leu Glu Glu Ser Pro Asp Ser Glu
2090                2095                2100

Glu Leu Lys Val Lys Leu Ser Val Arg Glu Lys Ser Leu Met Pro
2105                2110                2115

Ile Tyr Gln Gln Ile Ser Val Gln Phe Ala Asp Leu His Asp Arg
2120                2125                2130

Ala Gly Arg Met Glu Ala Lys Gly Val Ile Arg Glu Ala Leu Val
2135                2140                2145

Trp Lys Asp Ala Arg Arg Phe Phe Phe Trp Arg Ile Arg Arg Arg
2150                2155                2160

Leu Val Glu Glu Tyr Leu Ile Thr Lys Ile Asn Ser Ile Leu Pro
2165                2170                2175

Ser Cys Thr Arg Leu Glu Cys Leu Ala Arg Ile Lys Ser Trp Lys
2180                2185                2190

Pro Ala Thr Leu Asp Gln Gly Ser Asp Arg Gly Val Ala Glu Trp
2195                2200                2205

Phe Asp Glu Asn Ser Asp Ala Val Ser Ala Arg Leu Ser Glu Leu
2210                2215                2220

Lys Lys Asp Ala Ser Ala Gln Ser Phe Ala Ser Gln Leu Arg Lys
2225                2230                2235
```

```
Asp Arg Gln Gly Thr Leu Gln Gly Met Lys Gln Ala Leu Ala Ser
    2240                2245                2250

Leu Ser Glu Ala Glu Arg Ala Glu Leu Leu Lys Gly Leu
    2255                2260                2265
```

<210> SEQ ID NO 5
<211> LENGTH: 1449
<212> TYPE: DNA
<213> ORGANISM: Yarrowia lipolytica

<400> SEQUENCE: 5

```
atggtgaaaa acgtggacca agtggatctc tcgcaggtcg acaccattgc ctccggccga      60
gatgtcaact acaaggtcaa gtacacctcc ggcgttaaga tgagccaggg cgcctacgac     120
gacaagggcc gccacatttc cgagcagccc ttcacctggg ccaactggca ccagcacatc     180
aactggctca acttcattct ggtgattgcg ctgcctctgt cgtcctttgc tgccgctccc     240
ttcgtctcct tcaactggaa gaccgccgcg tttgctgtcg gctattacat gtgcaccggt     300
ctcggtatca ccgccggcta ccaccgaatg tgggcccatc gagcctacaa ggccgctctg     360
cccgttcgaa tcatccttgc tctgtttgga ggaggagctg tcgagggctc catccgatgg     420
tgggcctcgt ctcaccgagt ccaccaccga tggaccgact ccaacaagga cccttacgac     480
gcccgaaagg gattctggtt ctcccacttt ggctggatgc tgcttgtgcc caaccccaag     540
aacaagggcc gaactgacat ttctgacctc aacaacgact gggttgtccg actccagcac     600
aagtactacg tttacgttct cgtcttcatg gccattgttc tgcccaccct cgtctgtggc     660
tttggctggg gcgactggaa gggaggtctt gtctacgccg gtatcatgcg atacaccttt     720
gtgcagcagg tgactttctg tgtcaactcc cttgcccact ggattggaga gcagccttc     780
gacgaccgac gaactccccg agaccacgct cttaccgccc tggtcacctt ggagagggc     840
taccacaact ccaccacga gttccctcg gactaccgaa acgccctcat ctggtaccag     900
tacgaccca ccaagtggct catctggacc ctcaagcagg ttggtctcgc ctgggaccct     960
cagaccttct cccagaacgc catcgagcag ggtctcgtgc agcagcgaca agaagctg    1020
gacaagtggc gaaacaacct caactggggt atccccattg agcagctgcc tgtcattgag    1080
tttgaggagt tccaagagca ggccaagacc cgagatctgg ttctcatttc tggcattgtc    1140
cacgacgtgt ctgcctttgt cgagcaccac cctggtggaa aggccctcat tatgagcgcc    1200
gtcggcaagg acggtaccgc tgtcttcaac ggaggtgtct accgacactc caacgctggc    1260
cacaacctgc ttgccaccat gcagtttccg gtcattcgag gcggcatgga ggttgaggtg    1320
tggaagactg cccagaacga aaagaaggac cagaacattg tctccgatga gagtggaaac    1380
cgaatccacc gagctggtct ccaggccacc cgggtcgaga ccccggtat gtctggcatg    1440
gctgcttag                                                            1449
```

<210> SEQ ID NO 6
<211> LENGTH: 482
<212> TYPE: PRT
<213> ORGANISM: Yarrowia lipolytica

<400> SEQUENCE: 6

```
Met Val Lys Asn Val Asp Gln Val Asp Leu Ser Gln Val Asp Thr Ile
1               5                  10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
```

```
                35                  40                  45
Gln Pro Phe Thr Trp Ala Asn Trp His Gln His Ile Asn Trp Leu Asn
 50                  55                  60

Phe Ile Leu Val Ile Ala Leu Pro Leu Ser Ser Phe Ala Ala Pro
65                  70                  75                  80

Phe Val Ser Phe Asn Trp Lys Thr Ala Ala Phe Ala Val Gly Tyr Tyr
                 85                  90                  95

Met Cys Thr Gly Leu Gly Ile Thr Ala Gly Tyr His Arg Met Trp Ala
                100                 105                 110

His Arg Ala Tyr Lys Ala Ala Leu Pro Val Arg Ile Ile Leu Ala Leu
                115                 120                 125

Phe Gly Gly Gly Ala Val Glu Gly Ser Ile Arg Trp Trp Ala Ser Ser
                130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
                180                 185                 190

Asp Trp Val Val Arg Leu Gln His Lys Tyr Tyr Val Tyr Val Leu Val
                195                 200                 205

Phe Met Ala Ile Val Leu Pro Thr Leu Val Cys Gly Phe Gly Trp Gly
                210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
                260                 265                 270

Ala Leu Val Thr Phe Gly Glu Gly Tyr His Asn Phe His His Glu Phe
                275                 280                 285

Pro Ser Asp Tyr Arg Asn Ala Leu Ile Trp Tyr Gln Tyr Asp Pro Thr
                290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Gln Arg
                325                 330                 335

Gln Lys Lys Leu Asp Lys Trp Arg Asn Asn Leu Asn Trp Gly Ile Pro
                340                 345                 350

Ile Glu Gln Leu Pro Val Ile Glu Phe Glu Glu Phe Gln Glu Gln Ala
                355                 360                 365

Lys Thr Arg Asp Leu Val Leu Ile Ser Gly Ile Val His Asp Val Ser
                370                 375                 380

Ala Phe Val Glu His His Pro Gly Gly Lys Ala Leu Ile Met Ser Ala
385                 390                 395                 400

Val Gly Lys Asp Gly Thr Ala Val Phe Asn Gly Val Tyr Arg His
                405                 410                 415

Ser Asn Ala Gly His Asn Leu Leu Ala Thr Met Arg Val Ser Val Ile
                420                 425                 430

Arg Gly Gly Met Glu Val Glu Val Trp Lys Thr Ala Gln Asn Glu Lys
                435                 440                 445

Lys Asp Gln Asn Ile Val Ser Asp Glu Ser Gly Asn Arg Ile His Arg
                450                 455                 460
```

Ala Gly Leu Gln Ala Thr Arg Val Glu Asn Pro Gly Met Ser Gly Met
465                 470                 475                 480

Ala Ala

<210> SEQ ID NO 7
<211> LENGTH: 1953
<212> TYPE: DNA
<213> ORGANISM: Yarrowia lipolytica

<400> SEQUENCE: 7

| | | | | | |
|---|---|---|---|---|---|
| atgtctgcca | acgagaacat | ctcccgattc | gacgcccctg | tgggcaagga | gcacccgcc | 60 |
| tacgagctct | tccataacca | cacacgatct | ttcgtctatg | gtctccagcc | tcgagcctgc | 120 |
| cagggtatgc | tggacttcga | cttcatctgt | aagcgagaga | cccctccgt | ggccggtgtc | 180 |
| atctatccct | tcggcggcca | gttcgtcacc | aagatgtact | ggggcaccaa | ggagactctt | 240 |
| ctccctgtct | accagcaggt | cgagaaggcc | gctgccaagc | accccgaggt | cgatgtcgtg | 300 |
| gtcaactttg | cctcctctcg | atccgtctac | tcctctacca | tggagctgct | cgagtacccc | 360 |
| cagttccgaa | ccatcgccat | tattgccgag | ggtgtccccg | agcgacgagc | ccgagagatc | 420 |
| ctccacaagg | cccagaagaa | gggtgtgacc | atcattggtc | ccgctaccgt | cggaggtatc | 480 |
| aagcccggtt | gcttcaaggt | tggaaacacc | ggaggtatga | tggacaacat | tgtcgcctcc | 540 |
| aagctctacc | gacccggctc | cgttgcctac | gtctccaagt | ccgaggaat | gtccaacgag | 600 |
| ctgaacaaca | ttatctctca | caccaccgac | ggtgtctacg | agggtattgc | tattggtggt | 660 |
| gaccgatacc | ctggtactac | cttcattgac | catatcctgc | gatacgaggc | cgaccccaag | 720 |
| tgtaagatca | tcgtcctcct | tggtgaggtt | ggtggtgttg | aggagtaccg | agtcatcgag | 780 |
| gctgttaaga | acgccagat | caagaagccc | atcgtcgctt | gggccattgg | tacttgtgcc | 840 |
| tccatgttca | agactgaggt | tcagttcggc | cacgccggct | ccatggccaa | ctccgacctg | 900 |
| gagactgcca | aggctaagaa | cgccgccatg | aagtctgctg | gcttctacgt | ccccgatacc | 960 |
| ttcgaggaca | tgcccgaggt | ccttgccgag | ctctacgaga | gatggtcgc | caagggcgag | 1020 |
| ctgtctcgaa | tctctgagcc | tgaggtcccc | aagatcccca | ttgactactc | ttgggcccag | 1080 |
| gagcttggtc | ttatccgaaa | gcccgctgct | ttcatctcca | ctatttccga | tgaccgaggc | 1140 |
| caggagcttc | tgtacgctgg | catgcccatt | tccgaggttt | tcaaggagga | cattggtatc | 1200 |
| ggcggtgtca | tgtctctgct | gtggttccga | cgacgactcc | ccgactacgc | ctccaagttt | 1260 |
| cttgagatgg | ttctcatgct | tactgctgac | acggtcccg | ccgtatccgg | tgccatgaac | 1320 |
| accattatca | ccacccgagc | tggtaaggat | ctcatttctt | ccctggttgc | tggtctcctg | 1380 |
| accattggta | cccgattcgg | aggtgctctt | gacggtgctg | ccaccgagtt | caccactgcc | 1440 |
| tacgacaagg | gtctgtcccc | ccgacagttc | gttgatacca | tgcgaaagca | gaacaagctg | 1500 |
| attcctggta | ttggccatcg | agtcaagtct | cgaaacaacc | ccgatttccg | agtcgagctt | 1560 |
| gtcaaggact | tgttaagaa | gaacttcccc | tccacccagc | tgctcgacta | cgccttgct | 1620 |
| gtcgaggagg | tcaccaccctc | caagaaggac | aacctgattc | tgaacgttga | cggtgctatt | 1680 |
| gctgtttctt | ttgtcgatct | catgcgatct | tgcggtgcct | ttactgtgga | ggagactgag | 1740 |
| gactacctca | agaacggtgt | tctcaacggt | ctgttcgttc | tcggtcgatc | cattggtctc | 1800 |
| attgcccacc | atctcgatca | gaagcgactc | aagaccggtc | tgtaccgaca | tccttgggac | 1860 |
| gatatcacct | acctggttgg | ccaggaggct | atccagaaga | agcgagtcga | gatcagcgcc | 1920 |
| ggcgacgttt | ccaaggccaa | gactcgatca | tag | | | 1953 |

```
<210> SEQ ID NO 8
<211> LENGTH: 650
<212> TYPE: PRT
<213> ORGANISM: Yarrowia lipolytica

<400> SEQUENCE: 8
```

| | | | | | | | | | | | | | | | |
|---|---|---|---|---|---|---|---|---|---|---|---|---|---|---|---|
| Met | Ser | Ala | Asn | Glu | Asn | Ile | Ser | Arg | Phe | Asp | Ala | Pro | Val | Gly | Lys |
| 1 | | | | 5 | | | | | 10 | | | | | 15 | |
| Glu | His | Pro | Ala | Tyr | Glu | Leu | Phe | His | Asn | His | Thr | Arg | Ser | Phe | Val |
| | | | 20 | | | | | 25 | | | | | 30 | | |
| Tyr | Gly | Leu | Gln | Pro | Arg | Ala | Cys | Gln | Gly | Met | Leu | Asp | Phe | Asp | Phe |
| | | 35 | | | | | 40 | | | | | 45 | | | |
| Ile | Cys | Lys | Arg | Glu | Asn | Pro | Ser | Val | Ala | Gly | Val | Ile | Tyr | Pro | Phe |
| 50 | | | | | 55 | | | | | 60 | | | | | |
| Gly | Gly | Gln | Phe | Val | Thr | Lys | Met | Tyr | Trp | Gly | Thr | Lys | Glu | Thr | Leu |
| 65 | | | | 70 | | | | | 75 | | | | | 80 | |
| Leu | Pro | Val | Tyr | Gln | Gln | Val | Glu | Lys | Ala | Ala | Ala | Lys | His | Pro | Glu |
| | | | | 85 | | | | | 90 | | | | | 95 | |
| Val | Asp | Val | Val | Asn | Phe | Ala | Ser | Ser | Arg | Ser | Val | Tyr | Ser | Ser |
| | | | 100 | | | | | 105 | | | | | 110 | | |
| Thr | Met | Glu | Leu | Leu | Glu | Tyr | Pro | Gln | Phe | Arg | Thr | Ile | Ala | Ile | Ile |
| | | | 115 | | | | | 120 | | | | | 125 | | |
| Ala | Glu | Gly | Val | Pro | Glu | Arg | Arg | Ala | Arg | Glu | Ile | Leu | His | Lys | Ala |
| | 130 | | | | | 135 | | | | | 140 | | | | |
| Gln | Lys | Lys | Gly | Val | Thr | Ile | Ile | Gly | Pro | Ala | Thr | Val | Gly | Gly | Ile |
| 145 | | | | | 150 | | | | | 155 | | | | | 160 |
| Lys | Pro | Gly | Cys | Phe | Lys | Val | Gly | Asn | Thr | Gly | Gly | Met | Met | Asp | Asn |
| | | | | 165 | | | | | 170 | | | | | 175 | |
| Ile | Val | Ala | Ser | Lys | Leu | Tyr | Arg | Pro | Gly | Ser | Val | Ala | Tyr | Val | Ser |
| | | | 180 | | | | | 185 | | | | | 190 | | |
| Lys | Ser | Gly | Gly | Met | Ser | Asn | Glu | Leu | Asn | Asn | Ile | Ile | Ser | His | Thr |
| | | 195 | | | | | 200 | | | | | 205 | | | |
| Thr | Asp | Gly | Val | Tyr | Glu | Gly | Ile | Ala | Ile | Gly | Gly | Asp | Arg | Tyr | Pro |
| | 210 | | | | | 215 | | | | | 220 | | | | |
| Gly | Thr | Thr | Phe | Ile | Asp | His | Ile | Leu | Arg | Tyr | Glu | Ala | Asp | Pro | Lys |
| 225 | | | | | 230 | | | | | 235 | | | | | 240 |
| Cys | Lys | Ile | Ile | Val | Leu | Leu | Gly | Glu | Val | Gly | Gly | Val | Glu | Glu | Tyr |
| | | | | 245 | | | | | 250 | | | | | 255 | |
| Arg | Val | Ile | Glu | Ala | Val | Lys | Asn | Gly | Gln | Ile | Lys | Lys | Pro | Ile | Val |
| | | | 260 | | | | | 265 | | | | | 270 | | |
| Ala | Trp | Ala | Ile | Gly | Thr | Cys | Ala | Ser | Met | Phe | Lys | Thr | Glu | Val | Gln |
| | | | | 275 | | | | | 280 | | | | | 285 | |
| Phe | Gly | His | Ala | Gly | Ser | Met | Ala | Asn | Ser | Asp | Leu | Glu | Thr | Ala | Lys |
| | | 290 | | | | | 295 | | | | | 300 | | | |
| Ala | Lys | Asn | Ala | Ala | Met | Lys | Ser | Ala | Gly | Phe | Tyr | Val | Pro | Asp | Thr |
| 305 | | | | | 310 | | | | | 315 | | | | | 320 |
| Phe | Glu | Asp | Met | Pro | Glu | Val | Leu | Ala | Glu | Leu | Tyr | Glu | Lys | Met | Val |
| | | | | 325 | | | | | 330 | | | | | 335 | |
| Ala | Lys | Gly | Glu | Leu | Ser | Arg | Ile | Ser | Glu | Pro | Glu | Val | Pro | Lys | Ile |
| | | | 340 | | | | | 345 | | | | | 350 | | |
| Pro | Ile | Asp | Tyr | Ser | Trp | Ala | Gln | Glu | Leu | Gly | Leu | Ile | Arg | Lys | Pro |
| | | | | 355 | | | | | 360 | | | | | 365 | |
| Ala | Ala | Phe | Ile | Ser | Thr | Ile | Ser | Asp | Asp | Arg | Gly | Gln | Glu | Leu | Leu |

```
                370             375             380
Tyr Ala Gly Met Pro Ile Ser Glu Val Phe Lys Glu Asp Ile Gly Ile
385                 390                 395                 400

Gly Gly Val Met Ser Leu Leu Trp Phe Arg Arg Leu Pro Asp Tyr
            405                 410                 415

Ala Ser Lys Phe Leu Glu Met Val Leu Met Leu Thr Ala Asp His Gly
            420                 425                 430

Pro Ala Val Ser Gly Ala Met Asn Thr Ile Ile Thr Thr Arg Ala Gly
            435                 440                 445

Lys Asp Leu Ile Ser Ser Leu Val Ala Gly Leu Leu Thr Ile Gly Thr
450                 455                 460

Arg Phe Gly Gly Ala Leu Asp Gly Ala Ala Thr Glu Phe Thr Thr Ala
465                 470                 475                 480

Tyr Asp Lys Gly Leu Ser Pro Arg Gln Phe Val Asp Thr Met Arg Lys
                485                 490                 495

Gln Asn Lys Leu Ile Pro Gly Ile Gly His Arg Val Lys Ser Arg Asn
            500                 505                 510

Asn Pro Asp Phe Arg Val Glu Leu Val Lys Asp Phe Val Lys Lys Asn
            515                 520                 525

Phe Pro Ser Thr Gln Leu Leu Asp Tyr Ala Leu Ala Val Glu Glu Val
530                 535                 540

Thr Thr Ser Lys Lys Asp Asn Leu Ile Leu Asn Val Asp Gly Ala Ile
545                 550                 555                 560

Ala Val Ser Phe Val Asp Leu Met Arg Ser Cys Gly Ala Phe Thr Val
            565                 570                 575

Glu Glu Thr Glu Asp Tyr Leu Lys Asn Gly Val Leu Asn Gly Leu Phe
            580                 585                 590

Val Leu Gly Arg Ser Ile Gly Leu Ile Ala His His Leu Asp Gln Lys
            595                 600                 605

Arg Leu Lys Thr Gly Leu Tyr Arg His Pro Trp Asp Asp Ile Thr Tyr
            610                 615                 620

Leu Val Gly Gln Glu Ala Ile Gln Lys Lys Arg Val Glu Ile Ser Ala
625                 630                 635                 640

Gly Asp Val Ser Lys Ala Lys Thr Arg Ser
                645                 650

<210> SEQ ID NO 9
<211> LENGTH: 1494
<212> TYPE: DNA
<213> ORGANISM: Yarrowia lipolytica

<400> SEQUENCE: 9
atgtcagcga aatccattca cgaggccgac ggcaaggccc tgctcgcaca ctttctgtcc      60
aaggcgcccg tgtgggccga gcagcagccc atcaacacgt tgaaatggg cacacccaag     120 ctggcgtctc tgacgttcga ggacggcgtg gcccccgagc agatcttcgc cgccgctgaa    180
aagacctacc cctggctgct ggagtccggc gccaagtttg tggccaagcc cgaccagctc    240
atcaagcgac gaggcaaggc cggcctgctg gtactcaaca gtcgtgggga ggagtgcaag    300
ccctggatcg ccgagcgggc cgccaagccc atcaacgtgg agggcattga cggagtgctg    360
cgaacgttcc tggtcgagcc ctttgtgccc cacgaccaga agcacgagta ctacatcaac    420
atccactccg tgcgagaggg cgactggatc ctcttctacc acgagggagg agtcgacgtc    480
ggcgacgtgg acgccaaggc cgccaagatc ctcatccccg ttgacattga gaacgagtac    540
```

-continued

```
ccctccaacg ccacgctcac caaggagctg ctggcacacg tgcccgagga ccagcaccag    600
accctgctcg acttcatcaa ccggctctac gccgtctacg tcgatctgca gtttacgtat    660
ctggagatca accccctggt cgtgatcccc accgcccagg gcgtcgaggt ccactacctg    720
gatcttgccg gcaagctcga ccagaccgca gagtttgagt gcggcccccaa gtgggctgct    780
gcgcggtccc cgccgctct gggccaggtc gtcaccattg acgccggctc caccaaggtg    840
tccatcgacg ccggccccgc catggtcttc cccgctcctt cggtcgaga gctgtccaag    900
gaggaggcgt acattgcgga gctcgattcc aagaccggag cttctctgaa gctgactgtt    960
ctcaatgcca agggccgaat ctggaccctt gtggctggtg gaggagcctc cgtcgtctac   1020
gccgacgcca ttgcgtctgc cggctttgct gacgagctcg ccaactacgg cgagtactct   1080
ggcgctccca acgagaccca gacctacgag tacgccaaaa ccgtactgga tctcatgacc   1140
cggggcgacg ctcaccccga gggcaaggta ctgttcattg gcggaggaat cgccaacttc   1200
acccaggttg gatccacctt caagggcatc atccgggcct ccgggactg ccagtcttct   1260
ctgcacaacc acaaggtgaa gatttacgtg cgacgaggcg gtcccaactg gcaggagggt   1320
ctgcggttga tcaagtcggc tggcgacgag ctgaatctgc ccatggagat ttacggcccc   1380
gacatgcacg tgtcgggtat tgttcctttg gctctgcttg gaaagcggcc aagaatgtc    1440
aagcctttg gcaccggacc ttctactgag gcttccactc ctctcggagt ttaa          1494
```

<210> SEQ ID NO 10
<211> LENGTH: 497
<212> TYPE: PRT
<213> ORGANISM: Yarrowia lipolytica

<400> SEQUENCE: 10

```
Met Ser Ala Lys Ser Ile His Glu Ala Asp Gly Lys Ala Leu Leu Ala
1               5                  10                  15

His Phe Leu Ser Lys Ala Pro Val Trp Ala Glu Gln Gln Pro Ile Asn
            20                  25                  30

Thr Phe Glu Met Gly Thr Pro Lys Leu Ala Ser Leu Thr Phe Glu Asp
        35                  40                  45

Gly Val Ala Pro Glu Gln Ile Phe Ala Ala Glu Lys Thr Tyr Pro
    50                  55                  60

Trp Leu Leu Glu Ser Gly Ala Lys Phe Val Ala Lys Pro Asp Gln Leu
65                  70                  75                  80

Ile Lys Arg Arg Gly Lys Ala Gly Leu Leu Val Leu Asn Lys Ser Trp
                85                  90                  95

Glu Glu Cys Lys Pro Trp Ile Ala Glu Arg Ala Ala Lys Pro Ile Asn
            100                 105                 110

Val Glu Gly Ile Asp Gly Val Leu Arg Thr Phe Leu Val Glu Pro Phe
        115                 120                 125

Val Pro His Asp Gln Lys His Glu Tyr Tyr Ile Asn Ile His Ser Val
    130                 135                 140

Arg Glu Gly Asp Trp Ile Leu Phe Tyr His Glu Gly Gly Val Asp Val
145                 150                 155                 160

Gly Asp Val Asp Ala Lys Ala Ala Lys Ile Leu Ile Pro Val Asp Ile
                165                 170                 175

Glu Asn Glu Tyr Pro Ser Asn Ala Thr Leu Thr Lys Glu Leu Leu Ala
            180                 185                 190

His Val Pro Glu Asp Gln His Gln Thr Leu Leu Asp Phe Ile Asn Arg
        195                 200                 205
```

Leu Tyr Ala Val Tyr Val Asp Leu Gln Phe Thr Tyr Leu Glu Ile Asn
                210                 215                 220

Pro Leu Val Val Ile Pro Thr Ala Gln Gly Val Glu Val His Tyr Leu
225                 230                 235                 240

Asp Leu Ala Gly Lys Leu Asp Gln Thr Ala Glu Phe Glu Cys Gly Pro
                245                 250                 255

Lys Trp Ala Ala Ala Arg Ser Pro Ala Ala Leu Gly Gln Val Val Thr
                260                 265                 270

Ile Asp Ala Gly Ser Thr Lys Val Ser Ile Asp Ala Gly Pro Ala Met
                275                 280                 285

Val Phe Pro Ala Pro Phe Gly Arg Glu Leu Ser Lys Glu Glu Ala Tyr
290                 295                 300

Ile Ala Glu Leu Asp Ser Lys Thr Gly Ala Ser Leu Lys Leu Thr Val
305                 310                 315                 320

Leu Asn Ala Lys Gly Arg Ile Trp Thr Leu Val Ala Gly Gly Gly Ala
                325                 330                 335

Ser Val Val Tyr Ala Asp Ala Ile Ala Ser Ala Gly Phe Ala Asp Glu
                340                 345                 350

Leu Ala Asn Tyr Gly Glu Tyr Ser Gly Ala Pro Asn Glu Thr Gln Thr
                355                 360                 365

Tyr Glu Tyr Ala Lys Thr Val Leu Asp Leu Met Thr Arg Gly Asp Ala
                370                 375                 380

His Pro Glu Gly Lys Val Leu Phe Ile Gly Gly Ile Ala Asn Phe
385                 390                 395                 400

Thr Gln Val Gly Ser Thr Phe Lys Gly Ile Ile Arg Ala Phe Arg Asp
                405                 410                 415

Tyr Gln Ser Ser Leu His Asn His Lys Val Lys Ile Tyr Val Arg Arg
                420                 425                 430

Gly Gly Pro Asn Trp Gln Glu Gly Leu Arg Leu Ile Lys Ser Ala Gly
                435                 440                 445

Asp Glu Leu Asn Leu Pro Met Glu Ile Tyr Gly Pro Asp Met His Val
                450                 455                 460

Ser Gly Ile Val Pro Leu Ala Leu Leu Gly Lys Arg Pro Lys Asn Val
465                 470                 475                 480

Lys Pro Phe Gly Thr Gly Pro Ser Thr Glu Ala Ser Thr Pro Leu Gly
                485                 490                 495

Val

<210> SEQ ID NO 11
<211> LENGTH: 406
<212> TYPE: DNA
<213> ORGANISM: Yarrowia lipolytica

<400> SEQUENCE: 11
agagaccggg ttggcggcgc atttgtgtcc caaaaaacag ccccaattgc cccaattgac    60
cccaaattga cccagtagcg ggcccaaccc cggcgagagc ccccttctcc ccacatatca   120
aacctccccc ggttcccaca cttgccgtta agggcgtagg gtactgcagt ctggaatcta   180
cgcttgttca gactttgtac tagtttcttt gtctggccat ccgggtaacc catgccggac   240
gcaaaataga ctactgaaaa ttttttttgct ttgtggttgg gactttagcc aagggtataa   300
aagaccaccg tccccgaatt acctttcctc ttcttttctc tctctccttg tcaactcaca   360
cccgaaatcg ttaagcattt ccttctgagt ataagaatca ttcaaa                 406

-continued

```
<210> SEQ ID NO 12
<211> LENGTH: 122
<212> TYPE: DNA
<213> ORGANISM: Yarrowia lipolytica

<400> SEQUENCE: 12
gtgagtttca gaggcagcag caattgccac gggctttgag cacacggccg ggtgtggtcc      60
cattcccatc gacacaagac gccacgtcat ccgaccagca cttttttgcag tactaaccgc    120 ag                                                                    122

<210> SEQ ID NO 13
<211> LENGTH: 531
<212> TYPE: PRT
<213> ORGANISM: Artificial Sequence
<220> FEATURE:
<223> OTHER INFORMATION: TEF promoter-intron sequence

<400> SEQUENCE: 13

Ala Gly Ala Gly Ala Cys Cys Gly Gly Thr Thr Gly Gly Cys Gly
  1               5                  10                  15

Gly Cys Gly Cys Ala Thr Thr Gly Thr Gly Thr Cys Cys Cys Ala
                 20                  25                  30

Ala Ala Ala Ala Cys Ala Gly Cys Cys Cys Ala Ala Thr Thr
             35                  40                  45

Gly Cys Cys Cys Ala Ala Thr Thr Gly Ala Cys Cys Cys Ala
         50                  55                  60

Ala Ala Thr Thr Gly Ala Cys Cys Ala Gly Thr Ala Gly Cys Gly
 65                  70                  75                  80

Gly Gly Cys Cys Cys Ala Ala Cys Cys Cys Gly Gly Cys Gly Ala
                 85                  90                  95

Gly Ala Gly Cys Cys Cys Cys Cys Thr Thr Cys Thr Cys Cys Cys
                100                 105                 110

Ala Cys Ala Thr Ala Thr Cys Ala Ala Ala Cys Cys Thr Cys Cys
            115                 120                 125

Cys Cys Gly Gly Thr Thr Cys Cys Cys Ala Cys Ala Cys Thr Thr Gly
        130                 135                 140

Cys Cys Gly Thr Thr Ala Ala Gly Gly Gly Cys Gly Thr Ala Gly Gly
145                 150                 155                 160

Gly Thr Ala Cys Thr Gly Cys Ala Gly Thr Cys Thr Gly Gly Ala Ala
                165                 170                 175

Thr Cys Thr Ala Cys Gly Cys Thr Thr Gly Thr Thr Cys Ala Gly Ala
            180                 185                 190

Cys Thr Thr Thr Gly Thr Ala Cys Thr Ala Gly Thr Thr Thr Cys Thr
        195                 200                 205

Thr Thr Gly Thr Cys Thr Gly Gly Cys Cys Ala Thr Cys Cys Gly Gly
    210                 215                 220

Gly Thr Ala Ala Cys Cys Cys Ala Thr Gly Cys Cys Gly Gly Ala Cys
225                 230                 235                 240

Gly Cys Ala Ala Ala Ala Thr Ala Gly Ala Cys Thr Ala Cys Thr Gly
                245                 250                 255

Ala Ala Ala Ala Thr Thr Thr Thr Thr Thr Gly Cys Thr Thr Thr
            260                 265                 270

Gly Thr Gly Gly Thr Thr Gly Gly Gly Ala Cys Thr Thr Ala Gly
        275                 280                 285

Cys Cys Ala Ala Gly Gly Gly Thr Ala Thr Ala Ala Ala Gly Ala
    290                 295                 300
```

Cys Cys Ala Cys Cys Gly Thr Cys Cys Cys Gly Ala Ala Thr Thr
305                 310                 315                 320

Ala Cys Cys Thr Thr Thr Cys Cys Thr Thr Cys Thr Thr Thr
            325                 330                 335

Thr Cys Thr Cys Thr Cys Thr Cys Thr Cys Cys Thr Thr Gly Thr Cys
340                 345                 350

Ala Ala Cys Thr Cys Ala Cys Ala Cys Cys Gly Ala Ala Thr
            355                 360             365

Cys Gly Thr Thr Ala Ala Gly Cys Ala Thr Thr Cys Cys Thr Thr
370                 375                 380

Cys Thr Gly Ala Gly Thr Ala Thr Ala Ala Gly Ala Thr Cys Ala
385                 390                 395                 400

Thr Thr Cys Ala Ala Ala Cys Gly Gly Thr Gly Ala Gly Thr Thr
            405                 410                 415

Thr Cys Ala Gly Ala Gly Cys Ala Gly Cys Ala Gly Cys Ala Ala
420                 425                 430

Thr Thr Gly Cys Cys Ala Cys Gly Gly Gly Cys Thr Thr Gly Ala
            435                 440                 445

Gly Cys Ala Cys Ala Cys Gly Gly Cys Cys Gly Gly Thr Gly Thr
450                 455                 460

Gly Gly Thr Cys Cys Cys Ala Thr Thr Cys Cys Ala Thr Cys Gly
465                 470                 475                 480

Ala Cys Ala Cys Ala Gly Ala Cys Gly Cys Cys Ala Cys Gly Thr
                485                 490                 495

Cys Ala Thr Cys Cys Gly Ala Cys Cys Ala Gly Cys Ala Cys Thr
            500                 505                 510

Thr Thr Thr Gly Cys Ala Gly Thr Ala Cys Thr Ala Ala Cys Cys Gly
                515                 520                 525

Cys Ala Gly
    530

<210> SEQ ID NO 14
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 14
gactgtcgac agagaccggg ttggcggcgc atttgtg                              37

<210> SEQ ID NO 15
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 15
gactggtacc tcaagatgca tagcacgcgt tttgaatgat tcttatactc                50

<210> SEQ ID NO 16
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 16

```
ggcagtcgac agagaccggg ttggcggc                                          28
```

<210> SEQ ID NO 17
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 17

```
ttattcacgc gtgtagatac gtactgcaaa aagtgctggt cgga                        44
```

<210> SEQ ID NO 18
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 18

```
aatgaccatg attacggatt cactgg                                            26
```

<210> SEQ ID NO 19
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 19

```
ctaggtggat ccttattttt gacaccagac caactggtaa                             40
```

<210> SEQ ID NO 20
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 20

```
taaccgcaga ccatgattac ggattcactg gcc                                    33
```

<210> SEQ ID NO 21
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 21

```
ctaggtatgc atatgaccat gattacggat tcactgg                                37
```

<210> SEQ ID NO 22
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 22

```
cttacaggta ccttattttt gacaccagac caactggtaa                             40
```

<210> SEQ ID NO 23
<211> LENGTH: 30
<212> TYPE: DNA

<213> ORGANISM: Artificial Sequence
<220> FEATURE:
<223> OTHER INFORMATION: synthetic oligonucleotide

<400> SEQUENCE: 23
gactacgcgt cacaatgcga ctgcaattga                                30

<210> SEQ ID NO 24
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 24
tagcatgcat tcacaacccc ttgagcagct                                30

<210> SEQ ID NO 25
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 25
aatgcgactg caattgagga cactaa                                    26

<210> SEQ ID NO 26
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 26
cgttgaatcg atttcggaca cgggcatctc ac                             32

<210> SEQ ID NO 27
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 27
taaccgcaga ctatcgactc acaatactac aagtcgcg                       38

<210> SEQ ID NO 28
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 28
ctaggtatgc atttactcaa tcattcggaa ctctggg                        37

<210> SEQ ID NO 29
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 29
cccggcaaca attaatagac tggat                                     25

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
ttcggacacg ggcatctcac                                              20

<210> SEQ ID NO 31
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 31
cttacaacgc gtatgtctgc caacgagaac atctcc                            36

<210> SEQ ID NO 32
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 32
ctaggtatgc atctatgatc gagtcttggc cttgga                            36

<210> SEQ ID NO 33
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 33
cttacaacgc gtatgtcagc gaaatccatt cacga                             35

<210> SEQ ID NO 34
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 34
ctaggtatgc atttaaactc cgagaggagt ggaagc                            36

<210> SEQ ID NO 35
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 35
aatggtgaaa aacgtggacc aagtg                                        25

<210> SEQ ID NO 36
<211> LENGTH: 36
<212> TYPE: DNA
<213> ORGANISM: Artificial Sequence
<220> FEATURE:

```
<223> OTHER INFORMATION: synthetic oligonucleotide

<400> SEQUENCE: 36
ctcacaggat ccctaagcag ccatgccaga catacc                                    36

<210> SEQ ID NO 37
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 37
cccggcaaca attaatagac tggat                                                25

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
ttcggacacg ggcatctcac                                                      20

<210> SEQ ID NO 39
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 39
tccaggccgt cctctccc                                                        18

<210> SEQ ID NO 40
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 40
ggccagccat atcgagtcgc a                                                    21

<210> SEQ ID NO 41
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 41
aacggaggag tggtcaagcg a                                                    21

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
ttatggggaa gtagcggcca a                                                    21
```

```
<210> SEQ ID NO 43
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 43
gaccgactcc aacaaggacc ctt                                              23

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
gggttgggca caagcagcat                                                  20

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gcttctcacg gaggtcatac agt                                              23

<210> SEQ ID NO 46
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 46
ctgcggcaat accgttgtta g                                                21

<210> SEQ ID NO 47
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 47
cctccttggt gaggttggtg gt                                               22

<210> SEQ ID NO 48
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 48
gcgacgatgg gcttcttgat c                                                21

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 49
ccttcaaggg catcatccgg                                              20

<210> SEQ ID NO 50
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 50
cgcctcgtcg cacgtaaatc t                                            21
```